United States Patent
Sun et al.

(10) Patent No.: US 10,308,704 B2
(45) Date of Patent: *Jun. 4, 2019

(54) ISOLATED NUCLEIC ACID MOLECULES ENCODING STABILIZED RECEPTOR POLYPEPTIDES AND USES THEREOF

(71) Applicant: Amgen Inc., Thousand Oaks, CA (US)

(72) Inventors: Jeonghoon Sun, San Diego, CA (US); Lei-Ting Tony Tam, Thousand Oaks, CA (US); Mark Leo Michaels, Encino, CA (US); Thomas Charles Boone, Newbury Park, CA (US); Rohini Deshpande, Camarillo, CA (US); Yue-Sheng Li, Cambridge, MA (US); Huiquan Han, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/004,375

(22) Filed: Jan. 22, 2016

(65) Prior Publication Data

US 2016/0137718 A1 May 19, 2016
US 2017/0183391 A9 Jun. 29, 2017

Related U.S. Application Data

(60) Continuation of application No. 13/775,756, filed on Feb. 25, 2013, now Pat. No. 9,273,114, which is a division of application No. 12/626,375, filed on Nov. 25, 2009, now Pat. No. 8,410,043.

(60) Provisional application No. 61/200,250, filed on Nov. 26, 2008, provisional application No. 61/259,060, filed on Nov. 6, 2009.

(51) Int. Cl.
*C07K 14/71* (2006.01)
*C07K 14/495* (2006.01)
*A61K 38/00* (2006.01)

(52) U.S. Cl.
CPC ............ *C07K 14/71* (2013.01); *C07K 14/495* (2013.01); *A61K 38/00* (2013.01)

(58) Field of Classification Search
CPC .................................. C07K 14/71; A61K 38/00
See application file for complete search history.

(56) References Cited

U.S. PATENT DOCUMENTS

| | | |
|---|---|---|
| 3,773,919 A | 11/1973 | Boswell et al. |
| 4,411,993 A | 10/1983 | Gillis |
| 4,543,439 A | 9/1985 | Frackelton, Jr. et al. |
| RE32,011 E | 10/1985 | Zimmerman et al. |
| 4,816,567 A | 3/1989 | Cabilly et al. |
| 4,902,614 A | 2/1990 | Wakabayashi et al. |
| 5,567,584 A | 10/1996 | Sledziewski et al. |
| 5,595,898 A | 1/1997 | Robinson et al. |
| 5,693,493 A | 12/1997 | Robinson et al. |
| 5,750,375 A | 5/1998 | Sledziewski et al. |
| 5,827,733 A | 10/1998 | Lee et al. |
| 5,863,738 A | 1/1999 | Dijke et al. |
| 5,885,794 A | 3/1999 | Mathews et al. |
| 5,994,618 A | 11/1999 | Lee et al. |
| 6,096,506 A | 8/2000 | Lee et al. |
| 6,162,896 A | 12/2000 | Mathews et al. |
| 6,300,129 B1 | 10/2001 | Lonberg et al. |
| 6,465,239 B1 | 10/2002 | Lee et al. |
| 6,468,535 B1 | 10/2002 | Lee et al. |
| 6,472,179 B2 | 10/2002 | Stahl et al. |
| 6,500,664 B1 | 12/2002 | Lee et al. |
| 6,599,876 B2 | 7/2003 | Kojima |
| 6,607,884 B1 | 8/2003 | Lee et al. |
| 6,656,475 B1 | 12/2003 | Lee et al. |
| 6,812,339 B1 | 11/2004 | Venter et al. |
| 6,858,208 B2 | 2/2005 | Lee et al. |
| 6,891,082 B2 | 5/2005 | Lee et al. |
| 7,166,707 B2 | 1/2007 | Feige |
| 7,189,827 B2 | 3/2007 | Feige |
| 7,399,848 B2 | 7/2008 | Lee et al. |
| 7,442,778 B2 | 10/2008 | Gegg et al. |
| 7,511,012 B2 | 3/2009 | Han et al. |
| 7,534,432 B2 | 5/2009 | Lee et al. |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,709,605 B2 | 5/2010 | Knopf et al. |
| 7,736,653 B2 | 6/2010 | Kim et al. |
| 7,737,260 B2 | 6/2010 | Kim et al. |
| 7,750,127 B2 | 7/2010 | Gegg et al. |

(Continued)

FOREIGN PATENT DOCUMENTS

| | | |
|---|---|---|
| CA | 1219215 A | 3/1987 |
| EP | 36676 A1 | 9/1981 |

(Continued)

OTHER PUBLICATIONS

Office Action for Japanese Patent Application No. JP2014-548827, dated Sep. 28, 2016, 7 Pages.
Supplementary European Search Report for European Patent Application No. EP 14746114, dated Aug. 9, 2016, 19 Pages.
Extended European Search Report for European Patent Application No. EP 16179980.4, dated Sep. 7, 2016, 7 Pages.
Office Action for Korean Patent Application No. KR 10-2012-7008467, dated Sep. 7, 2016, 6 Pages, (With Concise Explanation of Relevance).

(Continued)

*Primary Examiner* — Gyan Chandra
(74) *Attorney, Agent, or Firm* — Lisa E. Alexander

(57) ABSTRACT

The present invention provides stabilized activin IIB receptor polypeptides and proteins capable of binding and inhibiting the activities of activin A, myostatin, or GDF-11. The present invention also provides polynucleotides, vectors and host cells capable of producing the stabilized polypeptides and proteins. Compositions and methods for treating muscle-wasting diseases and metabolic disorders are also provided.

8 Claims, 3 Drawing Sheets

Specification includes a Sequence Listing.

(56) References Cited

U.S. PATENT DOCUMENTS

| | | | |
|---|---|---|---|
| 7,750,128 | B2 | 7/2010 | Gegg et al. |
| 7,803,923 | B2 | 9/2010 | Han et al. |
| 7,842,663 | B2 | 11/2010 | Knopf et al. |
| 7,928,075 | B2 | 4/2011 | Han et al. |
| 7,947,646 | B2 | 5/2011 | Sun et al. |
| 8,058,229 | B2 | 11/2011 | Seehra et al. |
| 8,067,562 | B2 | 11/2011 | Han et al. |
| 8,071,538 | B2 | 12/2011 | Han et al. |
| 8,110,665 | B2 | 2/2012 | Kim et al. |
| 8,124,094 | B2 | 2/2012 | Kim et al. |
| 8,138,142 | B2 | 3/2012 | Seehra et al. |
| 8,178,488 | B2 | 5/2012 | Knopf et al. |
| 8,216,997 | B2 | 7/2012 | Seehra et al. |
| 8,252,900 | B2 | 8/2012 | Knopf et al. |
| 8,343,933 | B2 | 1/2013 | Knopf et al. |
| 8,361,957 | B2 | 1/2013 | Seehra et al. |
| 8,410,043 | B2 | 4/2013 | Sun et al. |
| 9,273,114 | B2 | 3/2016 | Sun et al. |
| 2004/0223966 | A1 | 11/2004 | Wolfman et al. |
| 2005/0014733 | A1 | 1/2005 | Whittemore et al. |
| 2005/0186593 | A1 | 8/2005 | Mathews et al. |
| 2006/0034831 | A1 | 2/2006 | Tobin |
| 2007/0065444 | A1 | 3/2007 | North et al. |
| 2009/0047281 | A1 | 2/2009 | Sherman et al. |
| 2009/0118188 | A1 | 5/2009 | Knopf et al. |
| 2010/0008918 | A1 | 1/2010 | Sherman et al. |
| 2010/0168020 | A1 | 7/2010 | Sun et al. |
| 2010/0272734 | A1 | 10/2010 | Berger et al. |
| 2010/0310506 | A1 | 12/2010 | Coti et al. |
| 2011/0034372 | A1 | 2/2011 | Lee et al. |
| 2011/0183897 | A1 | 7/2011 | Sun et al. |
| 2011/0243933 | A1 | 10/2011 | Poradosu et al. |
| 2011/0281796 | A1 | 11/2011 | Han et al. |
| 2012/0121576 | A1 | 5/2012 | Seehra et al. |
| 2012/0148588 | A1 | 6/2012 | Knopf et al. |
| 2012/0156204 | A1 | 6/2012 | Seehra et al. |
| 2012/0295814 | A1 | 11/2012 | Cramer et al. |
| 2012/0328595 | A1 | 12/2012 | Sun et al. |
| 2013/0030159 | A1 | 1/2013 | Han et al. |
| 2013/0071393 | A1 | 3/2013 | Seehra et al. |

FOREIGN PATENT DOCUMENTS

| | | |
|---|---|---|
| EP | 58481 A1 | 8/1982 |
| EP | 88046 A2 | 9/1983 |
| EP | 133988 A2 | 3/1985 |
| EP | 143949 A1 | 6/1985 |
| EP | 2370463 A2 | 10/2011 |
| JP | 2006-516886 A | 7/2006 |
| JP | 2009-513162 A | 4/2009 |
| JP | 2010-518009 | 5/2010 |
| JP | 2010-519931 A | 6/2010 |
| JP | 2010-539236 | 12/2010 |
| JP | 2013027391 | 2/2013 |
| JP | 5349966 | 11/2013 |
| KR | 10-1428344 | 8/2014 |
| WO | WO 93/15722 A1 | 8/1993 |
| WO | WO 94/09817 A1 | 5/1994 |
| WO | WO 94/10332 A1 | 5/1994 |
| WO | WO 94/20069 A1 | 9/1994 |
| WO | WO 99/38890 A1 | 8/1999 |
| WO | WO 00/29581 A1 | 5/2000 |
| WO | WO 00/43781 A2 | 7/2000 |
| WO | WO 2004/039948 A2 | 5/2004 |
| WO | WO 2006/012627 A2 | 2/2006 |
| WO | WO 2006/020884 A2 | 2/2006 |
| WO | WO 2007/053775 A1 | 5/2007 |
| WO | WO 2008/031061 A2 | 3/2008 |
| WO | WO 2008/097541 A2 | 8/2008 |
| WO | WO 2008/113185 A1 | 9/2008 |
| WO | WO 2010/019261 A1 | 2/2010 |
| WO | WO 2010/062383 A2 | 6/2010 |
| WO | WO 2013/106715 A1 | 7/2013 |
| WO | WO 2008/109167 A2 | 9/2018 |

OTHER PUBLICATIONS

Office Action for Mexican Patent Application No. MX/E/2015/011882, dated Aug. 30, 2016, 3 Pages, (With Concise Explanation of Relevance).

Office Action for Canadian Patent Application No. CA-2,743,850, dated Sep. 9, 2016, 3 Pages.

Tsai, C.-L., et al., "Secreted Stress-Induced Phosphoprotein 1 Activates the ALK2-SMAD Signaling Pathways and Promotes Cell Proliferation of Ovarian Cancer Cells," Cell Reports, Aug. 2012, pp. 283-293, vol. 2, No. 2.

Akerstrom et al., "Protein G: A Powerful Tool for Binding and Detection of Monoclonal and Polyclonal Antibodies," Journal of Immunology, 135(4):2589-2592, 1985.

Alibhai, SMH, et al., "Long-term side effects of androgen deprivation therapy in men with non-metastatic prostate cancer: a systematic literature review," Crit Rev Oncol/Hematol. 2006, vol. 60, pp. 201-215.

Attisano, L., et al., "Activation of Signalling by the Activin Receptor Complex," Molecular and Cellular Biology, Mar. 1996, p. 1066-1073, vol. 16. No. 3.

Attisano, L., et al., "Novel Activin Receptors: Distinct Genes and Alternative mRNA Splicing Generate a Repertoire of Serine/Threonine Kinase Receptors," Cell, Jan. 1992, vol. 68, pp. 97-108.

Augustin, H.G., et al., "Control of vascular morphogenesis and homeostasis through the angiopoietin-Tie system," Nature Reviews Molecular Cell Biology, 2009, vol. 10, pp. 165-177.

Barany, et al., "Solid-phase peptide syntheses: a silver anniversary report," Int. J. Peptide Protein Res., 30:705-739, 1987.

Barany, et al., "Solid-phase peptide synthesis," Ch. 1, The Peptides: Analysis, Synthesis, Biology, vol. 2, Gross and Meienhofer, eds., (Academic Press, New York, 1980), pp. 1-284.

Berrondo, M., "Predicting the structure and function of protein mutants," A Dissertation submitted to Johns Hopkins University in conformity with the requirements for the degree of Doctor of Philosophy Baltimore, Maryland, Jan. 2010, 176 Pages, Can be retrieved at <URL:http://graylab.jhu.edu/publications/dissertations/Berrondo2010.pd- f>.

Bogdanovish, S., et al., "Myostatin blockade improves function but not histopathology in a murine model of limb-girdle muscular dystrophy 2C," Muscle Nerve, Mar. 2008, pp. 308-316, vol. 37, No. 3.

Bowie, J.U., et al., "Deciphering the message in protein sequences: tolerance to amino acid substitutions" Science, Mar. 16, 1990, vol. 247, No. 4948, pp. 1306-1310.

Campbell, K., et al., "Totipotency of Multipotentiality of Cultured Cells: Applications and Progress," Theriogenology, Jan. 1, 1997, vol. 47, Issue 1, pp. 63-72.

Chang, K.P., et al., "Overexpression of activin A in oral squamous cell carcinoma: association with poor prognosis and tumor progression," Ann Surg Oncol. 2010, vol. 17, pp. 1945-1956.

Chaubert, et al., "Simultaneous Double Immunoenzymatic Labeling: A New Procedure for the Histopathologic Routine," Modern Pathology, 10(6):585-591, 1997.

Choi, J.-H., et al., "Gonadotropins and ovarian cancer," Endocrine Reviews, 2007, vol. 28, pp. 440-461.

Ciprano, S., et al., "Follistatin Is a Modulator of Gonadal Tumor Progression and the Activin-Induced Wasting Syndrome in Inhibin-Deficient Mice," Endocrinology, 2000, vol. 141, No. 7, pp. 2319-2327.

Cobellis, L., et al. "High concentrations of activin A in the peritoneal fluid of women with epithelial ovarian cancer," J Soc Gynecol Investig. 2004, vol. 11, pp. 203-206.

Coerver, K., et al., "Activin Signaling through Activin Receptor Type II Causes the Cachexia-Like Symptions in Inhibin-Deficient Mice," Molecular Endocrinology, 1996, vol. 10, No. 5, pp. 534-543.

Communication pursuant to Article 94(3) EPC for European Patent Application No. 09761055.4, dated Apr. 28, 2014, 3 Pages.

Communication Pursuant to Article 94(3) EPC for European Patent Application No. EP 06827481.0, dated Jul. 20, 2010, 2 pages.

Communication Pursuant to Article 94(3) EPC for European Patent Application No. EP 06827481.0, dated May 30, 2011, 3 pages.

(56) References Cited

OTHER PUBLICATIONS

Communication pursuant to Article 94(3) EPC for European Patent Application No. EP 09761055.4, dated Sep. 3, 2013, 3 Pages.
Communication Pursuant to Article 94(3) EPC for European Patent Application No. EP 09761055.4, dated Sep. 13, 2012, 2 pages.
Communication Pursuant to Article 94(3) EPC for European Patent Application No. EP 06827481.0, dated Sep. 9, 2008, 2 pages.
Communication pursuant to Article 94(3) EPC for European Patent Application No. EP 08742032.9, dated Aug. 21, 2015, 3 Pages.
Communication Pursuant to Article 94(3) EPC for European Patent Application No. EP 08742032.9, dated Apr. 18, 2013, 4 pages.
Database EMBL Accession No. AY421275, "Homo sapiens ACVR2B gene, Virtual Transcript, partial sequence, genomic survey sequence," Dec. 13, 2003, 2 Pages.
Database Geneseq Accession No. AAW86245, "Mouse ActRIIB4 receptor protein," Feb. 16, 1999, 1 Page.
Database Geneseq Accession No. AD043580, "Amino acid sequence of ActRIIB," Jul. 29, 2004, 2 Pages.
De Kretser DM, et al., "Activin A and follistatin: their role in the acute phase reaction and inflammation," Journal of Endocrinology. 1999, vol. 161, pp. 195-198.
Decision on Examination for Taiwan Patent Application No. TW 097107642, Aug. 29, 2012, 4 Pages.
Dennier, et al., "Direct binding of Smad3 and Smad4 to critical TGF.beta.-inducible elements in the promoter of human plasminogen activator inhibitor-type 1 gene," The EMBO Journal, 17(11):3091-3100, 1998.
Derynck, R., et al., "Smads: Transcriptional Activators of TGF-.beta. Responses," Cell, Dec. 11, 1998, vol. 95, pp. 737-740.
Do TV, "The role of activin A and Akt/GSK signaling in ovarian tumor biology," Endocrinology. 2008, vol. 149, pp. 3809-3816.
Donaldson, C., et al., "Activin and Inhibin Binding to the Soluble Extracellular Domain of Activin Receptor II," Endocrinology, 1999, pp. 1760-1766, vol. 140, No. 4.
Durocher, et al., "High-level and high-throughput recombinant protein production by transient transfection of suspension-growing human 293-EBNA1 cells," Nucleic Acids Research, 30(2e9) 2002.
Dvorak, H.F., et al., "Tumor microenvironment and progression," Journal of Surgical Oncology, 2011, vol. 103, pp. 468-474.
EBI, Swissprot Accession No. 095390, GDFIIsub.—Human, Growth/differentiation factor 1l, 2 pages, [online] [retrieved on Sep. 9, 2010] Retrieved from the internet <URL:http://www.ebi.ac.uk/uniprot/unisave/?help=0&session=/ebi/exterv/- old-work/SESSION14 . . . >.
Ellis, L.M., et al., "VEGF-targeted therapy: mechanisms of antitumour activity," Nature Reviews Cancer, 2008, vol. 8, pp. 579-591.
Eppstein, et al., "Biological activity of liposome-encapsulated murine interferon .gamma. is mediated by a cell membrane receptor," Proc. Natl. Acad. Sci. USA, 82:3688-3692, 1985.
Ethier, J-F., et al., "Bovine Activin Receptor Type IIB Messenger Ribonucleic Acid Displays Alternative Splicing Involving a Sequence Homologous to Src-Homology 3 domain Binding Sites," Endocrinology, Jun. 1997, vol. 138, No. 6, p. 2425-2434.
Examination Report for Australian Patent Application No. AU 2013216639, dated Apr. 30, 2015, 4 Pages.
Examination Report for Australian Patent Application No. AU 2014210609, dated Sep. 23, 2015, 2 Pages.
Examination Report for Gulf Cooperation Council Application No. GCC/P/2008/10291, dated Sep. 7, 2012, 6 Pages.
Examination Report for Malaysia Patent Application No. PI20093636, dated Dec. 31, 2013, 3 Pages.
Examination Report From the Intellectual Property Office for Taiwan Patent Application No. 098140431, dated Jun. 18, 2012, 11 pages.
Examiner's First Report for Canadian Patent Application No. CA 2,627,200, dated Jun. 7, 2010, 3 pages.
Examiner's First report on Australian Patent Application No. AU 2009320364, dated Nov. 30, 2011, 2 pages.
Examiner's Second Report for Canadian Patent Application No. CA 2,627,200, dated Nov. 2, 2011, 2 pages.

Examiner's Third Report for Canadian Patent Application No. CA 2,627,200, dated May 28, 2012, 1 page.
Final Rejection Office Action for Japanese Patent Application No. 2009-552758, dated Aug. 1, 2013, 5 Pages.
First Examination Report for India Application No. 6356/DELNP/2009, dated Jan. 20, 2015, 3 pages.
First Examination Report for New Zealand Patent Application No. 604818, dated Jan. 8, 2013, 2 Pages.
First Examination Report for New Zealand Patent Application No. 627111, dated Jul. 24, 2014, 1 page.
First Examination Report for New Zealand Patent Application No. NZ 626580, dated Mar. 18, 2015, 2 Pages.
First Office Action for Chinese Patent Application No. 200980147945.3, dated Mar. 21, 2013, 7 Pages.
First Office Action for Eurasian Patent Application No. EA 200970810/28, dated Sep. 15, 2011, 2 Pages.
Gabizon A, et al., "Polyethylene glycol-coated (pegylated) liposomal doxorubicin: rationale for use in solid tumours," Drugs. 1997, vol. 54 (suppl 4), pp. 15-21.
Gamer, L., et al., "A Novel BMP Expressed in Developing Mouse Limb, Spinal Cord, and Tail Bud Is a Potent Mesoderm Inducer in Xenopus Embryos," Developmental Biology, 1999, vol. 208, No. 1, pp. 222-232.
Geisse, S., et al., "Eukaryotic Expression Systems: a Comparison," Protein Expression and Purification, Nov. 1996, pp. 271-282, vol. 8, Is. 3, Academic Press, Inc.
Gibbs, R., et al., "Evolutionary and Biomedical Insights from the Rhesus Macaque Genome," Science, Apr. 13, 2007, pp. 222-234, vol. 316.
Gluzman, et al., "SV40-Transformed Simian Cells Support the Replication of Early SV40 Mutants," Cell, 23:175-182, 1981.
Gonzalez-Cadavid, N., et al., "Organization of the human myostatin gene and expression in healthy men and HIV-infected men with muscle wasting," PNAS USA, 1998, vol. 95, pp. 14938-14943.
Gray, P., et al., "Identification of a Binding Site on the Type II Activin Receptor for Activin and Inhibin," J. Biol. Chem., Feb. 4, 2000, vol. 275, No. 5, pp. 3206-3212.
Hamrick, M., et al., "Bone Mineral Content and Density in the Humerus of Adult Myostatin-Deficient Mice," Calcified Tissue International, 2002, vol. 71, No. 1, pp. 63-68.
Harada K, et al., "Serum immunoreactive activin A levels in normal subjects and patients with various diseases," J Clin Endocrinol Metab. 1996, vol. 81, pp. 2125-2130.
Harrison, C.A., et al., "Antagonists of activin signaling: mechanisms and potential biological applications," Trends in Endocrinology and Metabolism, Mar. 2005, vol. 16, No. 2, pp. 73-78.
Harrison, et al., "An Activin Mutant with Disrupted ALK4 Binding Blocks Signaling via Type II Receptors," Journal of Biological Chemistry, 279(27):28036-28044, 2004.
Hilden, K., et al., "Expression of Type II Activin Receptor Genes During Differentiation of Human K562 Cells and cDNA Cloning of the Human Type IIB Activin Receptor," Blood, Apr. 15, 1994, pp. 2163-2170, vol. 83, No. 8.
Holzbaur, E.L., et al., Myostatin inhibition slows muscle atrophy in rodent models of amyotrophic lateral sclerosis, Neurobiology of Disease, 2006, pp. 697-707, vol. 23.
Hubner G, et al., "Activin: a novel player in tissue repair processes," Histology & Histopathology. 1999, vol. 14, pp. 295-304.
Intellectual Property Office of the Philippines, Notice of Allowance, Philippine Patent Application No. 1/2009/501698, dated Feb. 5, 2015, 1 page.
International Search Report, PCT/US2006/043044, dated Mar. 15, 2007, 6 Pages.
Invitation to Response to Written Opinion, Singapore Patent Application No. 201103777-7, dated Aug. 1, 2012, 5 pages.
Ito, et al., "Presence of activin signal transduction in normal ovarian cells and epithelial ovarian carcinoma," British Journal of Cancer, 82(8):1415-1420, 2000.
Jones KL, et al., "Activin A and follistatin in systemic inflammation," Molecular & Cellular Endocrinology. 2004, vol. 225, pp. 119-125.

(56) References Cited

OTHER PUBLICATIONS

Kaufman, R., et al., "Transgenic Analysis of a 100-kb Human .beta.-Globin Cluster-Containing DNA Fragment Propagated as a Bacterial Artificial Chromosome," Blood, Nov. 1, 1999, vol. 94, No. 9, pp. 3178-3184.
Kinglsey, D., et al., "The TGF-.beta. superfamily: new members, new receptors, and new genetic tests of function in different organisms," Genes Dev., 1994, vol. 8, pp. 133-146.
Konishi, I. "Gonadotropins and ovarian carcinogenesis: a new era of basic research and its clinical implications," Int J Gynecol Cancer, 2006, vol. 16, pp. 16-22.
Kostelny, et al., "Formation of a Bispecific Antibody by the Use of Leucine Zippers," Journal of Immunology, 148(5):1547-1553, 1992.
Kwak, K.S., et al., "Regulation of protein catabolism by muscle-specific and cytokine-inducible ubiquitin ligase E3alpha-II during cancer cachexia," Cancer Res, 2004, vol. 64, pp. 8193-8198.
Lalani, R., et al., "Myostatin and insulin-like growth factor-I and -II expression in the muscle of rafts exposed to the microgravity environment of the NeuroLab space shuttle flight," Journal of Endocrinology, 2000, vol. 167, pp. 417-428.
Lambert-Messerlian GM, et al., "Secretion of activin A in recurrent epithelial ovarian carcinoma," Gynecol Oncol. 1999, vol. 74, pp. 93-97.
Lang, C., et al., "Regulation of myostatin by glucocorticoids after thermal injury," FASEB, 2001, vol. 1, No. 15, pp. 1807-1809.
Langer, "Controlled release of macromolecules," ChemTech, 12:98-105, 1982.
Langer, et al., "Biocompatibility of polymeric delivery systems for macromolecules," J. of Biomedical Materials Research, 15:267-277, 1981.
Lee, SJ., et al., "Regulation of muscle growth by multiple ligands signaling through activin type II receptors," Proc. Natl. Acad. Sci. USA, Dec. 2005, vol. 102, No. 50, pp. 18117-18122.
Lee, SJ., et al., "Regulation of myostatin activity and muscle growth," Proc. Natl. Acad. Sci. USA, Jul. 2001, vol. 98, No. 16, pp. 9306-9311.
Ling, N., et al., "Pituitary FSH is released by a heterodimer of the .beta.-subunits from the two forms of inhibin," Nature, 1986, vol. 321, pp. 779-782.
Longfellow, C., et al., "Thermodynamic and Spectroscopic Study of Bulge Loops in Oligoribonucleotides," Biochemistry, 1990, vol. 29, pp. 278-285.
Luisi, S., et al., "Expression and secretion of activin A: possible physiological and clinical implications," European Journal of Endocrinology, 2001, vol. 145, pp. 225-236.
MacDonald, N., et al., "Understanding and managing cancer cachexia," J Am Coll Surg. 2003, vol. 197, pp. 143-161.
Macias-Silva, et al., "MADR2 Is a Substrate of the TGF.beta. Receptor and Its Phosphorylation Is Required for Nuclear Accumulation and Signaling," Cell, 87:1215-1224, 1996.
Mason, A., et al., "Complementary DNA sequences of ovarian follicular fluid inhibin show precursor structure and homology with transforming growth factor-.beta.," Nature, Dec. 1985, pp. 659-663, vol. 318.
Massague, J., "How Cells Read TGF-.beta. Signals," Nature Rev: Molecular Cell Biology, 2000, pp. 169-178, vol. 1.
Mathews, L.S., "Activin Receptors and Cellular Signaling by the Receptor Serine Kinase Family," Endocrine Review, 1994, vol. 15, pp. 310-325.
Matzuk, MM, et al., ".alpha.-inhibin is a tumour-suppressor gene with gonadal specificity in mice," Nature, 1992, vol. 360, pp. 313-319.
Matzuk, MM, et al., "Development of cancer cachexia-like syndrome and adrenal tumors in inhibin-deficient mice," Proc Nati Acad Sci USA. 1994, vol. 91, pp. 8817-8321.
McMahan, et al., "A novel IL-1 receptor, cloned from B cells by mammalian expression, is expressed in many cell types," The EMBO Journal, 10(10):2821-2832, 1991.
McPherron, A., et al., "Double muscling in cattle due to mutations in the myostatin gene," PNAS USA 1997, vol. 94, pp. 12457-12461.
McPherron, A., et al., "Regulation of anterior/posterior patterning of the axial skeleton by growth/differentiation factor 11," Nature Genetics, 1999, vol. 22, No. 93, pp. 260-264.
McPherron, A., et al., "Regulation of skeletal muscle mass in mice by a new TGF-.beta. superfamily member," Nature (London), May 1997, vol. 387, pp. 83-90.
McPherron, et al., "The Transforming Growth Factor .beta. Superfamily," in Growth Factors and Cytokines in Health and Disease, vol. 1B, D. LeRoith and C. Bondy, eds., (JAI Press Inc., Greenwich, CT, USA), pp. 357-393, 1996.
Mendez, et al., "Functional transplant of megabase human immunoglobulin loci recapitulates human antibody response in mice," Nature Genetics 15:146-156, 1997.
Merrifield, "Solid Phase Synthesis," Science, 232:341-347, 1986.
Mikaelian, et al., "Modification of the Overlap Extension Method for Extensive Mutagenesis on the Same Template," Methods in Molecular Biology, 57:193-202, 1996.
Morley, JE., et al., "Cachexia: pathophysiology and clinical relevance," Am J Clin Nutr. 2006, vol. 83, pp. 735-743.
Muscaritoli, M., et al., "Prevention and treatment of cancer cachexia: new insights into an old problem," Eur J Cancer. 2006, vol. 42, pp. 31-41.
NCBI, "Genbank Accession No. AAB86694, myostatin [*Homo sapiens*]," Nov. 20, 1997, 2 Pages, [online] [retrieved on Sep. 9, 2010] Retrieved from the internet <URL:http://www.ncbi.nlm.nih.gov/protein/116734708>.
NCBI, "Genbank Accession No. NM 002192, *Homo sapiens* inhibin, beta A (INHBA), mRNA," Aug. 3, 2010, 4 pages, [online] [retrieved on Sep. 9, 2010] Retrieved from the internet <URL:http://www.ncbi.nlm.nih.gov/nuccore/62953137>.
NCBI, "Genbank Accession No. NP 001097, activin receptor type-2B precursor [*Homo sapiens*]," Aug. 3, 2010, 3 pages, [online] [retrieved on Sep. 9, 2010] Retrieved from the internet <URL:http://www.ncbi.nlm.nih.gov/nuccore/116734708>.
Ngo, J.T., et al., "Computational Complexity, Protein Structure Prediction, and the Levinthal Paradox," The Protein Folding Problem and Tertiary Structure Prediction, pp. 492-495, 1994.
Notice of Final Rejection for Korean Patent Application No. KR 2009-7020320, dated Sep. 4, 2012, 2 Pages.
Notice of Preliminary Rejection Office Action Summary for Korean Patent Application No. 2012-7008467, dated Apr. 18, 2013, 3 pages.
Notification of Reasons for Rejection for Japanese Patent Application No. JP 2008-539077, dated Dec. 19, 2012, 5 Pages.
Notification of Reasons for Rejection for Japanese Patent Application No. JP 2008-539077, dated Feb. 2, 2012, 3 Pages.
Notification of Reexamination Board Opinion for Chinese Patent Application No. CN 200880007116.0, dated Apr. 3, 2015, 11 Pages.
Office Action for Canadian Patent Application No. 2,743,850, dated Nov. 6, 2014, 3 pages.
Office Action for Canadian Patent Application No. 2,743,850, dated Sep. 5, 2012, 4 pages.
Office Action for Canadian Patent Application No. 2,679,841, dated Apr. 28, 2014, 2 Pages.
Office Action for Canadian Patent Application No. 2,679,841, dated Apr. 8, 2013, 2 Pages.
Office Action for Canadian Patent Application No. 2,743,350, dated Oct. 19, 2015, 4 pages.
Office Action for Canadian Patent Application No. 2,743,580, dated Oct. 24, 2013, 2 Pages.
Office Action for Chilean Patent Application No. 1239-2011, dated Apr. 22, 2014, 75 pages.
Office Action for Chinese Patent Application No. CN 200880007116.0, dated Feb. 22, 2013, 13 Pages.
Office Action for Chinese Patent Application No. CN 200980147945.3, dated Nov. 29, 2013, 9 Pages.
Office Action for Colombian Patent Application No. 11-79058-5, dated Nov. 15, 2012, 15 Pages.
Office Action for Colombian Patent Application No. 1239-2011 dated Jun. 18, 2013, 34 Pages.
Office Action for Columbia Patent Application No. CO 11-79058-8, dated Jun. 17, 2013, 11 Pages.
Office Action for Columbian Patent Application No. 11.079.058, dated May 14, 2014, 12 Pages.

(56) References Cited

OTHER PUBLICATIONS

Office Action for Costa Rica Application No. 11054, dated Jan. 26, 2015, 15 pages.
Office Action for Costa Rica Patent Application No. 11054, dated Sep. 17, 2015, 16 Pages (With Concise Explanation of Relevance).
Office Action for Costa Rica Patent Application No. 11054, dated Sep. 24, 2014, 9 Pages.
Office Action for Egypt Patent Application No. PCT13142009, dated May 1, 2013, 11 Pages.
Office Action for Eurasian Application No. 201100832, dated Nov. 28, 2014, 3 pages.
Office Action for Eurasian Patent Application No. 201100832, dated Aug. 26, 2015, 2 Pages.
Office Action for Eurasian Patent Application No. 201100832/28 dated Feb. 27, 2014, 3 Pages.
Office Action for Israeli Patent Application No. 200605, dated Aug. 7, 2014, 4 Pages.
Office Action for Japan Application No. 2012-171705, dated Feb. 4, 2015, 8 pages.
Office Action for Japanese Patent Application No. 2011-538599 dated Apr. 17, 2014, 6 Pages.
Office Action for Japanese Patent Application No. 2012-171705 dated Apr. 2, 2014, 8 Pages.
Office Action for Japanese Patent Application No. JP 2009-552758, dated Feb. 20, 2013, 2 Pages.
Office Action for Japanese Patent Application No. JP 2014-177598, dated Oct. 14, 2015, 6 Pages.
Office Action for Korean Patent Application No. KR 2012-7008467, dated Oct. 18, 2013, 4 Pages.
Office Action for Mexican Patent Application No. MX/a/2012/008808, dated May 2, 2014, 10 Pages.
Office Action for Mexican Patent Application No. MX/a/2012/014888, dated Jun. 27, 2014, 4 Pages.
Office Action for Mexico Patent Application No. MX/a/2011/005505, dated May 28, 2013, 9 Pages.
Office Action for New Zealand Patent Application No. 604818 dated Apr. 2, 2014, 2 Pages.
Office Action for Peru Application No. 1077-2011, dated Nov. 20, 2014, 12 pages.
Office Action for Peru Patent Application No. 000436.2008, dated May 21, 2014, 58 Pages.
Office Action for Philippine Patent Application No. 1/2009/501698, dated Nov. 18, 2014, 1 page.
Office Action for Philippine Patent Application No. 1-2009-501698, dated Jul. 10, 2013, 2 Pages.
Office Action for Taiwan Patent Application No. 097107642 dated Feb. 17, 2014, 3 Pages.
Office Action for Taiwan Patent Application No. 098140431, dated Apr. 25, 2013, 3 Pages.
Office Action for U.S. Appl. No. 13/932,421, dated Jul. 28, 2014, 7 Pages.
Office Action for U.S. Appl. No. 14/085,056, dated Jul. 17, 2015, 8 Pages.
Office Action for U.S. Appl. No. 14/204,460, dated Jul. 22, 2015, 16 Pages.
Office Action for Ukrainian Patent Application No. a 2011 07872, dated Oct. 25, 2012, 2 Pages.
Office Action for Vietnamese Application No. 1-2014-02367, dated Nov. 17, 2014, 2 pages.
Office Action for Vietnamese Patent Application No. 1-2011-01521, dated Jul. 27, 2015, 2 Pages.
Office Action issued by Intellectual Property Office of the Philippines, Patent Application No. 1-2009-501698, dated Oct. 25, 2012, 2 Pages.
Oh, S., et al., "Activin type IIA and IIB receptors mediate Gdf11 signaling in axial vertebral patterning," Genes & Development, 2002, vol. 16, pp. 2749-2754.
Oh, S., et al., "The signaling pathway mediated by the type IIB activin receptor controls axial patterning and laternal asymmetry in the mouse," Genes Dev, 1997, vol. 11, pp. 1812-1826.
Opposition by AG Pharmaceutical Laboratories Industrial Association against Amgen Patent Application No. 1239-2011 in Chile, papers stamped by the Institution Nacional de Propiedad Industrial on Nov. 17, 2011 (Spanish with English translation).
Patent Examination Report No. 1 for Australian Patent Application No. 2011237541, dated Aug. 10, 2012, 3 pages.
Patent Examination Report No. 2 for Australian Patent Application No. 2011237541, dated Oct. 22, 2012, 2 pages.
Payne, S.J.L., et al., "Influence of the tumor microenvironment on angiogenesis," Future Oncology, 2011, vol. 7, pp. 395-408.
PCT International Search Report and Written Opinion for PCT/US2014/014490, dated Jun. 27, 2014, 20 Pages.
PCT International Search Report and Written Opinion, PCT/US2009/006252, dated Jun. 17, 2010, 15 pages.
PCT Search Report and Written Opinion for PCT/US2008/003119, dated Sep. 6, 2009, 16 Pages.
PCT Search Report and Written Opinion for PCT/US2012/070571, dated Mar. 19, 2013, 12 Pages.
PCT Written Opinion for PCT/US2006/043044, dated Mar. 15, 2007, 6 Pages.
Phillips, A., "The challenge of gene therapy and DNA delivery," Journal of Pharmacy and Pharmacology, Mar. 6, 2001, vol. 53, pp. 1169-1174.
Provencher, DM, et al., "Characterization of four novel epithelial ovarian cancer cell lines," In Vitro Cellular & Developmental Biology Animal, 2000, vol. 36, pp. 357-361.
Rasmussen, et al., "Isolation, characterization and recombinant protein expression in Veggie-CHO: A serum-free CHO host cell line," Cytotechnology, 28:31-42, 1998.
Robertson, D.M., et al., "Inhibin/activin and ovarian cancer," Endocrine-Related Cancer, 2004, pp. 35-49, vol. 11.
Rosenzweig, B., et al., "Cloning and characterization of a human type II receptor for bone morphogenetic proteins," Proc. Natl. Acad. Sci., Aug. 1995, vol. 92, pp. 7632-7636.
Roth, SM, et al., "Myostatin. A therapeutic target for skeletal muscle wasting," Curr Opin Clin Nutr Metab Care. 2004, vol. 7, pp. 259-263.
Roubenoff, R., "Origins and clinical relevance of sarcopenia," Can. J Appl Phys. 2001, vol. 26, pp. 78-89.
Roubenoff, R., et al., "Standardization of nomenclature of body composition in weight loss," Am J Clin Nutr. 1997, vol. 66, pp. 192-196.
Search Report for Gulf Cooperation Council Application No. GCC/P/2008/10291, dated Aug. 10, 2011, 11 Pages.
Second Office Action for Eurasian Patent Application No. EA 200970810/28, dated Nov. 21, 2012, 2 Pages.
Sharma, M., et al., "Myostatin, a Transforming Growth Factor-.beta. Superfamily Member, Is Expressed in Heart Muscle and Is Upregulated in Cardiomyocytes After Infarct," Journal of Cell Physiology, 1999, vol. 180, No. 1, pp. 1-9.
Shou, W., et al., "Role of Androgens in Testicular Tumor Development in Inhibin-Deficient Mice," Endocrinology, 1997, vol. 138 No. 11 pp. 5000-5005.
Sidman, et al., "Controlled Release of Macromolecules and Pharmaceuticals from Synthetic Polypeptides Based on Glutamic Acid," Biopolymers, 22:547-556, 1983.
Songsivilai, et al., "Bispecific antibody: a tool for diagnosis and treatment of disease," Clin. Exp. Immunology, 79:315-321, 1990.
Steller, M.C. et al., "Inhibin Resistance Is Associated with Aggressive Tumorigenicity of Ovarian Cancer Cells," Mol. Cancer Res., 2005, vol. 3, pp. 50-61.
Strassmann, G., et al., "Suramin interferes with interleukin-6 receptor binding in vitro and inhibits colon-26-mediated experimental cancer cachexia in vivo," J Clin Invest, vol. 92, 1993, pp. 2152-2159.
Substantive Examination Report for Malaysian Patent Application No. PI 2011002346, dated May 15, 2015, 4 Pages.
Tam, et al., "S.sub.N2 Deprotection of Synthetic Peptides with a Low Concentration of HF in Dimethyl Sulfide: Evidence and Application in Peptide Synthesis," J. American Chemical Society, 105:6442-6455, 1983.
Thompson, T.B., et al., "Structures of an ActRIIB: activin A complex reveal a novel binding mode for TGF-beta ligand:receptor

(56) References Cited

OTHER PUBLICATIONS interactions" EMBO Journal, Apr. 1, 2003, pp. 1555-1566, vol. 22, No. 7. Can be retrieved at <URL:http://dx.doi.org/10.1093/emboj/cdg156>.

Tobin, J.F., et al., "Myostatin, a negative regulator of muscle mass: implications for muscle degenerative diseases," Current Opinion in Pharmacology, Elsevier Science Publishers, Jun. 2005, vol. 5, No. 3, pp. 328-332.

Tomayko, MM., et al., "Determination of subcutaneous tumor size in athymic (nude) mice," Cancer Chemother Pharmacol. 1989, vol. 24, pp. 148-154.

Tournier, I., et al., "Germline Mutations of Inhibins in Early-Onset Ovarian Epithelial Tumors," Human Mutation, Dec. 2, 2013, pp. 294-297, vol. 35, No. 3.

Urlaub, et al., "Isolation of Chinese hamster cell mutants deficient in dihydrofolate reductase activity," Proc. Natl. Acad. Sci. USA, 77(7):4216-4220, 1980.

Vale, W., et al., "Purification and characterization of an FSH releasing protein from porcine ovarian follicular fluid," Nature, Jun. 1986, vol. 321, 776-779.

Wang, A., et al., "Rapid analysis of gene expression (RAGE) facilitates universal expression profiling," Nucl. Acids Res., 1999, vol. 27, pp. 4609-4618.

Wells, 1990, Biochemistry 29:8509-8517.

Wigley, P., et al., "Site-specific Transgene Insertion: an Approach" Reprod Fertil. Dev., 1994, vol. 6, pp. 585-588.

Wildi, S., et al., Overexpression of activin A in stage IV colorectal cancer, GUT, 2001, pp. 409-417, vol. 49.

Yarasheski, K.E., et al., "Serum myostatin-immunoreactive protein is increased in 60-92 year old women and men with muscle wasting," Journal of Nutrition, Health and Aging, 2002, vol. 6, No. 5, pp. 343-348.

Yen, et al., "Obesity, diabetes, and neoplasia in yellow A.sup.vy /- mice: ectopic expression of the agouti gene," FASEBJ. 8:479-488, 1994.

Yoshinga, K., et al., "Clinical significance of the expression of activin A in esophageal carcinoma," Int J Oncol 2003, vol. 22, pp. 75-80.

Zachwieja, J., et al., "Plasma myostatin-immunoreactive protein is increased after prolonged bed rest with low-dose T.sub.3 Administration," Journal of Gravitational Physiology, Oct. 1999, vol. 6 No. 2, pp. 11-15.

Zhou X, et al., "Reversal of cancer cachexia and muscle wasting by ActRIIB antagonism leads to prolonged survival," Cell, 2010, vol. 142, pp. 531-543.

Zimmers, T., et al., "Induction of Cachexia in Mice by Systemically Administered Myostatin," Science, 2002, vol. 296, pp. 1486-1488.

Notice of Reasons for Rejection for Japanese Patent Application No. JP 2012-171705, dated Oct. 31, 2016, 13 Pages.

Office Action for Chinese Patent Application No. CN 201410462932. 8, dated Nov. 28, 2016, 6 pages, (With Concise Explanation of Relevance).

Office Action for Australian Patent Application No. AU 2012364736, dated Oct. 19, 2016, 3 Pages.

Office Action for Israeli Patent Application No. IL 248128, dated Oct. 5, 2016, 3 Pages, (With Concise Explanation of Relevance).

Office Action for Columbian Patent Application No. CO 11-079. 058, dated Oct. 31, 2016, 12 Pages.

Office Action for U.S. Appl. No. 15/171,944, dated Nov. 9, 2016, 8 Pages.

GenBank AAN76043.1, "immunoglobulin gamma 2 heavy chain constant region, partial [Homo sapiens]," Mar. 21, 2005, NCBI, 2 Pages.

Office Action for Eurasian Patent Application No. 201491231, dated Nov. 25, 2016, 5 Pages.

Office Action for Ukrainian Patent Application No. A 2012 14279, dated Jan. 20, 2017, 11 Pages.

Extended European Search Report for European Patent Application No. EP 16194631.4, dated Jan. 26, 2017, 7 Pages.

Office Action for U.S. Appl. No. 15/171,944, dated Mar. 2, 2017, 8 Pages.

Office Action for U.S. Appl. No. 14/171,670, dated Feb. 17, 2017, 19 Pages.

First Examination Report for New Zealand Patent Application No. 720036, dated May 31, 2016, 3 Pages.

Office Action for Eurasian Patent Application No. 201491231, dated Apr. 20, 2016, 4 Pages.

Office Action for Eurasian Patent Application No. EA 201490822, dated May 5, 2016, 2 Pages (With Concise Explanation of Relevance).

Office Action for Columbian Patent Application No. CO 11-079. 058, dated Apr. 12, 2016, 17 Pages.

Office Action for Columbian Patent Application No. CO 14-143018, dated Apr. 6, 2016, 26 Pages.

Office Action for Chilean Patent Application No. CL 2014-01648, dated Feb. 9, 2016, 18 Pages.

Office Action for Taiwan Patent Application No. TW 103117408, dated Mar. 11, 2016, 5 Pages.

Office Action for Canadian Patent Application No. CA 2,679,841, dated Apr. 26, 2016, 4 Pages.

Office Action for U.S. Appl. No. 14/171,670, dated May 18, 2016, 22 Pages.

Office Action for U.S. Appl. No. 14/626,457, dated May 19, 2016, 7 Pages.

Office Action for U.S. Appl. No. 14/260,856, dated May 9, 2016, 17 Pages.

Office Action for U.S. Appl. No. 14/366,978, dated Mar. 14, 2016, 6 Pages.

Patent Examination Report No. 2 for Australian Patent Application No. 2014210609, dated May 23, 2016, 2 Pages.

Communication Pursuant to Article 94(3) EPC for European Patent Application No. EP 12809999.1, dated Jan. 19, 2016, 4 Pages.

Notice of Reasons for Rejection for Japanese Patent Application No. JP 2014-136375, dated Feb. 15, 2016, 6 Pages.

Patent Examination Report No. 2 for Australian Patent Application No. AU 2013216639, dated Feb. 16, 2016, 2 Pages.

Office Action for Vietnamese Patent Application No. 1-2015-03103, dated Feb. 26, 2016, 2 Pages.

Office Action for Israeli Patent Application No. 240139, dated Feb. 28, 2016, 3 Pages. (With Concise Explanation of Relevance).

NCBI, GenBank: AAN76043.1 "immunoglobulin gamma 2 heavy chain constant region, partial [Homo sapiens]," Mar. 21, 2005, 2 pages, can be retrieved at <URL: http://www.ncbi.nlm.nih.gov/protein/25987833/>.

Communication pursuant to Article 94(3) EPC for European Patent Application No. EP 12809999.1, dated Dec. 22, 2016, 6 Pages.

Office Action for Argentine Published Patent Application No. AR 074397 A1, dated Jan. 9, 2017, 7 Pages.

Office Action for Colombian Patent Application No. 14-143018, dated Dec. 16, 2016, 7 Pages.

Office Action for Mexican Patent Application No. MX/a/2013/012260, dated Nov. 7, 2016, 4 Pages, (With Concise Explanation of Relevance).

Office Action for Chinese Patent Application No. CN 201280070103. 4, dated Dec. 27, 2016, 11 Pages, (With Concise Explanation of Relevance).

Office Action for Chilean Patent Application No. CL 2015-03139, dated Apr. 12, 2017, 8 Pages (With Concise Explanation of Relevance).

Office Action for Eurasian Patent Application No. EA 201490822, dated Apr. 12, 2017, 2 Pages.

Office Action for Colombian Patent Application No. NC2016/0005077, dated May 2, 2017, 3 Pages (With English Summary).

Office Action for Thailand Patent Application No. 1501004361, dated May 1, 2017, 2 Pages.

Office Action for Ukrainian Patent Application No. a 2014 07864, dated May 4, 2017, 9 Pages.

Office Action for U.S. Appl. No. 15/014,889, dated Jun. 15, 2017, 11 Pages.

Office Action for Japanese Patent Application No. JP 2016-092915, dated Mar. 29, 2017, 10 Pages.

(56) References Cited

OTHER PUBLICATIONS

Office Action for Chilean Patent Application No. CL 2015-02166, dated Feb. 13, 2017, 13 Pages.
Office Action for Chilean Patent Application No. CL 2014-01648, dated Feb. 15, 2017, 19 Pages.
Office Action for Peruvian Patent Application No. 002108-2012/DIN, dated Mar. 3, 2017, 17 Pages.
Examination Report No. 2 for Australian Patent Application No. AU 2016210719, dated Mar. 23, 2017, 2 Pages.
Office Action for Argentine Published Patent Application No. AR 065611 A1, dated Mar. 10, 2017, 8 Pages (With English Summary).
Office Action for Taiwan Patent Application No. TW 105129851, dated May 15, 2017, 7 Pages.

SEQUENCE LISTING

```
<160> NUMBER OF SEQ ID NOS: 50

<210> SEQ ID NO 1
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 1 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gag tgc atc tac tac      96
Ala Gly Ser Gly Arg Gly Glu Ala Glu Thr Arg Glu Cys Ile Tyr Tyr
            20                  25                  30 aac gcc aac tgg gag ctg gag cgc acc aac cag agc ggc ctg gag cgc     144
```

```
                Asn Ala Asn Trp Glu Leu Glu Arg Thr Asn Gln Ser Gly Leu Glu Arg
                             35                  40                  45 tgc gaa ggc gag cag gac aag cgg ctg cac tgc tac gcc tcc tgg cgc              192
Cys Glu Gly Glu Gln Asp Lys Arg Leu His Cys Tyr Ala Ser Trp Arg
 50                  55                  60 aac agc tct ggc acc atc gag ctc gtg aag aag ggc tgc tgg cta gat              240
Asn Ser Ser Gly Thr Ile Glu Leu Val Lys Lys Gly Cys Trp Leu Asp
 65                  70                  75                  80 gac ttc aac tgc tac gat agg cag gag tgt gtg gcc act gag gag aac              288
Asp Phe Asn Cys Tyr Asp Arg Gln Glu Cys Val Ala Thr Glu Glu Asn
                     85                  90                  95 ccc cag gtg tac ttc tgc tgt gaa ggc aac ttc tgc aac gag cgc                  336
Pro Gln Val Tyr Phe Cys Cys Glu Gly Asn Phe Cys Asn Glu Arg
                100                 105                 110 ttc act cat ttg cca gag gct ggg ggc ccg gaa gtc acg tac gag cca              384
Phe Thr His Leu Pro Glu Ala Gly Gly Pro Glu Val Thr Tyr Glu Pro
            115                 120                 125 ccc ccg aca gcc ccc acc                                                      402
Pro Pro Thr Ala Pro Thr
        130

<210> SEQ ID NO 2
<211> LENGTH: 134
<212> TYPE: PRT
<213> ORGANISM: Homo sapiens

<400> SEQUENCE: 2

Met Thr Ala Pro Trp Val Ala Leu Ala Leu Leu Trp Gly Ser Leu Cys
 1               5                  10                  15

Ala Gly Ser Gly Arg Gly Glu Ala Glu Thr Arg Glu Cys Ile Tyr Tyr
                 20                  25                  30

Asn Ala Asn Trp Glu Leu Glu Arg Thr Asn Gln Ser Gly Leu Glu Arg
                 35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                     85                  90                  95

Pro Gln Val Tyr Phe Cys Cys Glu Gly Asn Phe Cys Asn Glu Arg
                100                 105                 110

Phe Thr His Leu Pro Glu Ala Gly Gly Pro Glu Val Thr Tyr Glu Pro
            115                 120                 125

Pro Pro Thr Ala Pro Thr
        130

<210> SEQ ID NO 3
<211> LENGTH: 387
<212> TYPE: DNA
<213> ORGANISM: Homo sapiens
<220> FEATURE:
<221> NAME/KEY: CDS
<222> LOCATION: (1)..(387)

<400> SEQUENCE: 3 atg gag ttt ggg ctg agc tgg gtt ttc ctc gtt gct ctt tta aga ggt               48
Met Glu Phe Gly Leu Ser Trp Val Phe Leu Val Ala Leu Leu Arg Gly
 1               5                  10                  15 gtc cag tgt gag aca cgg tgg tgc atc tac tac aac gcc aac tgg gag               96
Val Gln Cys Glu Thr Arg Trp Cys Ile Tyr Tyr Asn Ala Asn Trp Glu
```

```
                 20                  25                  30
ctg gag cgc acc aac cag acc ggc ctg gag cgc tgc gaa ggc gag cag     144
Leu Glu Arg Thr Asn Gln Thr Gly Leu Glu Arg Cys Glu Gly Glu Gln
         35                  40                  45 gac aag cgg ctg cac tgc tac gcc tcc tgg cgc aac agc tct ggc acc     192
Asp Lys Arg Leu His Cys Tyr Ala Ser Trp Arg Asn Ser Ser Gly Thr
 50                  55                  60 atc gag ctc gtg aag aag ggc tgc tgg cta gat gac ttc aac tgc tac     240
Ile Glu Leu Val Lys Lys Gly Cys Trp Leu Asp Asp Phe Asn Cys Tyr
 65                  70                  75                  80 gat agg cag gag tgt gtg gcc act gag gag aac ccc cag gtg tac ttc     288
Asp Arg Gln Glu Cys Val Ala Thr Glu Glu Asn Pro Gln Val Tyr Phe
                 85                  90                  95 tgc tgc tgt gag ggc aac ttc tgc aac gag cgc ttc act cat ttg cca     336
Cys Cys Cys Glu Gly Asn Phe Cys Asn Glu Arg Phe Thr His Leu Pro
             100                 105                 110 gag gct ggg ggc ccg gaa gtc acg tac gag cca ccc ccg aca gcc ccc     384
Glu Ala Gly Gly Pro Glu Val Thr Tyr Glu Pro Pro Pro Thr Ala Pro
         115                 120                 125 acc                                                                  387
Thr

<210> SEQ ID NO 4
<211> LENGTH: 129
<212> TYPE: PRT
<213> ORGANISM: Homo sapiens

<400> SEQUENCE: 4

Met Glu Phe Gly Leu Ser Trp Val Phe Leu Val Ala Leu Leu Arg Gly
 1               5                  10                  15

Val Gln Cys Glu Thr Arg Trp Cys Ile Tyr Tyr Asn Ala Asn Trp Glu
                 20                  25                  30

Leu Glu Arg Thr Asn Gln Thr Gly Leu Glu Arg Cys Glu Gly Glu Gln
         35                  40                  45

Asp Lys Arg Leu His Cys Tyr Ala Ser Trp Arg Asn Ser Ser Gly Thr
 50                  55                  60

Ile Glu Leu Val Lys Lys Gly Cys Trp Leu Asp Asp Phe Asn Cys Tyr
 65                  70                  75                  80

Asp Arg Gln Glu Cys Val Ala Thr Glu Glu Asn Pro Gln Val Tyr Phe
                 85                  90                  95

Cys Cys Cys Glu Gly Asn Phe Cys Asn Glu Arg Phe Thr His Leu Pro
             100                 105                 110

Glu Ala Gly Gly Pro Glu Val Thr Tyr Glu Pro Pro Pro Thr Ala Pro
         115                 120                 125

Thr

<210> SEQ ID NO 5
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 5 gag aca cgg tgg tgc atc tac tac aac gcc aac tgg gag ctg gag cgc      48
Glu Thr Arg Trp Cys Ile Tyr Tyr Asn Ala Asn Trp Glu Leu Glu Arg
 1               5                  10                  15 acc aac cag acc ggc ctg gag cgc tgc gaa ggc gag cag gac aag cgg      96
Thr Asn Gln Thr Gly Leu Glu Arg Cys Glu Gly Glu Gln Asp Lys Arg
```

```
        Thr Asn Gln Thr Gly Leu Glu Arg Cys Glu Gly Glu Gln Asp Lys Arg
                     20                  25                  30 ctg cac tgc tac gcc tcc tgg cgc aac agc tct ggc acc atc gag ctc      144
Leu His Cys Tyr Ala Ser Trp Arg Asn Ser Ser Gly Thr Ile Glu Leu
             35                  40                  45 gtg aag aag ggc tgc tgg cta gat gac ttc aac tgc tac gat agg cag      192
Val Lys Lys Gly Cys Trp Leu Asp Asp Phe Asn Cys Tyr Asp Arg Gln
 50                  55                  60 gag tgt gtg gcc act gag gag aac ccc cag gtg tac ttc tgc tgt          240
Glu Cys Val Ala Thr Glu Glu Asn Pro Gln Val Tyr Phe Cys Cys
 65                  70                  75                  80 gag ggc aac ttc tgc aac gag cgc ttc act cat ttg cca gag gct ggg      288
Glu Gly Asn Phe Cys Asn Glu Arg Phe Thr His Leu Pro Glu Ala Gly
                 85                  90                  95 ggc ccg gaa gtc acg tac gag cca ccc ccg aca gcc ccc acc              330
Gly Pro Glu Val Thr Tyr Glu Pro Pro Pro Thr Ala Pro Thr
            100                 105                 110

<210> SEQ ID NO 6
<211> LENGTH: 110
<212> TYPE: PRT
<213> ORGANISM: Homo sapiens

<400> SEQUENCE: 6

Glu Thr Arg Trp Cys Ile Tyr Tyr Asn Ala Asn Trp Glu Leu Glu Arg
 1               5                  10                  15

Thr Asn Gln Thr Gly Leu Glu Arg Cys Glu Gly Glu Gln Asp Lys Arg
                 20                  25                  30

Leu His Cys Tyr Ala Ser Trp Arg Asn Ser Ser Gly Thr Ile Glu Leu
             35                  40                  45

Val Lys Lys Gly Cys Trp Leu Asp Asp Phe Asn Cys Tyr Asp Arg Gln
 50                  55                  60

Glu Cys Val Ala Thr Glu Glu Asn Pro Gln Val Tyr Phe Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Pro Thr Ala Pro Thr
            100                 105                 110

<210> SEQ ID NO 7
<211> LENGTH: 1071
<212> TYPE: DNA
<213> ORGANISM: Homo sapiens
<220> FEATURE:
<221> NAME/KEY: CDS
<222> LOCATION: (1)..(1071)

<400> SEQUENCE: 7 atg gag ttt ggg ctg agc tgg gtt ttc ctc gtt gct ctt tta aga ggt      48
Met Glu Phe Gly Leu Ser Trp Val Phe Leu Val Ala Leu Leu Arg Gly
 1               5                  10                  15 gtc cag tgt gag aca cgg tgg tgc atc tac tac aac gcc aac tgg gag      96
Val Gln Cys Glu Thr Arg Trp Cys Ile Tyr Tyr Asn Ala Asn Trp Glu
                 20                  25                  30 ctg gag cgc acc aac cag acc ggc ctg gag cgc tgc gaa ggc gag cag     144
Leu Glu Arg Thr Asn Gln Thr Gly Leu Glu Arg Cys Glu Gly Glu Gln
             35                  40                  45 gac aag cgg ctg cac tgc tac gcc tcc tgg cgc aac agc tct ggc acc     192
Asp Lys Arg Leu His Cys Tyr Ala Ser Trp Arg Asn Ser Ser Gly Thr
 50                  55                  60
```

```
atc gag ctc gtg aag aag ggc tgc tgg cta gat gac ttc aac tgc tac       240
Ile Glu Leu Val Lys Lys Gly Cys Trp Leu Asp Asp Phe Asn Cys Tyr
65                  70                  75                  80 gat agg cag gag tgt gtg gcc act gag gag aac ccc cag gtg tac ttc       288
Asp Arg Gln Glu Cys Val Ala Thr Glu Glu Asn Pro Gln Val Tyr Phe
                85                  90                  95 tgc tgc tgt gag ggc aac ttc tgc aac gag cgc ttc act cat ttg cca       336
Cys Cys Cys Glu Gly Asn Phe Cys Asn Glu Arg Phe Thr His Leu Pro
            100                 105                 110 gag gct ggg ggc ccg gaa gtc acg tac gag cca ccc ccg aca gcc ccc       384
Glu Ala Gly Gly Pro Glu Val Thr Tyr Glu Pro Pro Pro Thr Ala Pro
        115                 120                 125 acc gga ggg gga gga tct gtc gag tgc cca ccg tgc cca gca cca cct       432
Thr Gly Gly Gly Gly Ser Val Glu Cys Pro Pro Cys Pro Ala Pro Pro
    130                 135                 140 gtg gca gga ccg tca gtc ttc ctc ttc ccc cca aaa ccc aag gac acc       480
Val Ala Gly Pro Ser Val Phe Leu Phe Pro Pro Lys Pro Lys Asp Thr
145                 150                 155                 160 ctc atg atc tcc cgg acc cct gag gtc acg tgc gtg gtg gtg gac gtg       528
Leu Met Ile Ser Arg Thr Pro Glu Val Thr Cys Val Val Val Asp Val
                165                 170                 175 agc cac gaa gac ccc gag gtc cag ttc aac tgg tac gtg gac ggc gtg       576
Ser His Glu Asp Pro Glu Val Gln Phe Asn Trp Tyr Val Asp Gly Val
            180                 185                 190 gag gtg cat aat gcc aag aca aag cca cgg gag gag cag ttc aac agc       624
Glu Val His Asn Ala Lys Thr Lys Pro Arg Glu Glu Gln Phe Asn Ser
        195                 200                 205 acg ttc cgt gtg gtc agc gtc ctc acc gtt gtg cac cag gac tgg ctg       672
Thr Phe Arg Val Val Ser Val Leu Thr Val Val His Gln Asp Trp Leu
    210                 215                 220 aac ggc aag gag tac aag tgc aag gtc tcc aac aaa ggc ctc cca gcc       720
Asn Gly Lys Glu Tyr Lys Cys Lys Val Ser Asn Lys Gly Leu Pro Ala
225                 230                 235                 240 ccc atc gag aaa acc atc tcc aaa acc aaa ggg cag ccc cga gaa cca       768
Pro Ile Glu Lys Thr Ile Ser Lys Thr Lys Gly Gln Pro Arg Glu Pro
                245                 250                 255 cag gtg tac acc ctg ccc cca tcc cgg gag gag atg acc aag aac cag       816
Gln Val Tyr Thr Leu Pro Pro Ser Arg Glu Glu Met Thr Lys Asn Gln
            260                 265                 270 gtc agc ctg acc tgc ctg gtc aaa ggc ttc tat ccc agc gac atc gcc       864
Val Ser Leu Thr Cys Leu Val Lys Gly Phe Tyr Pro Ser Asp Ile Ala
        275                 280                 285 gtg gag tgg gag agc aat ggg cag ccg gag aac aac tac aag acc aca       912
Val Glu Trp Glu Ser Asn Gly Gln Pro Glu Asn Asn Tyr Lys Thr Thr
    290                 295                 300 cct ccc atg ctg gac tcc gac ggc tcc ttc ttc ctc tac agc aag ctc       960
Pro Pro Met Leu Asp Ser Asp Gly Ser Phe Phe Leu Tyr Ser Lys Leu
305                 310                 315                 320 acc gtg gac aag agc agg tgg cag cag ggg aac gtc ttc tca tgc tcc      1008
Thr Val Asp Lys Ser Arg Trp Gln Gln Gly Asn Val Phe Ser Cys Ser
                325                 330                 335 gtg atg cat gag gct ctg cac aac cac tac acg cag aag agc ctc tcc      1056
Val Met His Glu Ala Leu His Asn His Tyr Thr Gln Lys Ser Leu Ser
            340                 345                 350 ctg tct ccg ggt aaa                                                  1071
Leu Ser Pro Gly Lys
        355

<210> SEQ ID NO 8
<211> LENGTH: 357
```

<212> TYPE: PRT
<213> ORGANISM: Homo sapiens

<400> SEQUENCE: 8

Met Glu Phe Gly Leu Ser Trp Val Phe Leu Val Ala Leu Leu Arg Gly
1               5                   10                  15

Val Gln Cys Glu Thr Arg Trp Cys Ile Tyr Tyr Asn Ala Asn Trp Glu
            20                  25                  30

Leu Glu Arg Thr Asn Gln Thr Gly Leu Glu Arg Cys Glu Gly Glu Gln
        35                  40                  45

Asp Lys Arg Leu His Cys Tyr Ala Ser Trp Arg Asn Ser Ser Gly Thr
    50                  55                  60

Ile Glu Leu Val Lys Lys Gly Cys Trp Leu Asp Asp Phe Asn Cys Tyr
65                  70                  75                  80

Asp Arg Gln Glu Cys Val Ala Thr Glu Glu Asn Pro Gln Val Tyr Phe
                85                  90                  95

Cys Cys Cys Glu Gly Asn Phe Cys Asn Glu Arg Phe Thr His Leu Pro
            100                 105                 110

Glu Ala Gly Gly Pro Glu Val Thr Tyr Glu Pro Pro Thr Ala Pro
        115                 120                 125

Thr Gly Gly Gly Ser Val Glu Cys Pro Pro Cys Pro Ala Pro Pro
    130                 135                 140

Val Ala Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Gln Phe Asn Trp Tyr Val Asp Gly Val
            180                 185                 190

Glu Val His Asn Ala Lys Thr Lys Pro Arg Glu Glu Gln Phe Asn Ser
        195                 200                 205

Thr Phe Arg Val Val Ser Val Leu Thr Val Val His Gln Asp Trp Leu
    210                 215                 220

Asn Gly Lys Glu Tyr Lys Cys Lys Val Ser Asn Lys Gly Leu Pro Ala
225                 230                 235                 240

Pro Ile Glu Lys Thr Ile Ser Lys Thr Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Met Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 9
<211> LENGTH: 1014
<212> TYPE: DNA
<213> ORGANISM: Homo sapiens

```
<220> FEATURE:
<221> NAME/KEY: CDS
<222> LOCATION: (1)..(1014)

<400> SEQUENCE: 9 gag aca cgg tgg tgc atc tac tac aac gcc aac tgg gag ctg gag cgc      48
Glu Thr Arg Trp Cys Ile Tyr Tyr Asn Ala Asn Trp Glu Leu Glu Arg
1               5                   10                  15 acc aac cag acc ggc ctg gag cgc tgc gaa ggc gag cag gac aag cgg      96
Thr Asn Gln Thr Gly Leu Glu Arg Cys Glu Gly Glu Gln Asp Lys Arg
            20                  25                  30 ctg cac tgc tac gcc tcc tgg cgc aac agc tct ggc acc atc gag ctc     144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag     192
Val Lys Lys Gly Cys Trp Leu Asp Asp Phe Asn Cys Tyr Asp Arg Gln
    50                  55                  60 gag tgt gtg gcc act gag gag aac ccc cag gtg tac ttc tgc tgc tgt     240
Glu Cys Val Ala Thr Glu Glu Asn Pro Gln Val Tyr Phe Cys Cys Cys
65                  70                  75                  80 gag ggc aac ttc tgc aac gag cgc ttc act cat ttg cca gag gct ggg     288
Glu Gly Asn Phe Cys Asn Glu Arg Phe Thr His Leu Pro Glu Ala Gly
                85                  90                  95 ggc ccg gaa gtc acg tac gag cca ccc ccg aca gcc ccc acc gga ggg     336
Gly Pro Glu Val Thr Tyr Glu Pro Pro Pro Thr Ala Pro Thr Gly Gly
            100                 105                 110 gga gga tct gtc gag tgc cca ccg tgc cca gca cca cct gtg gca gga     384
Gly Gly Ser Val Glu Cys Pro Pro Cys Pro Ala Pro Pro Val Ala Gly
        115                 120                 125 ccg tca gtc ttc ctc ttc ccc cca aaa ccc aag gac acc ctc atg atc     432
Pro Ser Val Phe Leu Phe Pro Pro Lys Pro Lys Asp Thr Leu Met Ile
    130                 135                 140 tcc cgg acc cct gag gtc acg tgc gtg gtg gtg gac gtg agc cac gaa     480
Ser Arg Thr Pro Glu Val Thr Cys Val Val Val Asp Val Ser His Glu
145                 150                 155                 160 gac ccc gag gtc cag ttc aac tgg tac gtg gac ggc gtg gag gtg cat     528
Asp Pro Glu Val Gln Phe Asn Trp Tyr Val Asp Gly Val Glu Val His
                165                 170                 175 aat gcc aag aca aag cca cgg gag gag cag ttc aac agc acg ttc cgt     576
Asn Ala Lys Thr Lys Pro Arg Glu Glu Gln Phe Asn Ser Thr Phe Arg
            180                 185                 190 gtg gtc agc gtc ctc acc gtt gtg cac cag gac tgg ctg aac ggc aag     624
Val Val Ser Val Leu Thr Val Val His Gln Asp Trp Leu Asn Gly Lys
        195                 200                 205 gag tac aag tgc aag gtc tcc aac aaa ggc ctc cca gcc ccc atc gag     672
Glu Tyr Lys Cys Lys Val Ser Asn Lys Gly Leu Pro Ala Pro Ile Glu
    210                 215                 220 aaa acc atc tcc aaa acc aaa ggg cag ccc cga gaa cca cag gtg tac     720
Lys Thr Ile Ser Lys Thr Lys Gly Gln Pro Arg Glu Pro Gln Val Tyr
225                 230                 235                 240 acc ctg ccc cca tcc cgg gag gag atg acc aag aac cag gtc agc ctg     768
Thr Leu Pro Pro Ser Arg Glu Glu Met Thr Lys Asn Gln Val Ser Leu
                245                 250                 255 acc tgc ctg gtc aaa ggc ttc tat ccc agc gac atc gcc gtg gag tgg     816
Thr Cys Leu Val Lys Gly Phe Tyr Pro Ser Asp Ile Ala Val Glu Trp
            260                 265                 270 gag agc aat ggg cag ccg gag aac aac tac aag acc aca cct ccc atg     864
Glu Ser Asn Gly Gln Pro Glu Asn Asn Tyr Lys Thr Thr Pro Pro Met
        275                 280                 285 ctg gac tcc gac ggc tcc ttc ttc ctc tac agc aag ctc acc gtg gac     912
Leu Asp Ser Asp Gly Ser Phe Phe Leu Tyr Ser Lys Leu Thr Val Asp
```

```
Leu Asp Ser Asp Gly Ser Phe Phe Leu Tyr Ser Lys Leu Thr Val Asp
    290             295                 300 aag agc agg tgg cag cag ggg aac gtc ttc tca tgc tcc gtg atg cat    960
Lys Ser Arg Trp Gln Gln Gly Asn Val Phe Ser Cys Ser Val Met His
305             310                 315                 320 gag gct ctg cac aac cac tac acg cag aag agc ctc tcc ctg tct ccg    1008
Glu Ala Leu His Asn His Tyr Thr Gln Lys Ser Leu Ser Leu Ser Pro
                325                 330                 335 ggt aaa                                                             1014
Gly Lys <210> SEQ ID NO 10
<211> LENGTH: 338
<212> TYPE: PRT
<213> ORGANISM: Homo sapiens

<400> SEQUENCE: 10

Glu Thr Arg Trp Cys Ile Tyr Tyr Asn Ala Asn Trp Glu Leu Glu Arg
1               5                   10                  15

Thr Asn Gln Thr Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr Gly Gly
            100                 105                 110

Gly Gly Ser Val Glu Cys Pro Pro Cys Pro Ala Pro Pro Val Ala Gly
        115                 120                 125

Pro Ser Val Phe Leu Phe Pro Pro Lys Pro Lys Asp Thr Leu Met Ile
130                 135                 140

Ser Arg Thr Pro Glu Val Thr Cys Val Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Met
        275                 280                 285

Leu Asp Ser Asp Gly Ser Phe Phe Leu Tyr Ser Lys Leu Thr Val Asp
    290                 295                 300
```

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
            325                 330                 335

Gly Lys

<210> SEQ ID NO 11
<211> LENGTH: 387
<212> TYPE: DNA
<213> ORGANISM: Homo sapiens
<220> FEATURE:
<221> NAME/KEY: CDS
<222> LOCATION: (1)..(387)

<400> SEQUENCE: 11

```
atg gag ttt ggg ctg agc tgg gtt ttc ctc gtt gct ctt tta aga ggt      48
Met Glu Phe Gly Leu Ser Trp Val Phe Leu Val Ala Leu Leu Arg Gly
1               5                   10                  15 gtc cag tgt gag aca cgg tac tgc atc tac tac aac gcc aac tgg gag      96
Val Gln Cys Glu Thr Arg Tyr Cys Ile Tyr Tyr Asn Ala Asn Trp Glu
                20                  25                  30 ctg gag cgc acc aac cag acc ggc ctg gag cgc tgc gaa ggc gag cag     144
Leu Glu Arg Thr Asn Gln Thr Gly Leu Glu Arg Cys Glu Gly Glu Gln
            35                  40                  45 gac aag cgg ctg cac tgc tac gcc tcc tgg cgc aac agc tct ggc acc     192
Asp Lys Arg Leu His Cys Tyr Ala Ser Trp Arg Asn Ser Ser Gly Thr
        50                  55                  60 atc gag ctc gtg aag aag ggc tgc tgg cta gat gac ttc aac tgc tac     240
Ile Glu Leu Val Lys Lys Gly Cys Trp Leu Asp Asp Phe Asn Cys Tyr
65                  70                  75                  80 gat agg cag gag tgt gtg gcc act gag gag aac ccc cag gtg tac ttc     288
Asp Arg Gln Glu Cys Val Ala Thr Glu Glu Asn Pro Gln Val Tyr Phe
                85                  90                  95 tgc tgc tgt gag ggc aac ttc tgc aac gag cgc ttc act cat ttg cca     336
Cys Cys Cys Glu Gly Asn Phe Cys Asn Glu Arg Phe Thr His Leu Pro
            100                 105                 110 gag gct ggg ggc ccg gaa gtc acg tac gag cca ccc ccg aca gcc ccc     384
Glu Ala Gly Gly Pro Glu Val Thr Tyr Glu Pro Pro Pro Thr Ala Pro
        115                 120                 125 acc                                                                 387
Thr
```

<210> SEQ ID NO 12
<211> LENGTH: 129
<212> TYPE: PRT
<213> ORGANISM: Homo sapiens

<400> SEQUENCE: 12

Met Glu Phe Gly Leu Ser Trp Val Phe Leu Val Ala Leu Leu Arg Gly
1               5                   10                  15

Val Gln Cys Glu Thr Arg Tyr Cys Ile Tyr Tyr Asn Ala Asn Trp Glu
                20                  25                  30

Leu Glu Arg Thr Asn Gln Thr Gly Leu Glu Arg Cys Glu Gly Glu Gln
            35                  40                  45

Asp Lys Arg Leu His Cys Tyr Ala Ser Trp Arg Asn Ser Ser Gly Thr
        50                  55                  60

Ile Glu Leu Val Lys Lys Gly Cys Trp Leu Asp Asp Phe Asn Cys Tyr
65                  70                  75                  80

Asp Arg Gln Glu Cys Val Ala Thr Glu Glu Asn Pro Gln Val Tyr Phe
                85                  90                  95

```
Cys Cys Cys Glu Gly Asn Phe Cys Asn Glu Arg Phe Thr His Leu Pro
            100                 105                 110

Glu Ala Gly Gly Pro Glu Val Thr Tyr Glu Pro Pro Thr Ala Pro
        115                 120                 125

Thr

<210> SEQ ID NO 13
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 13 gag aca cgg tac tgc atc tac tac aac gcc aac tgg gag ctg gag cgc      48
Glu Thr Arg Tyr Cys Ile Tyr Tyr Asn Ala Asn Trp Glu Leu Glu Arg
1               5                   10                  15 acc aac cag acc ggc ctg gag cgc tgc gaa ggc gag cag gac aag cgg      96
Thr Asn Gln Thr Gly Leu Glu Arg Cys Glu Gly Glu Gln Asp Lys Arg
            20                  25                  30 ctg cac tgc tac gcc tcc tgg cgc aac agc tct ggc acc atc gag ctc     144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag     192
Val Lys Lys Gly Cys Trp Leu Asp Asp Phe Asn Cys Tyr Asp Arg Gln
    50                  55                  60 gag tgt gtg gcc act gag gag aac ccc cag gtg tac ttc tgc tgc tgt     240
Glu Cys Val Ala Thr Glu Glu Asn Pro Gln Val Tyr Phe Cys Cys Cys
65                  70                  75                  80 gag ggc aac ttc tgc aac gag cgc ttc act cat ttg cca gag gct ggg     288
Glu Gly Asn Phe Cys Asn Glu Arg Phe Thr His Leu Pro Glu Ala Gly
                85                  90                  95 ggc ccg gaa gtc acg tac gag cca ccc ccg aca gcc ccc acc              330
Gly Pro Glu Val Thr Tyr Glu Pro Pro Pro Thr Ala Pro Thr
            100                 105                 110

<210> SEQ ID NO 14
<211> LENGTH: 110
<212> TYPE: PRT
<213> ORGANISM: Homo sapiens

<400> SEQUENCE: 14

Glu Thr Arg Tyr Cys Ile Tyr Tyr Asn Ala Asn Trp Glu Leu Glu Arg
1               5                   10                  15

Thr Asn Gln Thr Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr
            100                 105                 110

<210> SEQ ID NO 15
```

```
<211> LENGTH: 1071
<212> TYPE: DNA
<213> ORGANISM: Homo sapiens
<220> FEATURE:
<221> NAME/KEY: CDS
<222> LOCATION: (1)..(1071)

<400> SEQUENCE: 15 atg gag ttt ggg ctg agc tgg gtt ttc ctc gtt gct ctt tta aga ggt        48
Met Glu Phe Gly Leu Ser Trp Val Phe Leu Val Ala Leu Leu Arg Gly
1               5                   10                  15 gtc cag tgt gag aca cgg tac tgc atc tac tac aac gcc aac tgg gag        96
Val Gln Cys Glu Thr Arg Tyr Cys Ile Tyr Tyr Asn Ala Asn Trp Glu
                20                  25                  30 ctg gag cgc acc aac cag acc ggc ctg gag cgc tgc gaa ggc gag cag       144
Leu Glu Arg Thr Asn Gln Thr Gly Leu Glu Arg Cys Glu Gly Glu Gln
            35                  40                  45 gac aag cgg ctg cac tgc tac gcc tcc tgg cgc aac agc tct ggc acc       192
Asp Lys Arg Leu His Cys Tyr Ala Ser Trp Arg Asn Ser Ser Gly Thr
        50                  55                  60 atc gag ctc gtg aag aag ggc tgc tgg cta gat gac ttc aac tgc tac       240
Ile Glu Leu Val Lys Lys Gly Cys Trp Leu Asp Asp Phe Asn Cys Tyr
65                  70                  75                  80 gat agg cag gag tgt gtg gcc act gag gag aac ccc cag gtg tac ttc       288
Asp Arg Gln Glu Cys Val Ala Thr Glu Glu Asn Pro Gln Val Tyr Phe
                85                  90                  95 tgc tgc tgt gag ggc aac ttc tgc aac gag cgc ttc act cat ttg cca       336
Cys Cys Cys Glu Gly Asn Phe Cys Asn Glu Arg Phe Thr His Leu Pro
                100                 105                 110 gag gct ggg ggc ccg gaa gtc acg tac gag cca ccc ccg aca gcc ccc       384
Glu Ala Gly Gly Pro Glu Val Thr Tyr Glu Pro Pro Pro Thr Ala Pro
            115                 120                 125 acc gga ggg gga gga tct gtc gag tgc cca ccg tgc cca gca cca cct       432
Thr Gly Gly Gly Gly Ser Val Glu Cys Pro Pro Cys Pro Ala Pro Pro
        130                 135                 140 gtg gca gga ccg tca gtc ttc ctc ttc ccc cca aaa ccc aag gac acc       480
Val Ala Gly Pro Ser Val Phe Leu Phe Pro Pro Lys Pro Lys Asp Thr
145                 150                 155                 160 ctc atg atc tcc cgg acc cct gag gtc acg tgc gtg gtg gtg gac gtg       528
Leu Met Ile Ser Arg Thr Pro Glu Val Thr Cys Val Val Val Asp Val
                165                 170                 175 agc cac gaa gac ccc gag gtc cag ttc aac tgg tac gtg gac ggc gtg       576
Ser His Glu Asp Pro Glu Val Gln Phe Asn Trp Tyr Val Asp Gly Val
                180                 185                 190 gag gtg cat aat gcc aag aca aag cca cgg gag gag cag ttc aac agc       624
Glu Val His Asn Ala Lys Thr Lys Pro Arg Glu Glu Gln Phe Asn Ser
            195                 200                 205 acg ttc cgt gtg gtc agc gtc ctc acc gtt gtg cac cag gac tgg ctg       672
Thr Phe Arg Val Val Ser Val Leu Thr Val Val His Gln Asp Trp Leu
        210                 215                 220 aac ggc aag gag tac aag tgc aag gtc tcc aac aaa ggc ctc cca gcc       720
Asn Gly Lys Glu Tyr Lys Cys Lys Val Ser Asn Lys Gly Leu Pro Ala
225                 230                 235                 240 ccc atc gag aaa acc atc tcc aaa acc aaa ggg cag ccc cga gaa cca       768
Pro Ile Glu Lys Thr Ile Ser Lys Thr Lys Gly Gln Pro Arg Glu Pro
                245                 250                 255 cag gtg tac acc ctg ccc cca tcc cgg gag gag atg acc aag aac cag       816
Gln Val Tyr Thr Leu Pro Pro Ser Arg Glu Glu Met Thr Lys Asn Gln
                260                 265                 270 gtc agc ctg acc tgc ctg gtc aaa ggc ttc tat ccc agc gac atc gcc       864
Val Ser Leu Thr Cys Leu Val Lys Gly Phe Tyr Pro Ser Asp Ile Ala
```

```
                    275                 280                 285
gtg gag tgg gag agc aat ggg cag ccg gag aac aac tac aag acc aca      912
Val Glu Trp Glu Ser Asn Gly Gln Pro Glu Asn Asn Tyr Lys Thr Thr
290                 295                 300 cct ccc atg ctg gac tcc gac ggc tcc ttc ttc ctc tac agc aag ctc      960
Pro Pro Met Leu Asp Ser Asp Gly Ser Phe Phe Leu Tyr Ser Lys Leu
305                 310                 315                 320 acc gtg gac aag agc agg tgg cag cag ggg aac gtc ttc tca tgc tcc     1008
Thr Val Asp Lys Ser Arg Trp Gln Gln Gly Asn Val Phe Ser Cys Ser
            325                 330                 335 gtg atg cat gag gct ctg cac aac cac tac acg cag aag agc ctc tcc     1056
Val Met His Glu Ala Leu His Asn His Tyr Thr Gln Lys Ser Leu Ser
340                 345                 350 ctg tct ccg ggt aaa                                                  1071
Leu Ser Pro Gly Lys
            355
```

<210> SEQ ID NO 16
<211> LENGTH: 357
<212> TYPE: PRT
<213> ORGANISM: Homo sapiens

<400> SEQUENCE: 16

```
Met Glu Phe Gly Leu Ser Trp Val Phe Leu Val Ala Leu Leu Arg Gly
1               5                   10                  15

Val Gln Cys Glu Thr Arg Tyr Cys Ile Tyr Tyr Asn Ala Asn Trp Glu
            20                  25                  30

Leu Glu Arg Thr Asn Gln Thr Gly Leu Glu Arg Cys Glu Gly Glu Gln
        35                  40                  45

Asp Lys Arg Leu His Cys Tyr Ala Ser Trp Arg Asn Ser Ser Gly Thr
    50                  55                  60

Ile Glu Leu Val Lys Lys Gly Cys Trp Leu Asp Asp Phe Asn Cys Tyr
65                  70                  75                  80

Asp Arg Gln Glu Cys Val Ala Thr Glu Glu Asn Pro Gln Val Tyr Phe
                85                  90                  95

Cys Cys Cys Glu Gly Asn Phe Cys Asn Glu Arg Phe Thr His Leu Pro
            100                 105                 110

Glu Ala Gly Gly Pro Glu Val Thr Tyr Glu Pro Pro Thr Ala Pro Thr
        115                 120                 125

Thr Gly Gly Gly Gly Ser Val Glu Cys Pro Pro Cys Pro Ala Pro Pro
    130                 135                 140

Val Ala Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Gln Phe Asn Trp Tyr Val Asp Gly Val
            180                 185                 190

Glu Val His Asn Ala Lys Thr Lys Pro Arg Glu Glu Gln Phe Asn Ser
        195                 200                 205

Thr Phe Arg Val Val Ser Val Leu Thr Val Val His Gln Asp Trp Leu
    210                 215                 220

Asn Gly Lys Glu Tyr Lys Cys Lys Val Ser Asn Lys Gly Leu Pro Ala
225                 230                 235                 240

Pro Ile Glu Lys Thr Ile Ser Lys Thr Lys Gly Gln Pro Arg Glu Pro
                245                 250                 255

Gln Val Tyr Thr Leu Pro Pro Ser Arg Glu Glu Met Thr Lys Asn Gln
```

```
                      260                 265                 270
Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
        290                 295                 300

Pro Pro Met Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 17
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 17
```

| | | | | | | | | | | | | | | | | |
|---|---|---|---|---|---|---|---|---|---|---|---|---|---|---|---|---|
| gag | aca | cgg | tac | tgc | atc | tac | tac | aac | gcc | aac | tgg | gag | ctg | gag | cgc | 48 |
| Glu | Thr | Arg | Tyr | Cys | Ile | Tyr | Tyr | Asn | Ala | Asn | Trp | Glu | Leu | Glu | Arg | |
| 1 | | | | 5 | | | | | 10 | | | | | 15 | | |
| acc | aac | cag | acc | ggc | ctg | gag | cgc | tgc | gaa | ggc | gag | cag | gac | aag | cgg | 96 |
| Thr | Asn | Gln | Thr | Gly | Leu | Glu | Arg | Cys | Glu | Gly | Glu | Gln | Asp | Lys | Arg | |
| | | | 20 | | | | | 25 | | | | | 30 | | | |
| ctg | cac | tgc | tac | gcc | tcc | tgg | cgc | aac | agc | tct | ggc | acc | atc | gag | ctc | 144 |
| Leu | His | Cys | Tyr | Ala | Ser | Trp | Arg | Asn | Ser | Ser | Gly | Thr | Ile | Glu | Leu | |
| | | 35 | | | | | 40 | | | | | 45 | | | | |
| gtg | aag | aag | ggc | tgc | tgg | cta | gat | gac | ttc | aac | tgc | tac | gat | agg | cag | 192 |
| Val | Lys | Lys | Gly | Cys | Trp | Leu | Asp | Asp | Phe | Asn | Cys | Tyr | Asp | Arg | Gln | |
| 50 | | | | | 55 | | | | | 60 | | | | | | |
| gag | tgt | gtg | gcc | act | gag | gag | aac | ccc | cag | gtg | tac | ttc | tgc | tgc | tgt | 240 |
| Glu | Cys | Val | Ala | Thr | Glu | Glu | Asn | Pro | Gln | Val | Tyr | Phe | Cys | Cys | Cys | |
| 65 | | | | | 70 | | | | | 75 | | | | | 80 | |
| gag | ggc | aac | ttc | tgc | aac | gag | cgc | ttc | act | cat | ttg | cca | gag | gct | ggg | 288 |
| Glu | Gly | Asn | Phe | Cys | Asn | Glu | Arg | Phe | Thr | His | Leu | Pro | Glu | Ala | Gly | |
| | | | | 85 | | | | | 90 | | | | | 95 | | |
| ggc | ccg | gaa | gtc | acg | tac | gag | cca | ccc | ccg | aca | gcc | ccc | acc | gga | ggg | 336 |
| Gly | Pro | Glu | Val | Thr | Tyr | Glu | Pro | Pro | Pro | Thr | Ala | Pro | Thr | Gly | Gly | |
| | | | 100 | | | | | 105 | | | | | 110 | | | |
| gga | gga | tct | gtc | gag | tgc | cca | ccg | tgc | cca | gca | cca | cct | gtg | gca | gga | 384 |
| Gly | Gly | Ser | Val | Glu | Cys | Pro | Pro | Cys | Pro | Ala | Pro | Pro | Val | Ala | Gly | |
| | | | 115 | | | | | 120 | | | | | 125 | | | |
| ccg | tca | gtc | ttc | ctc | ttc | ccc | cca | aaa | ccc | aag | gac | acc | ctc | atg | atc | 432 |
| Pro | Ser | Val | Phe | Leu | Phe | Pro | Pro | Lys | Pro | Lys | Asp | Thr | Leu | Met | Ile | |
| | | 130 | | | | | 135 | | | | | 140 | | | | |
| tcc | cgg | acc | cct | gag | gtc | acg | tgc | gtg | gtg | gtg | gac | gtg | agc | cac | gaa | 480 |
| Ser | Arg | Thr | Pro | Glu | Val | Thr | Cys | Val | Val | Val | Asp | Val | Ser | His | Glu | |
| 145 | | | | | 150 | | | | | 155 | | | | | 160 | |
| gac | ccc | gag | gtc | cag | ttc | aac | tgg | tac | gtg | gac | ggc | gtg | gag | gtg | cat | 528 |
| Asp | Pro | Glu | Val | Gln | Phe | Asn | Trp | Tyr | Val | Asp | Gly | Val | Glu | Val | His | |
| | | | | 165 | | | | | 170 | | | | | 175 | | |
| aat | gcc | aag | aca | aag | cca | cgg | gag | gag | cag | ttc | aac | agc | acg | ttc | cgt | 576 |
| Asn | Ala | Lys | Thr | Lys | Pro | Arg | Glu | Glu | Gln | Phe | Asn | Ser | Thr | Phe | Arg | |
| | | | 180 | | | | | 185 | | | | | 190 | | | |

```
gtg gtc agc gtc ctc acc gtt gtg cac cag gac tgg ctg aac ggc aag      624
Val Val Ser Val Leu Thr Val Val His Gln Asp Trp Leu Asn Gly Lys
        195                 200                 205 gag tac aag tgc aag gtc tcc aac aaa ggc ctc cca gcc ccc atc gag      672
Glu Tyr Lys Cys Lys Val Ser Asn Lys Gly Leu Pro Ala Pro Ile Glu
    210                 215                 220 aaa acc atc tcc aaa acc aaa ggg cag ccc cga gaa cca cag gtg tac      720
Lys Thr Ile Ser Lys Thr Lys Gly Gln Pro Arg Glu Pro Gln Val Tyr
225                 230                 235                 240 acc ctg ccc cca tcc cgg gag gag atg acc aag aac cag gtc agc ctg      768
Thr Leu Pro Pro Ser Arg Glu Glu Met Thr Lys Asn Gln Val Ser Leu
                245                 250                 255 acc tgc ctg gtc aaa ggc ttc tat ccc agc gac atc gcc gtg gag tgg      816
Thr Cys Leu Val Lys Gly Phe Tyr Pro Ser Asp Ile Ala Val Glu Trp
            260                 265                 270 gag agc aat ggg cag ccg gag aac aac tac aag acc aca cct ccc atg      864
Glu Ser Asn Gly Gln Pro Glu Asn Asn Tyr Lys Thr Thr Pro Pro Met
        275                 280                 285 ctg gac tcc gac ggc tcc ttc ttc ctc tac agc aag ctc acc gtg gac      912
Leu Asp Ser Asp Gly Ser Phe Phe Leu Tyr Ser Lys Leu Thr Val Asp
    290                 295                 300 aag agc agg tgg cag cag ggg aac gtc ttc tca tgc tcc gtg atg cat      960
Lys Ser Arg Trp Gln Gln Gly Asn Val Phe Ser Cys Ser Val Met His
305                 310                 315                 320 gag gct ctg cac aac cac tac acg cag aag agc ctc tcc ctg tct ccg     1008
Glu Ala Leu His Asn His Tyr Thr Gln Lys Ser Leu Ser Leu Ser Pro
                325                 330                 335 ggt aaa                                                              1014
Gly Lys <210> SEQ ID NO 18
<211> LENGTH: 338
<212> TYPE: PRT
<213> ORGANISM: Homo sapiens

<400> SEQUENCE: 18

Glu Thr Arg Tyr Cys Ile Tyr Tyr Asn Ala Asn Trp Glu Leu Glu Arg
1               5                   10                  15

Thr Asn Gln Thr Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr Gly Gly
            100                 105                 110

Gly Gly Ser Val Glu Cys Pro Pro Cys Pro Ala Pro Pro Val Ala Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Gln Phe Asn Trp Tyr Val Asp Gly Val Glu Val His
                165                 170                 175
```

```
Asn Ala Lys Thr Lys Pro Arg Glu Glu Gln Phe Asn Ser Thr Phe Arg
            180                 185                 190

Val Val Ser Val Leu Thr Val His Gln Asp Trp Leu Asn Gly Lys
        195                 200                 205

Glu Tyr Lys Cys Lys Val Ser Asn Lys Gly Leu Pro Ala Pro Ile Glu
210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
            245                 250                 255

Thr Cys Leu Val Lys Gly Phe Tyr Pro Ser Asp Ile Ala Val Glu Trp
        260                 265                 270

Glu Ser Asn Gly Gln Pro Glu Asn Asn Tyr Lys Thr Thr Pro Pro Met
    275                 280                 285

Leu Asp Ser Asp Gly Ser Phe Phe Leu Tyr Ser Lys Leu Thr Val Asp
290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
            325                 330                 335

Gly Lys

<210> SEQ ID NO 19
<211> LENGTH: 110
<212> TYPE: PRT
<213> ORGANISM: Homo sapiens

<400> SEQUENCE: 19

Glu Thr Arg Trp Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110

<210> SEQ ID NO 20
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 20 gag aca cgg tgg tgc atc tac tac aac gcc aac tgg gag ctg gag cgc     48
Glu Thr Arg Trp Cys Ile Tyr Tyr Asn Ala Asn Trp Glu Leu Glu Arg
1               5                   10                  15 acc aac cag agc ggc ctg gag cgc tgc gaa ggc gag cag gac aag cgg     96
Thr Asn Gln Ser Gly Leu Glu Arg Cys Glu Gly Glu Gln Asp Lys Arg
```

```
                    20                  25                  30
ctg cac tgc tac gcc tcc tgg cgc aac agc tct ggc acc atc gag ctc      144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag      192
Val Lys Lys Gly Cys Trp Leu Asp Asp Phe Asn Cys Tyr Asp Arg Gln
 50                  55                  60 gag tgt gtg gcc act gag gag aac ccc cag gtg tac ttc tgc tgc tgt      240
Glu Cys Val Ala Thr Glu Glu Asn Pro Gln Val Tyr Phe Cys Cys Cys
 65                  70                  75                  80 gag ggc aac ttc tgc aac gag cgc ttc act cat ttg cca gag gct ggg      288
Glu Gly Asn Phe Cys Asn Glu Arg Phe Thr His Leu Pro Glu Ala Gly
                85                  90                  95 ggc ccg gaa gtc acg tac gag cca ccc ccg aca gcc ccc acc gga gga      336
Gly Pro Glu Val Thr Tyr Glu Pro Pro Pro Thr Ala Pro Thr Gly Gly
            100                 105                 110 gga gga tct gtc gag tgc cca ccg tgc cca gca cca cct gtg gca gga      384
Gly Gly Ser Val Glu Cys Pro Pro Cys Pro Ala Pro Pro Val Ala Gly
        115                 120                 125 ccg tca gtc ttc ctc ttc ccc cca aaa ccc aag gac acc ctc atg atc      432
Pro Ser Val Phe Leu Phe Pro Pro Lys Pro Lys Asp Thr Leu Met Ile
130                 135                 140 tcc cgg acc cct gag gtc acg tgc gtg gtg gtg gac gtg agc cac gaa      480
Ser Arg Thr Pro Glu Val Thr Cys Val Val Val Asp Val Ser His Glu
145                 150                 155                 160 gac ccc gag gtc cag ttc aac tgg tac gtg gac ggc gtg gag gtg cat      528
Asp Pro Glu Val Gln Phe Asn Trp Tyr Val Asp Gly Val Glu Val His
                165                 170                 175 aat gcc aag aca aag cca cgg gag gag cag ttc aac agc acg ttc cgt      576
Asn Ala Lys Thr Lys Pro Arg Glu Glu Gln Phe Asn Ser Thr Phe Arg
            180                 185                 190 gtg gtc agc gtc ctc acc gtt gtg cac cag gac tgg ctg aac ggc aag      624
Val Val Ser Val Leu Thr Val Val His Gln Asp Trp Leu Asn Gly Lys
        195                 200                 205 gag tac aag tgc aag gtc tcc aac aaa ggc ctc cca gcc ccc atc gag      672
Glu Tyr Lys Cys Lys Val Ser Asn Lys Gly Leu Pro Ala Pro Ile Glu
210                 215                 220 aaa acc atc tcc aaa acc aaa ggg cag ccc cga gaa cca cag gtg tac      720
Lys Thr Ile Ser Lys Thr Lys Gly Gln Pro Arg Glu Pro Gln Val Tyr
225                 230                 235                 240 acc ctg ccc cca tcc cgg gag gag atg acc aag aac cag gtc agc ctg      768
Thr Leu Pro Pro Ser Arg Glu Glu Met Thr Lys Asn Gln Val Ser Leu
                245                 250                 255 acc tgc ctg gtc aaa ggc ttc tat ccc agc gac atc gcc gtg gag tgg      816
Thr Cys Leu Val Lys Gly Phe Tyr Pro Ser Asp Ile Ala Val Glu Trp
            260                 265                 270 gag agc aat ggg cag ccg gag aac aac tac aag acc aca cct ccc atg      864
Glu Ser Asn Gly Gln Pro Glu Asn Asn Tyr Lys Thr Thr Pro Pro Met
        275                 280                 285 ctg gac tcc gac ggc tcc ttc ttc ctc tac agc aag ctc acc gtg gac      912
Leu Asp Ser Asp Gly Ser Phe Phe Leu Tyr Ser Lys Leu Thr Val Asp
290                 295                 300 aag agc agg tgg cag cag ggg aac gtc ttc tca tgc tcc gtg atg cat      960
Lys Ser Arg Trp Gln Gln Gly Asn Val Phe Ser Cys Ser Val Met His
305                 310                 315                 320 gag gct ctg cac aac cac tac acg cag aag agc ctc tcc ctg tct ccg     1008
Glu Ala Leu His Asn His Tyr Thr Gln Lys Ser Leu Ser Leu Ser Pro
                325                 330                 335 ggt aaa                                                              1014
```

Gly Lys

<210> SEQ ID NO 21
<211> LENGTH: 338
<212> TYPE: PRT
<213> ORGANISM: Homo sapiens

<400> SEQUENCE: 21

Glu Thr Arg Trp Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr Gly Gly
            100                 105                 110

Gly Gly Ser Val Glu Cys Pro Pro Cys Pro Ala Pro Val Ala Gly
        115                 120                 125

Pro Ser Val Phe Leu Phe Pro Pro Lys Pro Lys Asp Thr Leu Met Ile
130                 135                 140

Ser Arg Thr Pro Glu Val Thr Cys Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Met
        275                 280                 285

Leu Asp Ser Asp Gly Ser Phe Phe Leu Tyr Ser Lys Leu Thr Val Asp
290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 22
<211> LENGTH: 216
<212> TYPE: PRT

<213> ORGANISM: Homo sapiens

<400> SEQUENCE: 22

```
Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215
```

<210> SEQ ID NO 23
<211> LENGTH: 217
<212> TYPE: PRT
<213> ORGANISM: Homo sapiens

<400> SEQUENCE: 23

```
Ala Pro Glu Leu Leu Gly Gly Pro Ser Val Phe Leu Phe Pro Pro Lys
1               5                   10                  15

Pro Lys Asp Ile Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Gly Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
```

```
                130             135             140
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 24
<211> LENGTH: 217
<212> TYPE: PRT
<213> ORGANISM: Homo sapiens

<400> SEQUENCE: 24

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
    210                 215

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 25

Gly Gly Gly Gly Ser
```

```
<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(36)

<400> SEQUENCE: 26 gga ggg gga gga tct gtc gag tgc cca ccg tgc cca              36
Gly Gly Gly Gly Ser Val Glu Cys Pro Pro Cys Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 27

Gly Gly Gly Gly Ser Val Glu Cys Pro Pro Cys Pro
1               5                   10

<210> SEQ ID NO 28
<211> LENGTH: 12
<212> TYPE: PRT
<213> ORGANISM: Homo sapiens

<400> SEQUENCE: 28

Glu Arg Lys Cys Cys Val Glu Cys Pro Pro Cys Pro
1               5                   10

<210> SEQ ID NO 29
<211> LENGTH: 15
<212> TYPE: PRT
<213> ORGANISM: Homo sapiens

<400> SEQUENCE: 29

Glu Pro Lys Ser Cys Asp Lys Thr His Thr Cys Pro Pro Cys Pro
1               5                   10                  15

<210> SEQ ID NO 30
<211> LENGTH: 12
<212> TYPE: PRT
<213> ORGANISM: Homo sapiens

<400> SEQUENCE: 30

Glu Ser Lys Thr Gly Pro Pro Cys Pro Ser Cys Pro
1               5                   10

<210> SEQ ID NO 31
<211> LENGTH: 18
<212> TYPE: PRT
<213> ORGANISM: Homo sapiens

<400> SEQUENCE: 31

Met Thr Ala Pro Trp Val Ala Leu Ala Leu Leu Trp Gly Ser Leu Trp
1               5                   10                  15

Pro Gly
```

```
<210> SEQ ID NO 32
<211> LENGTH: 18
<212> TYPE: PRT
<213> ORGANISM: Homo sapiens

<400> SEQUENCE: 32

Met Thr Ala Pro Trp Val Ala Leu Ala Leu Leu Trp Gly Ser Leu Cys
1               5                   10                  15

Ala Gly

<210> SEQ ID NO 33
<211> LENGTH: 512
<212> TYPE: PRT
<213> ORGANISM: Homo sapiens

<400> SEQUENCE: 33

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300
```

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
            325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
            405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
            485                 490                 495

Val Thr Ser Val Thr Asn Val Asp Leu Pro Pro Lys Glu Ser Ser Ile
            500                 505                 510

<210> SEQ ID NO 34
<211> LENGTH: 426
<212> TYPE: PRT
<213> ORGANISM: Homo sapiens

<400> SEQUENCE: 34

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
            195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
            245                 250                 255

Leu Gly Lys Lys Lys Lys Glu Glu Glu Gly Glu Lys Lys Lys
            260                 265                 270

Gly Gly Gly Glu Gly Gly Ala Gly Ala Asp Glu Glu Lys Glu Gln Ser
            275                 280                 285

His Arg Pro Phe Leu Met Leu Gln Ala Arg Gln Ser Glu Asp His Pro
            290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
            325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
            370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
            405                 410                 415

Asn Met Ile Val Glu Glu Cys Gly Cys Ser
            420                 425

<210> SEQ ID NO 35
<211> LENGTH: 375
<212> TYPE: PRT
<213> ORGANISM: Homo sapiens

<400> SEQUENCE: 35

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
        50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
            85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu

```
            115                 120                 125
Met Gln Val Asp Gly Lys Pro Lys Cys Cys Phe Phe Lys Phe Ser Ser
        130                 135                 140
Lys Ile Gln Tyr Asn Lys Val Lys Ala Gln Leu Trp Ile Tyr Leu
145                 150                 155                 160
Arg Pro Val Glu Thr Pro Thr Val Phe Val Gln Ile Leu Arg Leu
                165                 170                 175
Ile Lys Pro Met Lys Asp Gly Thr Arg Tyr Thr Gly Ile Arg Ser Leu
            180                 185                 190
Lys Leu Asp Met Asn Pro Gly Thr Gly Ile Trp Gln Ser Ile Asp Val
            195                 200                 205
Lys Thr Val Leu Gln Asn Trp Leu Lys Gln Pro Glu Ser Asn Leu Gly
210                 215                 220
Ile Glu Ile Lys Ala Leu Asp Glu Asn Gly His Asp Leu Ala Val Thr
225                 230                 235                 240
Phe Pro Gly Pro Gly Glu Asp Gly Leu Asn Pro Phe Leu Glu Val Lys
                245                 250                 255
Val Thr Asp Thr Pro Lys Arg Ser Arg Arg Asp Phe Gly Leu Asp Cys
                260                 265                 270
Asp Glu His Ser Thr Glu Ser Arg Cys Cys Arg Tyr Pro Leu Thr Val
            275                 280                 285
Asp Phe Glu Ala Phe Gly Trp Asp Trp Ile Ile Ala Pro Lys Arg Tyr
            290                 295                 300
Lys Ala Asn Tyr Cys Ser Gly Glu Cys Glu Phe Val Phe Leu Gln Lys
305                 310                 315                 320
Tyr Pro His Thr His Leu Val His Gln Ala Asn Pro Arg Gly Ser Ala
                325                 330                 335
Gly Pro Cys Cys Thr Pro Thr Lys Met Ser Pro Ile Asn Met Leu Tyr
            340                 345                 350
Phe Asn Gly Lys Glu Gln Ile Ile Tyr Gly Lys Ile Pro Ala Met Val
            355                 360                 365
Val Asp Arg Cys Gly Cys Ser
            370                 375

<210> SEQ ID NO 36
<211> LENGTH: 217
<212> TYPE: PRT
<213> ORGANISM: Homo sapiens

<400> SEQUENCE: 36

Ala Pro Glu Leu Leu Gly Gly Pro Ser Val Phe Leu Phe Pro Pro Lys
1               5                   10                  15
Pro Lys Asp Ile Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Gly Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
```

```
Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(48)

<400> SEQUENCE: 37 gga ggg gga gga tct gag cgc aaa tgt tgt gtc gag tgc cca ccg tgc    48
Gly Gly Gly Gly Ser Glu Arg Lys Cys Cys Val Glu Cys Pro Pro Cys
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 38

Gly Gly Gly Gly Ser Glu Arg Lys Cys Cys Val Glu Cys Pro Pro Cys
1               5                   10                  15

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(42)

<400> SEQUENCE: 39 gga ggg gga gga tct ggt gga ggt ggt tca ggt cca ccg tgc    42
Gly Gly Gly Gly Ser Gly Gly Gly Gly Ser Gly Pro Pro Cys
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      hinge linker peptide
```

<400> SEQUENCE: 40

Gly Gly Gly Gly Ser Gly Gly Gly Gly Ser Gly Pro Pro Cys
1               5                   10

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(42)

<400> SEQUENCE: 41 gga ggg gga gga tct ggt gga ggt ggt tca ggt cca ccg gga         42
Gly Gly Gly Gly Ser Gly Gly Gly Gly Ser Gly Pro Pro Gly
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 42

Gly Gly Gly Gly Ser Gly Gly Gly Gly Ser Gly Pro Pro Gly
1               5                   10

<210> SEQ ID NO 43
<211> LENGTH: 54
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(54)

<400> SEQUENCE: 43 gga ggg gga gga tct gag cgc aaa tgt cca cct tgt gtc gag tgc cca     48
Gly Gly Gly Gly Ser Glu Arg Lys Cys Pro Pro Cys Val Glu Cys Pro
1               5                   10                  15 ccg tgc                                                             54
Pro Cys

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 44

Gly Gly Gly Gly Ser Glu Arg Lys Cys Pro Pro Cys Val Glu Cys Pro
1               5                   10                  15

Pro Cys

<210> SEQ ID NO 45
<211> LENGTH: 14
<212> TYPE: PRT

```
<213> ORGANISM: Artificial Sequence
<220> FEATURE:
<223> OTHER INFORMATION: Description of Artificial Sequence: Synthetic
      hinge linker peptide

<400> SEQUENCE: 45

Gly Pro Ala Ser Gly Gly Pro Ala Ser Gly Pro Pro Cys Pro
1               5                   10

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 46

Gly Pro Ala Ser Gly Gly Pro Ala Ser Gly Cys Pro Pro Cys Val Glu
1               5                   10                  15

Cys Pro Pro Cys Pro
            20

<210> SEQ ID NO 47
<211> LENGTH: 217
<212> TYPE: PRT
<213> ORGANISM: Homo sapiens

<400> SEQUENCE: 47

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 48
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 48

Gly Gly Gly Gly Ser Val Asp Lys Thr His Thr Cys Pro Pro Cys Pro
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 49

Gly Gly Gly Gly Ser Val Asp Lys Thr His Thr Gly Pro Pro Cys Pro
1               5                   10                  15

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 50

Gly Gly Gly Gly Ser Gly Gly Gly Ser Val Asp Lys Thr His Thr
1               5                   10                  15

Gly Pro Pro Cys Pro
            20
```

ISOLATED NUCLEIC ACID MOLECULES ENCODING STABILIZED RECEPTOR POLYPEPTIDES AND USES THEREOF

REFERENCE TO RELATED APPLICATIONS

This application is a continuation application of U.S. Ser. No. 13/775,756, filed Feb. 25, 2013, which claims benefit of U.S. Ser. No. 12/626,375 (U.S. Pat. No. 8,410,043), filed Nov. 25, 2009, which claims the benefit of U.S. Provisional Application Ser. No. 61/200,250, filed on Nov. 26, 2008, and U.S. Provisional Application Ser. No. 61/259,060, filed on Nov. 6, 2009, the entire disclosures of which are relied upon and incorporated by reference herein.

REFERENCE TO THE SEQUENCE LISTING

The instant application contains a Sequence Listing which has been submitted via EFS-Web and is hereby incorporated by reference in its entirety. Said ASCII copy, created on Jan. 21, 2016, is named 32735US_CRF_sequencelisting.txt, and is 84 kilobytes in size.

TECHNICAL FIELD OF THE INVENTION

The technical field of this invention relates to transforming growth factor-β (TGF-β) family members and soluble TGF-β receptors with improved properties, as well as methods of modulating the activities of TGF-β family members for the treatment of various disorders.

BACKGROUND OF THE INVENTION

The transforming growth factor β (TGF-β) family of proteins includes the transforming growth factors-β (TGF-β), activins, bone morphogenic proteins (BMP), nerve growth factors (NGFs), brain-derived neurotrophic factor (BDNF), and growth/differentiation factors (GDFs). These family members are involved in the regulation of a wide range of biological processes including cell proliferation, differentiation, and other functions.

Growth/differentiation factor 8 (GDF-8), also referred to as myostatin, is a TGF-β family member expressed for the most part in the cells of developing and adult skeletal muscle tissue. Myostatin appears to play an essential role in negatively controlling skeletal muscle growth (McPherron et al., Nature (London) 387, 83-90 (1997), Zimmers et al., Science 296:1486-1488 (2002)). Antagonizing myostatin has been shown to increase lean muscle mass in animals.

Another member of the TGF-β family of proteins is a related growth/differentiation factor, growth/differentiation factor 11 (GDF-11). GDF-11 has approximately 90% sequence identity to the amino acid sequence of myostatin. GDF-11 has a role in the axial patterning in developing animals (Oh et al., Genes Dev 11:1812-26 (1997)), and also appears to play a role in skeletal muscle development and growth.

Activins A, B and AB are the homodimers and heterdimer respectively of two polypeptide chains, βA and βB (Vale et al., Nature 321, 776-779 (1986), Ling et al., Nature 321, 779-782 (1986)). Activins were originally discovered as gonadal peptides involved in the regulation of follicle stimulating hormone synthesis, and are now believed to be involved in the regulation of a number of biological activities. Activin A is a predominant form of activin.

Activin, myostatin, GDF-11 and other members of the TGF-β superfamily bind and signal through a combination of activin type II and activin type IIB receptors, both of which are transmembrane serine/threonine kinases (Harrison et al., J. Biol. Chem. 279, 28036-28044 (2004)). Cross-linking studies have determined that myostatin is capable of binding the activin type II receptors ActRIIA and ActRIIB in vitro (Lee et al., PNAS USA 98:9306-11 (2001)). There is also evidence that GDF-11 binds to both ActRIIA and ActRIIB (Oh et al., Genes Dev 16:2749-54 (2002)).

TGF-β protein expression is known to be associated with a variety of diseases and disorders. Therefore, therapeutic molecules capable of antagonizing several TGF-β proteins simultaneously may be particularly effective for treating these diseases and disorders.

Production of therapeutic proteins on a commercial scale requires proteins that can be efficiently expressed and purified without disruption of the integrity of the protein. Manufacturability can be described as the ability to express and purify a protein in a sufficiently efficient manner to allow for cost-effective production of the protein. In a commercial setting, manufacturability must be determined for each potential therapeutic protein. Although protein expression and purification processes can be optimized for a protein, manufacturability appears to be a function of the intrinsic properties of the protein as well. The present invention provides biologically active therapeutic proteins having improved manufacturability properties, capable of effectively antagonizing TGF-β proteins.

SUMMARY OF THE INVENTION

The present invention provides isolated proteins comprising stabilized human activin receptor IIB (designated svActRIIB) polypeptides capable of binding and inhibiting the activities of activin, GDF-11 and myostatin, and characterized by improved manufacturability properties. The stabilized ActRIIB polypeptides are characterized by having amino acid substitutions at both positions 28 and 44 with respect to SEQ ID NO: 2.

In one embodiment, the isolated protein comprises a polypeptide having the sequence set forth in SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 19 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 23 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 25 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has an amino acid sequence with at least 80%, 85%, 90%, 95%, 98% or 99% identity to any of the polypeptides above, wherein the polypeptide has single amino acid substitution at position 28, and a single amino acid substitution at position 44, wherein the substitution at position 28 is selected from W or Y, and the substitution at position 44 is T, and wherein the polypeptide is capable of binding myostatin, activin A, or GDF-11. In one embodiment, the substitution of the above polypeptides at position 28 is W and the substitution at position 44 is T, wherein the polypeptide is capable of binding myostatin, activin A, or GDF-11.

In another embodiment, the isolated protein comprises a stabilized activin IIB receptor polypeptide, wherein the polypeptide has the sequence set forth in the group consisting of SEQ ID NO: 4, 6, 12 and 14. In another embodiment the protein comprises a polypeptide having at least 80% sequence identity to SEQ ID NO: 4, 6, 12 or 14, wherein the polypeptide has a W or Y at position 28 and a T at position 44, and wherein the polypeptide is capable of binding myostatin, activin A, or GDF-11. In another embodiment the protein comprises a polypeptide having at least 90% sequence identity to SEQ ID NO: 4, 6, 12 or 14, wherein the polypeptide has a W or Y at position 28 and a T at position 44, and wherein the polypeptide is capable of binding myostatin, activin A, or GDF-11. In another embodiment, the protein comprises a polypeptide having at least 95% sequence identity to SEQ ID NO: 4, 6, 12, or 14, wherein the polypeptide has a W or Y at position 28 and a T at position 44, and wherein the polypeptide is capable of binding myostatin, activin A, or GDF-11. In one embodiment, the substitution at position 28 is W and the substitution at position 44 is T, wherein the polypeptide is capable of binding myostatin, activin A, or GDF-11.

In a further embodiment the svActRIIB protein further comprises a heterologous protein. In one embodiment, the heterologous protein is an Fc domain. In a further embodiment, the Fc domain is a human IgG Fc domain. In a further embodiment the heterologous protein is attached by a linker or a hinge linker peptide. In one embodiment, the linker or hinge linker is selected from group consisting of the amino acid sequences set forth in the group consisting of SEQ ID NO: 25, 27, 38, 40, 42, 44, 45, 46, 48, 49 and 50. In a further embodiment the hinge linkers set forth in SEQ ID NO: 27, 38, 40, 42, 44, 45, or 46 link the human IgG2 Fc (SEQ ID NO: 22) to an svActRIIB polypeptide. In another embodiment, the hinge linkers set forth in SEQ ID NO: 48, 49, or 50 link the human IgG1 Fc (SEQ ID NO: 23) or the modified IgG1 Fc (SEQ ID NO: 47) to an svActRIIB polypeptide.

In a further embodiment, the protein comprises a polypeptide having the sequence set forth in the group consisting of SEQ ID NO: 8, 10, 16 and 18. In another embodiment the protein comprises a polypeptide having at least 80% sequence identity to SEQ ID NO: 8, 10, 16 or 18, wherein the polypeptide has a W or Y at position 28 and a T at position 44, and wherein the polypeptide is capable of binding myostatin, activin A, or GDF-11. In another embodiment the protein comprises a polypeptide having at least 90% sequence identity to SEQ ID NO: 8, 10, 16 or 18, wherein the polypeptide has a W or Y at position 28 and a T at position 44, and wherein the polypeptide is capable of binding myostatin, activin A, or GDF-11. In another embodiment, the protein comprises a polypeptide having at least 95% sequence identity to SEQ ID NO: 8, 10, 16, or 18, wherein the polypeptide has a W or Y at position 28 and a T at position 44, and wherein the polypeptide is capable of binding myostatin, activin A, or GDF-11. In a further embodiment, the substitution of the above polypeptides at position 28 is W and the substitution at position 44 is T, wherein the polypeptide is capable of binding myostatin, activin A, or GDF-11.

In a further embodiment, the protein comprises the polypeptides recited above, wherein the amino acid residue at position 64 is alanine.

In another aspect the present invention provides an isolated nucleic acid molecule comprising a polynucleotide encoding a stabilized ActRIIB polypeptide. In one embodiment, the polynucleotide encodes the polypeptide sequence set forth in SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes the polypeptide having the sequence set forth in amino acids 19 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes the polypeptide having the sequence set forth in amino acids 23 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes the polypeptide having the sequence set forth in amino acids 25 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes the a polypeptide having an amino acid sequence at least 80%, 85%, 90%, 95%, 98% or 99% identity to any one of the polypeptides above, wherein the polypeptide has single amino acid substitution at position 28, and a single amino acid substitution at position 44, wherein the substitution at position 28 is selected from W or Y, and the substitution at position 44 is T, and wherein the polypeptide is capable of binding myostatin, activin A, or GDF-11. In one embodiment, the above polynucleotides encode a polypeptide wherein the substitution at position 28 is W and the substitution at position 44 is T, wherein the polypeptide is capable of binding myostatin, activin A, or GDF-11.

In one embodiment, the nucleic acid molecule comprises a polynucleotide encoding a polypeptide having the sequence set forth in the group consisting of SEQ ID NO: 4, 6, 12 and 14. In another embodiment, the nucleic acid molecule comprises a polynucleotide encoding a polypeptide having at least 80% sequence identity to SEQ ID NO: 4, 6, 12 or 14, wherein the polypeptide has a W or Y at position 28 and a T at position 44, and wherein the polypeptide is capable of binding myostatin, activin A, or GDF-11. In another embodiment, the nucleic acid molecule comprises a polynucleotide encoding a polypeptide having at least 90% sequence identity to SEQ ID NO: 4, 6, 12 or 14, wherein the polypeptide has a W or Y at position 28 and a T at position 44, and wherein the polypeptide is capable of binding myostatin, activin A, or GDF-11. In another embodiment, the nucleic acid molecule comprises a polynucleotide encoding a polypeptide having at least 95% sequence identity to SEQ ID NO: 4, 6, 12 or 14, wherein the polypeptide has a W or Y at position 28 and a T at position 44, and wherein the polypeptide is capable of binding myostatin, activin A, or GDF-11. In one embodiment, the above polynucleotides encode a polypeptide wherein the substitution at position 28 is W and the substitution at position 44 is T, wherein the polypeptide is capable of binding myostatin, activin A, or GDF-11.

In another embodiment, the nucleic acid molecule comprises a polynucleotide having a sequence selected from the group consisting of SEQ ID NO: 3, 5, 11 and 13, or its complement.

In another embodiment, the isolated nucleic acid molecule comprises the polynucleotides set forth above, and further comprises a polynucleotide encoding at least one heterologous protein. In one embodiment, the nucleic acid molecule comprises a polynucleotide encoding a polypeptide having the sequence set forth in the group consisting of SEQ ID NO: 8, 10, 16 and 18. In another embodiment, the nucleic acid molecule comprises a polynucleotide encoding a polypeptide having at least 80% sequence identity to SEQ ID NO: 8, 10, 16 or 18, wherein the polypeptide has a W or Y at position 28 and a T at position 44, and wherein the polypeptide is capable of binding myostatin, activin A, or GDF-11. In another embodiment, the nucleic acid molecule comprises a polynucleotide encoding a polypeptide having at least 90% sequence identity to SEQ ID NO: 8, 10, 16 or 18, wherein the polypeptide has a W or Y at position 28 and a T at position 44, and wherein the polypeptide is capable of binding myostatin, activin A, or GDF-11. In another embodiment, the nucleic acid molecule comprises a polynucleotide encoding a polypeptide having at least 95% sequence identity to SEQ ID NO: 8, 10, 16 or 18, wherein the polypeptide has a W or Y at position 28 and a T at position 44, and wherein the polypeptide is capable of binding myostatin, activin A, or GDF-11. In one embodiment, the above polynucleotides encode a polypeptide wherein the substitution at position 28 is W and the substitution at position S44 is T, wherein the encoded polypeptide is capable of binding myostatin, activin A or GDF-11. In a further embodiment, the nucleic acid molecule comprises a polynucleotide having a sequence selected from the group consisting of SEQ ID NO: 7, 9, 15 and 17, or its complement.

In another embodiment, the nucleic acid molecule further comprises polynucleotides encoding the linkers and hinge linkers set forth in the group consisting of SEQ ID NO: 25, 27, 38, 40, 42, 44, 45, 46, 48, 49 and 50.

In a further embodiment, the nucleic acid molecule further comprises a transcriptional or translational regulatory sequence. In another aspect a recombinant vector comprising a polynucleotide encoding a stabilized ActRIIB protein or polypeptide is provided. In another aspect, host cells comprising the recombinant vectors are provided, and methods of producing the stabilized ActRIIB proteins and polypeptides are provided by culturing the host cells under conditions promoting expression of the proteins or polypeptides.

The present invention further provides a composition containing at least one stabilized ActRIIB polypeptide or protein of the present invention. In one embodiment, the composition is a pharmaceutical composition containing the stabilized ActRIIB polypeptide or protein in admixture with a pharmaceutically acceptable carrier.

In another aspect, the invention provides a method of reducing or blocking myostatin, activin A or GDF-11 activity by administering the svActRIIB proteins and polypeptides, or pharmaceutical compositions containing these, to a subject in need of such treatment.

In another aspect, the invention provides a method of increasing lean muscle mass or increasing the ratio of lean muscle mass to fat mass in a subject in need of such treatment by administering an effective amount of the composition or pharmaceutical composition containing svActRIIB proteins or polypeptides to the subject.

In another aspect, the invention provides a method of treating or preventing a muscle wasting disease in a subject suffering from such a disorder by administering a therapeutic composition containing an svActRIIB polypeptide or protein to the subject. The muscle wasting disease includes, but is not limited to, the following conditions: cancer cachexia, muscular dystrophy, amyotrophic lateral sclerosis, congestive obstructive pulmonary disease, chronic heart failure, chemical cachexia, cachexia from HIV/AIDS, renal failure, uremia, rheumatoid arthritis, age-related sarcopenia, age-related frailty, organ atrophy, carpal tunnel syndrome, androgen deprivation, and muscle-wasting due to inactivity from prolonged bed rest, spinal chord injury, stroke, bone fracture, burns, aging, insulin resistance, and other disorders. The muscle wasting may also result from weightlessness due to space flight.

In another aspect, the present invention provides a method of treating conditions in which activin is overexpressed in a subject in need of such treatment, by administering an effective amount of a therapeutic composition containing svActRIIB proteins or polypeptides to the subject. In one embodiment, the disease is cancer. In another aspect, the present invention provides a method of treating a metabolic disorder comprising administering a therapeutic composition containing svActRIIB proteins or polypeptides to a subject in need of such treatment, wherein the metabolic disorder is selected from bone loss, diabetes, obesity, impaired glucose tolerance, hyperglycemia, and metabolic syndrome. In another aspect, the present invention provides a method of gene therapy for treating muscle wasting or metabolic or activin-related disorders comprising administering a vector encoding an svActRIIB polypeptide or protein of the present invention to a subject in need thereof, wherein the vector is capable of expressing the svActRIIB protein or polypeptide in the subject.

In another aspect, the present invention provides a method of detecting and quantitating myostatin, activin, or GDF-11 by using any of the svActRIIB proteins or polypeptides as capture or binding agents in any number of assays.

DETAILED DESCRIPTION

Figure 1:
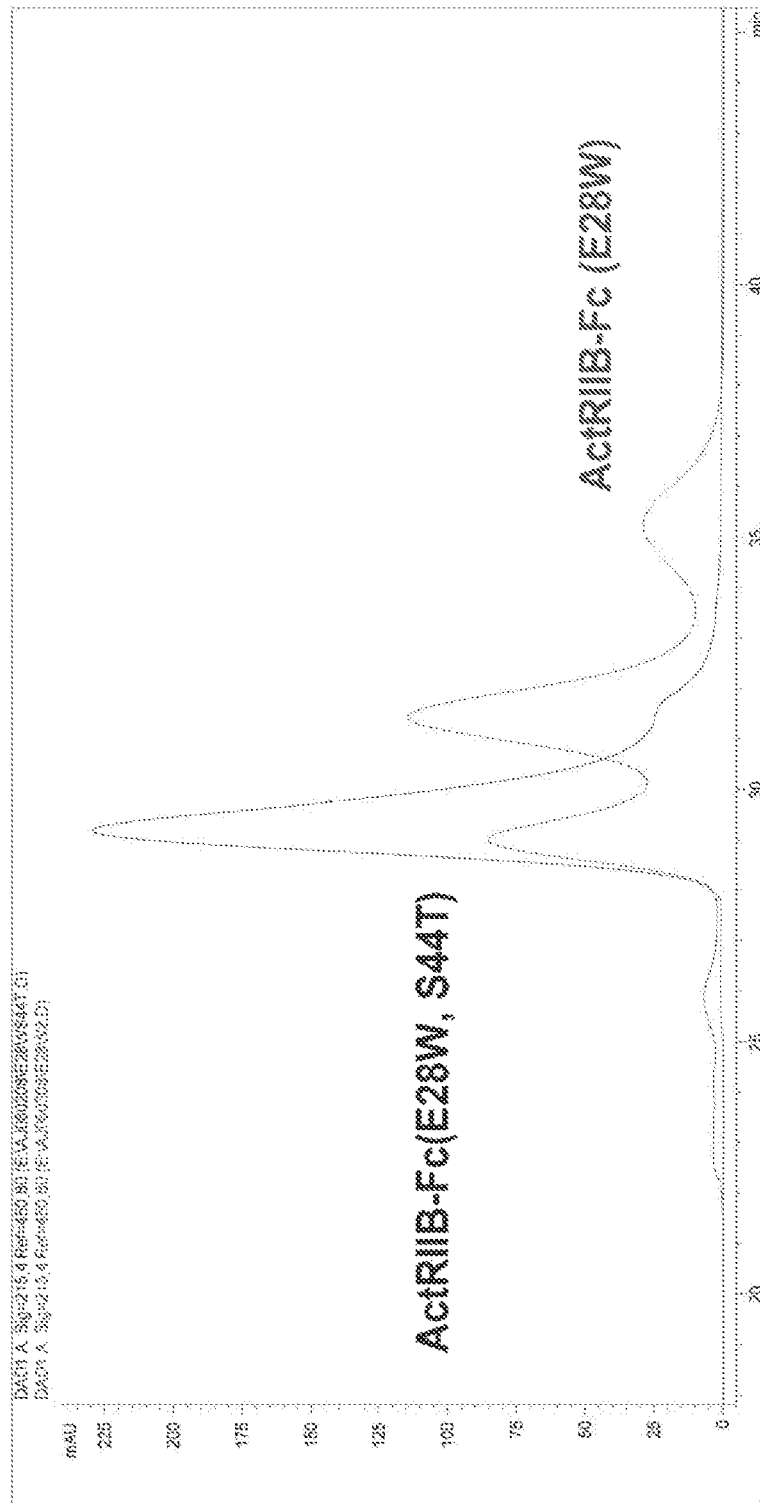
FIG. 1 shows a comparison between ActRIIB-Fc (E28W) and svActRIIB-Fc (E28W, S44T) on an SEC column. svActRIIB-Fc (E28W, S44T) shows a single peak compared with ActRIIB-Fc (E28W), which shows three peaks.

The present invention provides an isolated protein comprising a stabilized human activin IIB receptor (svActRIIB) polypeptide. The protein and polypeptide of the invention are characterized by their ability to bind to at least one of three TGF-β proteins, myostatin (GDF-8), activin A, or GDF-11, to inhibit the activities of at least one of these proteins, and to have improved manufacturability properties compared with other ActRIIB soluble receptors. The stabilized human activin IIB receptor polypeptide is characterized by amino acid substitutions at both positions E28 and S44 with reference to the extracellular domain of ActRIIB, as set forth in SEQ ID NO: 2. In one embodiment, a stabilized human activin IIB receptor polypeptide can have a further substitution of alanine at position 64 with respect to SEQ ID NO: 2.

As used herein the term "TGF-β family members" or "TGF-β proteins" refers to the structurally related growth factors of the transforming growth factor family including activins, and growth and differentiation factor (GDF) proteins (Kingsley et al. Genes Dev. 8: 133-146 (1994), McPherron et al., Growth factors and cytokines in health and disease, Vol. 1B, D. LeRoith and C. Bondy. ed., JAI Press Inc., Greenwich, Conn., USA: pp 357-393).

GDF-8, also referred to as myostatin, is a negative regulator of skeletal muscle tissue (McPherron et al. PNAS USA 94:12457-12461 (1997)). Myostatin is synthesized as an inactive protein approximately 375 amino acids in length, having GenBank Accession No: AAB86694 (SEQ ID NO: 35) for human. The precursor protein is activated by proteolytic cleavage at a tetrabasic processing site to produce an N-terminal inactive prodomain and an approximately 109 amino acid C-terminal protein which dimerizes to form a homodimer of about 25 kDa. This homodimer is the mature, biologically active protein (Zimmers et al., Science 296, 1486 (2002)).

As used herein, the term "prodomain" or "propeptide" refers to the inactive N-terminal protein which is cleaved off to release the active C-terminal protein. As used herein the term "myostatin" or "mature myostatin" refers to the mature, biologically active C-terminal polypeptide, in monomer, dimer or other form, as well as biologically active fragments or related polypeptides including allelic variants, splice variants, and fusion peptides and polypeptides. The mature myostatin has been reported to have 100% sequence identity among many species including human, mouse, chicken, porcine, turkey, and rat (Lee et al., PNAS 98, 9306 (2001)).

As used herein GDF-11 refers to the BMP (bone morphogenic protein) having Swissprot accession number O95390 (SEQ ID NO: 36), as well as variants and species homologs of that protein. GDF-11 is involved in the regulation of anterior/posterior patterning of the axial skeleton (McPherron et al, Nature Genet. 22 (93): 260-264 (1999); Gamer et al, Dev. Biol. 208 (1), 222-232 (1999)) but postnatal functions are unknown.

Activin A is the homodimer of the polypeptide chains βA. As used herein the term "activin A" refers to the activin protein having GenBank Accession No: NM_002192 (SEQ ID NO: 34). Activins A, B, and AB are the homodimers and heterodimer respectively of two polypeptide chains, βA and βB. As used herein, "activin" refers to activin A, B, and AB, as well as variants and species homologs of that protein.

Receptor Polypeptides

As used herein, the term activin type II B receptors (ActRIIB) refers to human activin receptors having accession number NP_001097 or variants thereof, such as those having the arginine at position 64 substituted with alanine. The term soluble ActRIIB (wild type) refers to the extracellular domain of ActRIIB, amino acids 1 to 134 (with signal sequence), or amino acids 19 through 134 of SEQ ID NO: 2 (without signal sequence).

Stabilized Receptor Polypeptides

The present invention provides an isolated protein comprising a stabilized ActIIB receptor polypeptide (referred herein as "svActRIIB polypeptide"). As used herein the term "svActRIIB protein" refers to a protein comprising a stabilized ActRIIB polypeptide. As used herein the term "isolated" refers to a protein or polypeptide molecule purified to some degree from endogenous material. These polypeptides and proteins are characterized as having the ability to bind and inhibit the activity of any one of activin A, myostatin, or GDF-11, in addition to having improved manufacturability characteristics.

The stabilized ActRIIB polypeptide is characterized by having an amino acid substitution at both position 28 and 44 with respect to SEQ ID NO: 2. For consistency, the amino acid positions on the stabilized ActRIIB polypeptides and proteins are always referred to with respect to the positions in SEQ ID NO: 2, regardless of whether the polypeptide is mature or truncated. As used herein, the term "mature" refers to a polypeptide or peptide without its signal sequence. As used herein, the term "truncated" refers to polypeptides having N terminal amino acids or C terminal amino acids removed.

In one embodiment, the isolated stabilized activin IIB receptor polypeptide (svActRIIB) has the polypeptide sequence set forth in SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 19 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 23 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 25 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has an amino acid sequence with at least 80%, 85%, 90%, 95%, 96%, 97%, 98% or 99% identity to any one of the polypeptides above, wherein the polypeptide has single amino acid substitution at position 28, and a single amino acid substitution at position 44, wherein the substitution at position 28 is selected from W or Y, and the substitution at position 44 is T, and wherein the polypeptide is capable of binding myostatin, activin A, or GDF-11. In one embodiment, the substitution of the above polypeptides at position 28 is W, and the substitution at position 44 is T, wherein the polypeptide is capable of binding myostatin, activin A, or GDF-11.

In one embodiment, the svActRIIB polypeptide includes a signal sequence, for example, SEQ ID NO: 4, 8, 12, and 16. However, various signal peptides can be used in the preparation of the polypeptides of the instant application. The signal peptides can have the sequence set forth in amino acids 1 to 19 of SEQ ID NO: 4, for example, or the signal sequences set forth in SEQ ID NO: 31 and 32. Any other signal peptides useful for expressing svActRIIB polypeptides may be used. In other embodiments, the signal sequence is removed, leaving the mature peptide. Examples of svActRIIB polypeptides lacking a signal sequence includes, for example, SEQ ID NO: 6, 10, 14 and 18.

In one embodiment, the protein comprises a stabilized activin IIB receptor polypeptide, wherein the polypeptide is selected from the group consisting of polypeptides having the sequence set forth in the group consisting of SEQ ID NO: 4, 6, 12 and 14. These polypeptides represent amino acids 25 to 134 of SEQ ID NO: 2, wherein the polypeptide has single amino acid substitution at position 28, and a single amino acid substitution at position 44, wherein the substitution at position 28 is selected from W or Y, and the substitution at position 44 is T, and wherein the polypeptide is capable of binding myostatin, activin A, or GDF-11, with and without a signal sequence different from that shown in SEQ ID NO: 2. In another embodiment the protein comprises a polypeptide having at least 80%, 85%, 90%, 95%, 96%, 97%, 98%, or 99% sequence identity to SEQ ID NO: 4, 6, 12 or 14, wherein the polypeptide has a W or Y at position 28 and a T at position 44, and wherein the polypeptide is capable of binding myostatin, activin A, or GDF-11. In one embodiment, the substitution at position 28 is W and the substitution at position 44 is T, wherein the polypeptide is capable of binding myostatin, activin A or GDF-11.

In a further embodiment the svActRIIB protein further comprises a heterologous protein. In one embodiment, the heterologous protein is an Fc domain. In a further embodiment, the Fc domain is a human IgG Fc domain. In one embodiment, the protein comprises a polypeptide having the sequence set forth in the group consisting of SEQ ID NO: 8, 10, 16 and 18. In another embodiment, the protein comprises a polypeptide having at least 80%, 85%, 90%, 95%, 96%, 97%, 98%, or 99% sequence identity to SEQ ID NO: 8, 10, 16 or 18, wherein the polypeptide has a W or Y at position 28 and a T at position 44, and wherein the polypeptide is capable of binding myostatin, activin A, or GDF-11. In one embodiment, the substitution at position 28 is W and the substitution at position 44 is T, wherein the polypeptide is capable of binding myostatin, activin A or GDF-11.

In a further embodiment, the protein comprises the any one of the polypeptides described above, wherein the amino acid residue at position 64 is alanine.

In another embodiment, the term svActRIIB polypeptide and protein encompasses proteins comprising fragments of SEQ ID NO: 2, 4, 6, 12 and 14, including N and C terminal truncations, wherein position 28 is W or Y, and position 44 is T, and wherein the polypeptide is capable of binding myostatin, activin A or GDF-11.

As used herein the term "derivative" of the svActRIIB polypeptide refers to the attachment of at least one additional chemical moiety, or at least one additional polypeptide to form covalent or aggregate conjugates such as glycosyl groups, lipids, acetyl groups, or C-terminal or N-terminal fusion polypeptides, conjugation to PEG molecules, and other modifications which are described more fully below. Stabilized ActRIIB receptor polypeptides can also include additional modifications and derivatives, including modifications to the C and N termini which arise from processing due to expression in various cell types such as mammalian cells, *E. coli*, yeasts and other recombinant host cells.

The svActRIIB proteins of the present invention may further comprise heterologous polypeptides attached to the svActRIIB polypeptide either directly or through a linker sequence to form a fusion protein. As used herein the term "fusion protein" refers to a protein having a heterologous polypeptide attached via recombinant DNA techniques. Heterologous polypeptides include but are not limited to Fc polypeptides, his tags, and leucine zipper domains to promote oligomerization and further stabilization of the stabilized ActRIIB polypeptides as described in, for example, WO 00/29581, which is herein incorporated by reference. In one embodiment, the heterologous polypeptide is an Fc polypeptide or domain. In one embodiment, the Fc domain is selected from a human IgG1 Fc (SEQ ID NO: 23), modified IgG1 Fc (SEQ ID NO: 47), IgG2 Fc (SEQ ID NO: 22), and IgG4 Fc (SEQ ID NO: 24) domain. The svActRIIB protein can further comprise all or a portion of the hinge sequence of the IgG1 (SEQ ID NO: 29), IgG2 (SEQ ID NO: 28), or IgG4 (SEQ ID NO: 30). Exemplary svActRIIB polypeptides are selected from polypeptides consisting of the sequences as set forth in SEQ ID NO: 8, 10, 16 and 18, as well as those polypeptides having substantial similarity to these sequences, wherein the substitutions at positions 28 and 44 are retained. As used herein, "substantial similarity" refers to sequences that are at least 80% identical, 85% identical, 90% identical, 95% identical, 96% identical, 97% identical, 98% identical, 99% identical to any of SEQ ID NO: 8, 10, 16, and 18, wherein the polypeptides retain W or Y at position 28 and T at position 44, and wherein the polypeptide is capable of binding myostatin, activin A or GDF-11. In one embodiment, the substitution at position 28 is W and the substitution at position 44 is T, wherein the polypeptide is capable of binding myostatin, activin A or GDF-11.

The svActRIIB polypeptide can optionally further comprise a "linker" sequence. Linkers serve primarily as a spacer between a polypeptide and a second heterologous polypeptide or other type of fusion or between two or more stabilized ActRIIB polypeptides. In one embodiment, the linker is made up of amino acids linked together by peptide bonds, preferably from 1 to 20 amino acids linked by peptide bonds, wherein the amino acids are selected from the 20 naturally occurring amino acids. One or more of these amino acids may be glycosylated, as is understood by those of skill in the art. In one embodiment, the 1 to 20 amino acids may be selected from glycine, alanine, proline, asparagine, glutamine, and lysine. In one embodiment, a linker is made up of a majority of amino acids that are sterically unhindered, such as glycine and alanine. Exemplary linkers are polyglycines (particularly $(Gly)_5$, $(Gly)_8$, poly(Gly-Ala), and polyalanines. One exemplary suitable linker as shown in the Examples below is $(Gly)_4Ser$ (SEQ ID NO: 25). In a further embodiment, svActRIIB can comprise a "hinge linker", that is a linker sequence provided adjacent to a hinge region or a partial hinge region of an IgG, as exemplified in SEQ ID NO: 27. Hinge sequences include IgG2Fc (SEQ ID NO: 28), IgG1Fc (SEQ ID NO: 29), and IgG4Fc (SEQ ID NO: 30).

Hinge linker sequences may also be designed to improve manufacturability and stability of the svActRIIB-Fc proteins. In one embodiment, the hinge linkers of SEQ ID NO: 27, 38, 40, 42, 44, 45, and 46 are designed to improve manufacturability with the IgG2 Fc (SEQ ID NO: 22) when attached to svActRIIB polypeptides. In one embodiment, the hinge linker sequences is designed to improve manufacturability when attaching svActRIIB polypeptides to a human IgG1 Fc (SEQ ID NO: 23) or a modified human IgG1 Fc (SEQ ID NO: 47), for example, the hinge linkers having SEQ ID NO: 48, SEQ ID NO: 49 and SEQ ID NO: 50. The improved manufacturability of these polypeptides is described below in Example 4.

Linkers may also be non-peptide linkers. For example, alkyl linkers such as —NH—$(CH_2)s$-C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc.

The svActRIIB polypeptides disclosed herein can also be attached to a non-polypeptide molecule for the purpose of conferring desired properties such as reducing degradation and/or increasing half-life, reducing toxicity, reducing immunogenicity, and/or increasing the biological activity of the svActRIIB polypeptides. Exemplary molecules include but are not limited to linear polymers such as polyethylene glycol (PEG), polylysine, a dextran; a lipid; a cholesterol group (such as a steroid); a carbohydrate, or an oligosaccharide molecule.

The svActRIIB proteins and polypeptides have improved manufacturability properties when compared to other ActRIIB soluble polypeptides. As used herein, the term "manufacturability" refers to the stability of a particular protein during recombinant expression and purification of that protein. Manufacturability is believed to be due to the intrinsic properties of the molecule under conditions of expression and purification. Examples of improved manufacturability characteristics are set forth in the Examples below and include uniform glycosylation of a protein (Example 2), increased cell titer, growth and protein expression during recombinant production of the protein (Example 1), improved purification properties (Example 2), and improved stability at low pH (Example 2). The svActRIIB proteins and polypeptides of the present invention demonstrate the improved manufacturability, along with retention of in vitro and in vivo activity (Examples 2 and 3), compared with other soluble ActRIIB polypeptides. Further, additional hinge linker sequences may confer additional manufacturability benefits, as shown in Example 4 below.

As used herein, the term a "svActRIIB polypeptide activity" or "a biological activity of a soluble ActRIIB polypeptide" refers to one or more in vitro or in vivo activities of the svActRIIB polypeptides including but not limited to those demonstrated in the Example below. Activities of the svActRIIB polypeptides include, but are not limited to, the ability to bind to myostatin or activin A or GDF-11, and the ability to inhibit or neutralize an activity of myostatin or activin A or GDF-11. As used herein, the term "capable of binding" to myostatin, activin A, or GDF-11 refers to binding measured by methods known in the art, such as the KinExA™ method shown in the Examples below. In vitro inhibition of myostatin, activin A, or GDF-11 can be measured using, for example, the pMARE C2C12 cell-based assay described in the Examples below. In vivo activity, demonstrated in Example 3 below, is demonstrated by increased lean muscle mass in mouse models. In vivo activities of the svActRIIB polypeptides and proteins include but are not limited to increasing body weight, increasing lean muscle mass, and increasing the ratio of lean muscle to fat mass. Therapeutic activities further include reducing or preventing cachexia caused by certain types of tumors, preventing the growth of certain types of tumors, and increasing survival of certain animal models. Further discussion of the svActRIIB protein and polypeptide activities is provided below.

In another aspect, the present invention provides an isolated nucleic acid molecule comprising a polynucleotide encoding an svActRIIB polypeptide of the present invention. As used herein the term "isolated" refers to nucleic acid molecules purified to some degree from endogenous material.

In one embodiment, the polynucleotide encodes a polypeptide having the sequence set forth in SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes a polypeptide having the sequence set forth in amino acids 19 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes a polypeptide having the sequence set forth in amino acids 23 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes a polypeptide having the sequence set forth in amino acids 25 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes the a polypeptide having an amino acid sequence at least 80%, 85%, 90%, 95%, 98% or 99% identity to any one of the polypeptides above, wherein the polypeptide has single amino acid substitution at position 28, and a single amino acid substitution at position 44, wherein the substitution at position 28 is selected from W or Y, and the substitution at position 44 is T, and wherein the polypeptide is capable of binding myostatin, activin A, or GDF-11. In one embodiment, the polynucleotide of the above embodiments encodes a polypeptide wherein the substitution at position 28 is W and the substitution at position 44 is T.

In one embodiment, the isolated nucleic acid molecule of the present invention comprises a polynucleotide encoding a polypeptide having the sequence set forth in the group consisting of SEQ ID NO: 4, 6, 12, and 14. In another embodiment, the nucleic acid comprises a polynucleotide encoding a polypeptide having at least 80%, 90%, 95%, 96%, 97%, 98%, 99% sequence identity to SEQ ID NO: 4, 6, 12 or 14, wherein the polypeptide has a W or Y at position 28 and a T at position 44, and wherein the polypeptide is capable of binding activin A, GDF-11, or myostatin. In one embodiment, the polynucleotide of the above embodiments encodes a polypeptide wherein the substitution at position 28 is W and the substitution at position 44 is T, and wherein the polypeptide is capable of binding activin A, GDF-11 or myostatin.

In another embodiment, the isolated nucleic acid molecule further comprises a polynucleotide encoding at least one heterologous protein. In one embodiment, the heterologous protein is an Fc domain, in a further embodiment, the Fc domain is a human IgG Fc domain. In another embodiment, the nucleic acid molecule further comprises polynucleotides encoding the linkers and hinge linkers set forth in SEQ ID NO: 25, 27, 38, 40, 42, 44, 45, 46, 48, 49 or 50. In a further embodiment, such polynucleotides have sequences selected from the group consisting of SEQ ID NO: 26, 37, 39, 41, and 43.

In one embodiment, the nucleic acid molecule comprises a polynucleotide encoding a polypeptide consisting of the sequence set forth in the group consisting of SEQ ID NO: 8, 10, 16 and 18. In another embodiment, the nucleic acid comprises a polynucleotide encoding a polypeptide having at least 80%, 90%, 95%, 96%, 97%, 98%, 99% sequence identity to the group consisting of SEQ ID NO: 8, 10, 16 and 18, wherein the polypeptide has a W or Y at position 28 and a T at position 44, and wherein the polypeptide is capable of binding activin A, GDF-11, or myostatin. In one embodiment, the polynucleotide of the above embodiments encodes a polypeptide wherein the substitution at position 28 is W and the substitution at position 44 is T, and wherein the polypeptide is capable of binding myostatin, activin A or GDF-11.

In one embodiment, the isolated nucleic acid molecule comprises a polynucleotide having the sequence selected from the group consisting of SEQ ID NO: 3, 5, 11 or 13, or its complement. In another embodiment, the isolated nucleic acid molecule comprises a polynucleotide having the sequence selected from the group consisting of the sequence SEQ ID NO: 7, 9, 15 and 17, or its complement. In a further embodiment the isolated nucleic acid molecule hybridizes under stringent or moderate conditions with SEQ ID NO: 3, 5, 7, 9, 11, 13, 15 or 17 wherein the encoded polypeptide is substantially similar to SEQ ID NO: 4, 6, 8, 10, 12, 14, 16, or 18, wherein the polypeptide comprises an amino acid sequence having W or Y at position 28, and T at position 44, and wherein the encoded polypeptide is capable of binding or inhibiting activin A, myostatin or GDF-11.

Nucleic acid molecules of the invention include DNA in both single-stranded and double-stranded form, as well as the RNA complement thereof. DNA includes, for example, cDNA, genomic DNA, synthetic DNA, DNA amplified by PCR, and combinations thereof. Genomic DNA may be isolated by conventional techniques, such as by using the DNA of SEQ ID NO: 3, 5, 11 or 13, or a suitable fragment thereof, as a probe. Genomic DNA encoding ActRIIB polypeptides is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from procaryotic expression vectors which direct high-level synthesis of mRNA, such as vectors using T7 promoters and RNA polymerase. cDNA is obtained from libraries prepared from mRNA isolated from various tissues that express ActRIIB. The DNA molecules of the invention include full length genes as well as polynucleotides and fragments thereof. The full length gene may also include sequences encoding the N-terminal signal sequence.

The invention further provides the nucleic acid molecule describe above, wherein the polynucleotide is operably linked to a transcriptional or translational regulatory sequence.

Exemplary Polynucleotide and Polypeptide Sequences.

svActRIIB (E28W, S44T) with Signal Sequence (SEQ ID NO: 3)
atggagtttgggctgagctgggttttcctcgttgctcttttaaga ggtgtccagtgtgagacacggtggtgcatctactacaacgccaac tgggagctggagcgcaccaaccagaccggcctggagcgctgcgaa ggcgagcaggacaagcggctgcactgctacgcctcctggcgcaac agctctggcaccatcgagctcgtgaagaagggctgctggctagat gacttcaactgctacgataggcaggagtgtgtggccactgaggag aaccccaggtgtacttctgctgctgtgagggcaacttctgcaac gagcgcttcactcatttgccagaggctgggggcccggaagtcacg tacgagccaccccgacagcccccacc svActRIIB (E28W, S44T) with Signal Sequence (SEQ ID NO: 4)
mefglswvflvallrgvqcetrwciyynanwelertnqtglerce geqdkrlhcyaswrnssgtielvkkgcwlddfncydrqecvatee npqvyfcccegnfcnerfthlpeaggpevtyeppptapt svActRIIB (E28W, S44T) without Signal Sequence (SEQ ID NO: 5)
gagacacggtggtgcatctactacaacgccaactgggagctggag cgcaccaaccagaccggcctggagcgctgcgaaggcgagcaggac aagcggctgcactgctacgcctcctggcgcaacagctctggcacc atcgagctcgtgaagaagggctgctggctagatgacttcaactgc tacgataggcaggagtgtgtggccactgaggagaaccccaggtg tacttctgctgctgtgagggcaacttctgcaacgagcgcttcact catttgccagaggctgggggcccggaagtcacgtacgagccaccc ccgacagcccccacc svActRIIB (E28W, S44T) without Signal Sequence (SEQ ID NO: 6)
etrwciyynanwelertnqtglercegeqdkrlhcyaswrnssgt ielvkkgcwlddfncydrqecvateenpqvyfcccegnfcnerft hlpeaggpevtyeppptapt svActRIIB-Fc (E28W, S44T) Polynucleotide Sequence with Signal Sequence (SEQ ID NO: 7)
atggagtttgggctgagctgggttttcctcgttgctcttttaagagg tgtccagtgtgagacacggtggtgcatctactacaacgccaactggg agctggagcgcaccaaccagaccggcctggagcgctgcgaaggcgag caggacaagcggctgcactgctacgcctcctggcgcaacagctctgg caccatcgagctcgtgaagaagggctgctggctagatgacttcaact gctacgataggcaggagtgtgtggccactgaggagaaccccaggtg tacttctgctgctgtgagggcaacttctgcaacgagcgcttcactca tttgccagaggctgggggcccggaagtcacgtacgagccacccccga cagcccccaccggaggggaggatctgtcgagtgccaccgtgccca gcaccacctgtggcaggaccgtcagtcttcctcttcccccaaaacc caaggacaccctcatgatctcccggacccctgaggtcacgtgcgtgg tggtggacgtgagccacgaagaccccgaggtccagttcaactggtac gtggacggcgtggaggtgcataatgccaagacaaagccacgggagga gcagttcaacagcacgttccgtgtggtcagcgtcctcaccgttgtgc accaggactggctgaacggcaaggagtacaagtgcaaggtctccaac aaaggcctcccagcccccatcgagaaaaccatctccaaaaccaaagg gcagccccgagaaccacaggtgtacaccctgcccccatcccgggagg agatgaccaagaaccaggtcagcctgacctgcctggtcaaaggcttc tatcccagcgacatcgccgtggagtgggagagcaatgggcagccgga gaacaactacaagaccacacctcccatgctggactccgacggctcct tcttcctctacagcaagctcaccgtggacaagagcaggtggcagcag gggaacgtcttctcatgctccgtgatgcatgaggctctgcacaacca ctacacgcagaagagcctctccctgtctccgggtaaa svActRIIB-Fc (E28W, S44T) Polypeptide Sequence with Signal Sequence (SEQ ID NO: 8)
mefglswvflvallrgvqcetrwciyynanwelertnqtglercege qdkrlhcyaswrnssgtielvkkgcwlddfncydrqecvateenpqv yfcccegnfcnerfthlpeaggpevtyeppptaptggggsvecppcp appvagpsvflfppkpkdtlmisrtpevtcvvvdvshedpevqfhwy vdgvevhnaktkpreeqfnstfrvvsvltvvhqdwlngkeykckvsn kglpapiektisktkgqprepqvytlppsreemtknqvsltclvkgf ypsdiavewesngqpennykttppmldsdgsfflyskltvdksrwqq gnvfscsvmhealhnhytqkslslspgk svActRIIB-Fc (E28W, S44T) Polynucleotide Sequence without Signal Sequence (SEQ ID NO: 9)
gagacacggtggtgcatctactacaacgccaactgggagctggagcg caccaaccagaccggcctggagcgctgcgaaggcgagcaggacaagc ggctgcactgctacgcctcctggcgcaacagctctggcaccatcgag ctcgtgaagaagggctgctggctagatgacttcaactgctacgatag gcaggagtgtgtggccactgaggagaaccccaggtgtacttctgct gctgtgagggcaacttctgcaacgagcgcttcactcatttgccagag gctgggggcccggaagtcacgtacgagccaccccgacagcccccac cggaggggaggatctgtcgagtgccaccgtgcccagcaccacctg tggcaggaccgtcagtcttcctcttcccccaaaacccaaggacacc ctcatgatctcccggaccctgaggtcacgtgcgtggtggtggacgt gagccacgaagaccccgaggtccagttcaactggtacgtggacggc gtggaggtgcataatgccaagacaaagccacgggaggagcagttcaac agcacgttccgtgtggtcagcgtcctcaccgttgtgcaccaggactg gctgaacggcaaggagtacaagtgcaaggtctccaacaaaggcctcc cagcccccatcgagaaaaccatctccaaaaccaaagggcagccccga gaaccacaggtgtaccctgcccccatcccgggaggagatgaccaa gaaccaggtcagcctgacctgcctggtcaaaggcttctatcccagcg acatcgccgtggagtgggagagcaatgggcagccggagaacaactac aagaccacacctcccatgctggactccgacggctccttcttcctcta cagcaagctcaccgtggacaagagcaggtggcagcaggggaacgtct tctcatgctccgtgatgcatgaggctctgcacaaccactacacgcag aagagcctctccctgtctccgggtaaa svActRIIB-Fc (E28W, S44T), Polypeptide Sequence without Signal Sequence (SEQ ID NO: 10)
etrwciyynanwelertnqtglercegeqdkrlhcyaswrnssgtie lvkkgcwlddfncydrqecvateenpqvyfcccegnfcnerfthlpe aggpevtyeppptaptggggsvecppcpappvagpsvflfppkpkdt lmisrtpevtcvvvdvshedpevqfnwyvdgvevhnaktkpreeqfn stfrvvsvltvvhqdwlngkeykckvsnkglpapiektisktkgqpr epqvytlppsreemtknqvsltclvkgfypsdiavewesngqpenny kttppmldsdgsfflyskltvdksrwqqgnvfscsvmhealhnhytq kslslspgk svActRIIB (E28Y, S44T) with Signal Sequence (SEQ ID NO: 11)
atggagtttgggctgagctgggttttcctcgttgctcttttaagagg tgtccagtgtgagacacggtactgcatctactacaacgccaactggg agctggagcgcaccaaccagaccggcctggagcgctgcgaaggcgag caggacaagcggctgcactgctacgcctcctggcgcaacagctctgg caccatcgagctcgtgaagaagggctgctggctagatgacttcaact gctacgataggcaggagtgtgtggccactgaggagaaccccaggtg tacttctgctgctgtgagggcaacttctgcaacgagcgcttcactca tttgccagaggctgggggcccggaagtcacgtacgagccaccccga cagcccccacc svActRIIB (E28Y,S44T) with Signal Sequence (SEQ ID NO: 12)
mefglswvflvallrgvqcetryciyynanwelertnqtglercege qdkrlhcyaswrnssgtielvkkgcwlddfncydrqecvateenpqv yfcccegnfcnerfthlpeaggpevtyeppptapt svActRIIB (E28Y,S44T) without Signal Sequence (SEQ ID NO: 13)
gagacacggtactgcatctactacaacgccaactgggagctggagcg caccaaccagaccggcctggagcgctgcgaaggcgagcaggacaagc ggctgcactgctacgcctcctggcgcaacagctctggcaccatcgag ctcgtgaagaagggctgctggctagatgacttcaactgctacgatag gcaggagtgtgtggccactgaggagaaccccaggtgtacttctgct gctgtgagggcaacttctgcaacgagcgcttcactcatttgccagag gctgggggcccggaagtcacgtacgagccaccccgacagcccccac c svActRIIB (E28Y,S44T) without Signal Sequence (SEQ ID NO: 14)
etryciyynanwelertnqtglercegeqdkrlhcyaswrnssgtie lvkkgcwlddfncydrqecvateenpqvyfcccegnfcnerfthlpe aggpevtyeppptapt svActRIIB-Fc (E28Y, S44T) Polynucleotide Sequence with Signal Sequence (SEQ ID NO: 15)
atggagtttgggctgagctgggttttcctcgttgctcttttaagagg tgtccagtgtgagacacggtactgcatctactacaacgccaactggg agctggagcgcaccaaccagaccggcctggagcgctgcgaaggcgag caggacaagcggctgcactgctacgcctcctggcgcaacagctctgg caccatcgagctcgtgaagaagggctgctggctagatgacttcaact gctacgataggcaggagtgtgtggccactgaggagaaccccaggtg tacttctgctgctgtgagggcaacttctgcaacgagcgcttcactca tttgccagaggctggggcccggaagtcacgtacgagccaccccga cagcccccaccggaggggaggatctgtcgagtgcccaccgtgccca gcaccacctgtggcaggaccgtcagtcttcctcttccccccaaaacc caaggacaccctcatgatctcccggacccctgaggtcacgtgcgtgg tggtggacgtgagccacgaagaccccgaggtccagttcaactggtac gtggacggcgtggaggtgcataatgccaagacaaagccacgggagga gcagttcaacgcacgttccgtgtggtcagcgtcctcaccgttgtgc accaggactggctgaacggcaaggagtacaagtgcaaggtctccaac aaaggcctcccagcccccatcgagaaaaccatctccaaaaccaaagg gcagccccgagaaccacaggtgtacaccctgcccccatcccgggagg agatgaccaagaaccaggtcagcctgacctgcctggtcaaaggcttc tatcccagcgacatcgccgtggagtgggagagcaatgggcagccgga gaacaactacaagaccacacctcccatgctggactccgacggctcct tcttcctctacagcaagctcaccgtggacaagagcaggtggcagcag gggaacgtcttctcatgctccgtgatgcatgaggctctgcacaacca ctacacgcagaagagcctctccctgtctccgggtaaa svActRIIB-Fc (E28Y, S44T) Polypeptide Sequence with Signal Sequence (SEQ ID NO: 16)
mefglswvflvallrgvqcetryciyynanwelertnqtglercege qdkrlhcyaswrnssgtielvkkgcwlddfncydrqecvateenpqv yfcccegnfcnerfthlpeaggpevtyeppptaptggggsvecppcp appvagpsvflfppkpkdtlmisrtpevtcvvvdvshedpevqfnwy vdgvevhnaktkpreeqfnstfrvvsvltvvhqdwlngkeykckvsn kglpapiektisktkgqprepqvytlppsreemtknqvsltclvkgf ypsdiavewesngqpennykttppmldsdgsfflyskltvdksrwqq gnvfscsvmhealhnhytqkslslspgk svActRIIB-Fc (E28Y, S44T) Polynucleotide Sequence without Signal Sequence (SEQ ID NO: 17)
gagacacggtactgcatctactacaacgccaactgggagctggagcg caccaaccagaccggcctggagcgctgcgaaggcgagcaggacaagc ggctgcactgctacgcctcctggcgcaacagctctggcaccatcgag ctcgtgaagaagggctgctggctagatgacttcaactgctacgatag gcaggagtgtgtggccactgaggagaaccccaggtgtacttctgct gctgtgagggcaacttctgcaacgagcgcttcactcatttgccagag gctggggcccggaagtcacgtacgagccaccccgacagcccccac cggaggggaggatctgtcgagtgcccaccgtgcccagcaccacctg tggcaggaccgtcagtcttcctcttccccccaaaacccaaggacacc ctcatgatctcccggacccctgaggtcacgtgcgtggtggtggacgt gagccacgaagaccccgaggtccagttcaactggtacgtggacggcg tggaggtgcataatgccaagacaaagccacgggaggagcagttcaac agcacgttccgtgtggtcagcgtcctcaccgttgtgcaccaggactg gctgaacggcaaggagtacaagtgcaaggtctccaacaaaggcctcc cagcccccatcgagaaaaccatctccaaaaccaaagggcagccccga gaaccacaggtgtacaccctgcccccatcccgggaggagatgaccaa gaaccaggtcagcctgacctgcctggtcaaaggcttctatcccagcg acatcgccgtggagtgggagagcaatgggcagccggagaacaactac aagaccacacctcccatgctggactccgacggctccttcttcctcta cagcaagctcaccgtggacaagagcaggtggcagcaggggaacgtct tctcatgctccgtgatgcatgaggctctgcacaaccactacacgcag aagagcctctccctgtctccgggtaaa svActRIIB-Fc (E28Y, S44T) Polypeptide Sequence without Signal Sequence (SEQ ID NO: 18)
etryciyynanwelertnqtglercegeqdkrlhcyaswrnssgtie lvkkgcwlddfncydrqecvateenpqvyfcccegnfcnerfthlpe aggpevtyeppptaptggggsvecppcpappvagpsvflfppkpkdt lmisrtpevtcvvvdvshedpevqfnwyvdgvevhnaktkpreeqfn stfrvvsvltvvhqdwingkeykckvsnkglpapiektisktkgqpr epqvytlppsreemtknqvsltclvkgfypsdiavewesngqpenny kttppmldsdgsfflyskltvdksrwqqgnvfscsvmhealhnhytq kslslspgk In another aspect of the present invention, expression vectors containing the nucleic acid molecules and polynucleotides of the present invention are also provided, and host cells transformed with such vectors, and methods of producing the svActRIIB polypeptides are also provided.

The term "expression vector" refers to a plasmid, phage, virus or vector for expressing a polypeptide from a polynucleotide sequence. Vectors for the expression of the svActRIIB polypeptides contain at a minimum sequences required for vector propagation and for expression of the cloned insert. An expression vector comprises a transcriptional unit comprising an assembly of (1) a genetic element or elements having a regulatory role in gene expression, for example, promoters or enhancers, (2) a sequence that encodes svActRIIB polypeptides and proteins to be transcribed into mRNA and translated into protein, and (3) appropriate transcription initiation and termination sequences. These sequences may further include a selection marker. Vectors suitable for expression in host cells are readily available and the nucleic acid molecules are inserted into the vectors using standard recombinant DNA techniques. Such vectors can include promoters which function in specific tissues, and viral vectors for the expression of svActRIIB polypeptides in targeted human or animal cells. An exemplary expression vector suitable for expression of svActRIIB is the pDSRa, (described in WO 90/14363, herein incorporated by reference) and its derivatives, containing svActRIIB polynucleotides, as well as any additional suitable vectors known in the art or described below.

The invention further provides methods of making svActRIIB polypeptides. A variety of other expression/host systems may be utilized. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells useful in recombinant protein production include but are not limited to VERO cells, HeLa cells, Chinese hamster ovary (CHO) cell lines, or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20) COS cells such as the COS-7 line of monkey kidney cells (ATCC CRL 1651) (see Gluzman et al., 1981, Cell 23:175), W138, BHK, HepG2, 3T3 (ATCC CCL 163), RIN, MDCK, A549, PC12, K562, L cells, C127 cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Mammalian expression allows for the production of secreted or soluble polypeptides which may be recovered from the growth medium.

Using an appropriate host-vector system, svActRIIB polypeptides are produced recombinantly by culturing a host cell transformed with an expression vector containing the nucleic acid molecules of the present invention under conditions allowing for production. Transformed cells can be used for long-term, high-yield polypeptide production. Once such cells are transformed with vectors that contain selectable markers as well as the desired expression cassette, the cells can be allowed to grow in an enriched media before they are switched to selective media, for example. The selectable marker is designed to allow growth and recovery of cells that successfully express the introduced sequences. Resistant clumps of stably transformed cells can be proliferated using tissue culture techniques appropriate to the cell line employed. An overview of expression of recombinant proteins is found in Methods of Enzymology, v. 185, Goeddell, D. V., ed., Academic Press (1990).

In some cases, such as in expression using procaryotic systems, the expressed polypeptides of this invention may need to be "refolded" and oxidized into a proper tertiary structure and disulfide linkages generated in order to be biologically active. Refolding can be accomplished using a number of procedures well known in the art. Such methods include, for example, exposing the solubilized polypeptide to a pH usually above 7 in the presence of a chaotropic agent. The selection of chaotrope is similar to the choices used for inclusion body solubilization, however a chaotrope is typically used at a lower concentration. Exemplary chaotropic agents are guanidine and urea. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

In addition, the polypeptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d.Ed., Pierce Chemical Co. (1984); Tam et al., J Am Chem Soc, 105:6442, (1983); Merrifield, Science 232:341-347 (1986); Barany and Merrifield, *The Peptides*, Gross and Meienhofer, eds, Academic Press, New York, 1-284; Barany et al., Int J Pep Protein Res, 30:705-739 (1987).

The polypeptides and proteins of the present invention can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography, isoelectric focusing, gel electrophoresis, and combinations of these techniques. As is generally known in the art, it is believed that the order of conducting the various purification steps may be changed, or that certain steps may be omitted, and still result in a suitable method for the preparation of a substantially purified polypeptide. Exemplary purification steps are provided in the Examples below.

Various methods for quantifying the degree of purification of polypeptide will be known to those of skill in the art in light of the present disclosure. These include, for example, determining the specific binding activity of an active fraction, or assessing the amount of peptide or polypeptide within a fraction by SDS/PAGE analysis. A preferred method for assessing the purity of a polypeptide fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the polypeptide or peptide exhibits a detectable binding activity.

Stabilized activin type IIB polypeptides bind to ligands that activate muscle-degradation cascades. svActRIIB polypeptides capable of binding and inhibiting the activity of the ligands activin A, myostatin, and/or GDF-11, and have the ability to treat diseases that involve muscle atrophy, as well as the treatment of certain cancers, and other diseases.

The Examples below show improved properties for svActRIIB polypeptides and proteins having the amino acid substitutions described herein, while retaining the ability to bind and neutralize myostatin, activin A, or GDF-11 in in vitro assays, as well as retaining in vivo activity. These properties result in proteins and polypeptides having improved manufacturability in comparison to other soluble receptors.

Antibodies

The present invention further includes antibodies which bind to stabilized ActRIIB polypeptides, including those that specifically bind to the svActRIIB polypeptides of the present invention. As used herein the term "specifically binds" refers to antibodies having a binding affinity ($K_a$) for svActRIIB polypeptides of $10^6$ M$^{-1}$ or greater. As used herein, the term "antibody" refers to intact antibodies including polyclonal antibodies (see, for example Antibodies: A Laboratory Manual, Harlow and Lane (eds), Cold Spring Harbor Press, (1988)), and monoclonal antibodies (see, for example, U.S. Pat. Nos. RE 32,011, 4,902,614, 4,543,439, and 4,411,993, and Monoclonal Antibodies: A New Dimension in Biological Analysis, Plenum Press, Kennett, McKearn and Bechtol (eds.) (1980)). As used herein, the term "antibody" also refers to a fragment of an antibody such as F(ab), F(ab'), F(ab')$_2$, Fv, Fc, and single chain antibodies which are produced by recombinant DNA techniques or by enzymatic or chemical cleavage of intact antibodies. The term "antibody" also refers to bispecific or bifunctional antibodies, which are an artificial hybrid antibody having two different heavy/light chain pairs and two different binding sites. Bispecific antibodies can be produced by a variety of methods including fusion of hybridomas or linking of Fab' fragments. (See Songsivilai et al, Clin. Exp. Immunol. 79:315-321 (1990), Kostelny et al., J. Immunol. 148:1547-1553 (1992)).

As used herein the term "antibody" also refers to chimeric antibodies, that is, antibodies having a human constant antibody immunoglobin domain coupled to one or more non-human variable antibody immunoglobin domain, or fragments thereof (see, for example, U.S. Pat. Nos. 5,595,898 and 5,693,493). Antibodies also refers to "humanized" antibodies (see, for example, U.S. Pat. No. 4,816,567 and WO 94/10332), minibodies (WO 94/09817), maxibodies, and antibodies produced by transgenic animals, in which a transgenic animal containing a proportion of the human antibody producing genes but deficient in the production of endogenous antibodies are capable of producing human antibodies (see, for example, Mendez et al., Nature Genetics 15:146-156 (1997), and U.S. Pat. No. 6,300,129). The term "antibodies" also includes multimeric antibodies, or a higher order complex of proteins such as heterdimeric antibodies, and anti-idiotypic antibodies. "Antibodies" also includes anti-idiotypic antibodies. The antibodies against sv ActRIIB polypeptides can be used, for example, to identify and quantitate svActRIIB in vitro and in vivo.

Also included are polyclonal antibodies from any mammal, for example mouse and rat antibodies, and rabbit antibodies, that bind specifically to the svActRIIB polypeptides described herein.

Such antibodies find use as research tools and in quantitative assays for detecting and assaying the polypeptides disclosed herein. Such antibodies are made using methods described above and as known in the art.

Pharmaceutical Compositions

Pharmaceutical compositions containing the svActRIIB proteins and polypeptides of the present invention are also provided. Such compositions comprise a therapeutically or prophylactically effective amount of the polypeptide or protein in admixture with pharmaceutically acceptable materials, and physiologically acceptable formulation materials. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents;

surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18$^{th}$ Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffers, or acetate buffers, which may further include sorbitol or a suitable substitute thereof. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

The formulations can be delivered in a variety of methods, for example, by inhalation therapy, orally, or by injection. When parenteral administration is contemplated, the therapeutic compositions for use in this invention may be in the form of a pyrogen-free, parenterally acceptable aqueous solution comprising the desired polypeptide in a pharmaceutically acceptable vehicle. A particularly suitable vehicle for parenteral injection is sterile distilled water in which a polypeptide is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. Inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the therapeutic molecule. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly(2-hydroxyethyl-methacrylate) (Langer et al., J. Biomed. Mater. Res., 15:167-277, (1981); Langer et al., Chem. Tech., 12:98-105(1982)), ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, the svActRIIB polypeptides of the present invention can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the polypeptide product(s) but prevent the destruction of the cells by the patient's immune system or by other detrimental factors from the surrounding tissues.

svActRIIB gene therapy in vivo is also envisioned wherein a nucleic acid molecule encoding svActRIIB, or a derivative of svActRIIB is introduced directly into the subject. For example, a nucleic acid sequence encoding a svActRIIB is introduced into target cells via local injection of a nucleic acid construct with or without an appropriate delivery vector, such as an adeno-associated virus vector. Alternative viral vectors include, but are not limited to, retroviruses, adenovirus, herpes simplex, virus and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Uses of svActRIIB Compositions

The present invention provides methods and pharmaceutical compositions for reducing or neutralizing the amount or activity of myostatin, activin A, or GDF-11 in vivo and in vitro. svActRIIB polypeptides have a high binding affinity for myostatin, activin A, and GDF-11, and are capable of reducing and inhibiting the biological activities of at least one of myostatin, activin A and GDF-11.

In one aspect, the present invention provides methods and reagents for treating myostatin-related and/or activin A related disorders in a subject in need of such a treatment by administering an effective dosage of an svActRIIB composition to the subject. As used herein the term "subject" refers to any animal, such as mammals including humans.

The compositions of the present invention are useful for increasing lean muscle mass in a subject. The compositions may also be useful to increase lean muscle mass in proportion to fat mass, and thus decrease fat mass as percentage of body weight in a subject. Example 3 demonstrates that the svActRIIB polypeptides and proteins of the invention can increase lean muscle mass in animals.

The disorders that can be treated by an svActRIIB composition include but are not limited to various forms of muscle wasting, as well as metabolic disorders such as diabetes and related disorders, and bone degenerative diseases such as osteoporosis.

Muscle wasting disorders also include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. Additional muscle wasting disorders arise from chronic diseases or disorders such as amyotrophic lateral sclerosis, congestive obstructive pulmonary disease, cancer, AIDS, renal failure, organ atrophy, androgen deprivation, and rheumatoid arthritis.

Over-expression of myostatin and/or activin may contribute to cachexia, a severe muscle wasting syndrome. Cachexia results from cancers, and also arises due to rheumatoid arthritis, diabetic nephropathy, renal failure, chemotherapy, injury due to burns, as well as other causes. In another example, serum and intramuscular concentrations of myostatin-immunoreactive protein was found to be increased in men exhibiting AIDS-related muscle wasting and was inversely related to fat-free mass (Gonzalez-Cadavid et al., PNAS USA 95: 14938-14943 (1998)). Myostatin levels have also been shown to increase in response to burns injuries, resulting in a catabolic muscle effect (Lang et al, FASEB J 15, 1807-1809 (2001)). Additional conditions resulting in muscle wasting may arise from inactivity due to disability such as confinement in a wheelchair, prolonged bed rest due to stroke, illness, spinal chord injury, bone fracture or trauma, and muscular atrophy in a microgravity environment (space flight). For example, plasma myostatin immunoreactive protein was found to increase after prolonged bed rest (Zachwieja et al. J Gravit Physiol. 6(2):11 (1999). It was also found that the muscles of rats exposed to a microgravity environment during a space shuttle flight expressed an increased amount of myostatin compared with the muscles of rats which were not exposed (Lalani et al., J. Endocrin 167 (3):417-28 (2000)).

In addition, age-related increases in fat to muscle ratios, and age-related muscular atrophy appear to be related to myostatin. For example, the average serum myostatin-immunoreactive protein increased with age in groups of young (19-35 yr. old), middle-aged (36-75 yr. old), and elderly (76-92 yr old) men and women, while the average muscle mass and fat-free mass declined with age in these groups (Yarasheski et al. J Nutr Aging 6(5):343-8 (2002)). In addition, myostatin has now been found to be expressed at low levels in heart muscle and expression is upregulated in cardiomyocytes after infarct (Sharma et al., J Cell Physiol. 180 (1):1-9 (1999)). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen et al. FASEB J. 8:479 (1994). The svActRIIB polypeptides of the present disclosure are suitable for treating such metabolic disorders. Therefore, administering the compositions of the present invention will improve diabetes, obesity, and hyperglycemic conditions in suitable subjects. In addition, compositions containing the svActRIIB polypeptides may decrease food intake in obese individuals.

Administering the stabilized ActRIIB polypeptides of the present invention may improve bone strength and reduce osteoporosis and other degenerative bone diseases. It has been found, for example, that myostatin-deficient mice showed increased mineral content and density of the mouse humerus and increased mineral content of both trabecular and cortical bone at the regions where the muscles attach, as well as increased muscle mass (Hamrick et al. Calcif Tissue Int 71(1):63-8 (2002)). In addition, the svActRIIB compositions of the present invention can be used to treat the effects of androgen deprivation in cases such as androgen deprivation therapy used for the treatment of prostate cancer, for example.

The present invention also provides methods and compositions for increasing muscle mass in food animals by administering an effective dosage of the svActRIIB proteins to the animal. Since the mature C-terminal myostatin polypeptide is similar or identical in all species tested, svActRIIB polypeptides would be expected to be effective for increasing lean muscle mass and reducing fat in any agriculturally important species including cattle, chicken, turkeys, and pigs.

The svActRIIB polypeptides and compositions of the present invention also antagonize the activity of activin A, as shown in the in vitro assays below. Activin A is known to be expressed in certain types of cancers, particularly gonadal tumors such as ovarian carcinomas, and to cause severe cachexia. (Ciprano et al. Endocrinol 141 (7):2319-27 (2000), Shou et al., Endocrinol 138 (11):5000-5 (1997); Coerver et al, Mol Endocrinol 10(5):534-43 (1996); Ito et al. British J Cancer 82(8):1415-20 (2000), Lambert-Messerlian, et al, Gynecologic Oncology 74:93-7 (1999). Therefore, the compositions of the present disclosure may be used to treat conditions related to activin A overexpression, as well as myostatin expression, such as cachexia from certain cancers and the treatment of certain gonadal type tumors.

In addition, the svActRIIB polypeptides of the present invention are useful for detecting and quantitating myostatin, activin A, or GDF-11 in any number of assays. In general, the stabilized ActRIIB polypeptides of the present invention are useful as capture agents to bind and immobilize myostatin, activin A, or GDF-11 in a variety of assays, similar to those described, for example, in Asai, ed., Methods in Cell Biology, 37, *Antibodies in Cell Biology*, Academic Press, Inc., New York (1993). The polypeptides may be labeled in some manner or may react with a third molecule such as an antibody which is labeled to enable myostatin to be detected and quantitated. For example, a polypeptide or a third molecule can be modified with a detectable moiety, such as biotin, which can then be bound by a fourth molecule, such as enzyme-labeled streptavidin, or other proteins. (Akerstrom, *J Immunol* 135:2589 (1985); Chaubert, *Mod Pathol* 10:585 (1997)).

Example 1

Expression and Purification of svActRIIB Polypeptides

The following methods were used for expressing and purifying the stabilized ActRIIB polypeptides.

The cDNA of the human activin type IIB receptor was isolated from a cDNA library of human testis origin (Clontech, Inc.) and cloned as described in U.S. application Ser. No. 11/590,962, U.S. application publication No: 2007/0117130, which is herein incorporated by reference.

The following method was used to produce the svActRIIB-Fc (E28W, S44T) polypeptide (SEQ ID NO: 10), and the ActRIIB-Fc (E28W) (SEQ ID NO: 21). Polynucleotides encoding the svActRIIB, (E28W, S44T) (SEQ ID NO: 5), or polynucleotides encoding ActRIIB (E28W) (SEQ ID NO: 19) were fused to polynucleotides encoding the human IgG2 Fc (SEQ ID NO: 22), via polynucleotides encoding hinge linker sequence (SEQ ID NO: 26) using PCR overlap extension using primers containing the mutation resulting in the amino acid substitutions at position 28 of E to W, and at position 44 of S to T. The full polynucleotide sequence is SEQ ID NO: 9 for svActRIIB-IgG Fc (E28W, S44T), and SEQ ID NO: 20 for ActRIIB-ActRIIB-IgG Fc (E28W). Double stranded DNA fragments were subcloned into vectors pTT5 (Biotechnology Research Institute, National Research Council Canada (NRCC), 6100 Avenue Royalmount, Montréal (Québec) Canada H4P 2R2), pDSRα□□ described in WO/9014363) and/or derivatives of pDSRα.

Transient expression of stabilized ActRIIB-Fc polypeptides was carried out as follows.

The svActRIIB-IgG Fc (E28W, S44T) (SEQ ID NO: 10), and ActRIIB-IgG Fc (E28W) (SEQ ID NO: 21) polypeptides were expressed transiently in serum-free suspension adapted 293-6E cells (National Research Council of Canada, Ottawa, Canada) maintained in FreeStyle™ medium (Invitrogen Corporation, Carlsbad, Calif.) supplemented with 250 µg/ml geneticin (Invitrogen) and 0.1% Pluronic F68 (Invitrogen). Transfections were performed as 1 L cultures. Briefly, the cell inoculum was grown to $1.1 \times 10^6$ cells/ml in a 4 L fernbach shake flask (Corning, Inc.). The shake flask culture was maintained on an Innova 2150 shaker platform (News Brunswick Scientific, Edison, N.J.) at 65 RPM which was placed in a humidified incubator maintained at 37° C. and 5% $CO_2$. At the time of transfection, the 293-6E cells were diluted to $1.0 \times 10^6$ cells/ml.

The transfection complexes were formed in 100 ml FreeStyle™ 293 Media (Invitrogen). 1 mg plasmid DNA was first added to the medium followed by 3 ml of FuGene HD transfection reagent (Roche Applied Science, Indianapolis, Ind.). The transfection complex was incubated at room temperature for approximately 15 minutes and then added to the cells in the shake flask. Twenty hours post transfection, 20% (w/v) of peptone TN1 (OrganoTechnie S.A., TeknieScience, QC, Canada) was added to reach a final concentration of 0.5% (w/v). The transfection/expression was performed for 4-7 days, after which the conditioned medium was harvested by centrifugation at 4,000 RPM for 60 minutes at 4° C.

Stable transfection and expression was carried out as follows. The svActRIIB-IgG-Fc cell lines were created by transfecting stable CHO host cells with the expression plasmids containing polynucleotides encoding svActRIIB-IgG Fc (E28W, S44T) (SEQ ID NO: 9) or ActRIIB-IgG Fc (E28W) (SEQ ID NO: 20) using a standard electroporation procedure. After transfection of the host cell line with the expression plasmids the cells were grown in serum-free selection medium without GHT for 2-3 weeks to allow for selection of the plasmid and recovery of the cells. Cells are selected until they achieved greater than 85% viability. This pool of transfected cells was then cultured in medium containing 150 nM methotrexate.

In a six-day expression assay, pools of svActRIIB-Fc (E28W, S44T) expressing cells showed higher cell titer, growth performance, and improved specific productivity (picogram/cell/day) of protein produced compared with pools of ActRIIB-Fc (E28W) expressing cells. Select pools, for example, produced about 1.2 g/liter for svActRIIB-Fc (E28W, S44T) compared with 0.9 g/liter for ActRIIB-Fc (E28W).

Each of an svActRIIB-Fc (E28W, S44T) and an ActRIIB-Fc (E28W) expressing cell line was scaled up using a typical fed-batch process. Cells were inoculated into a Wave bioreactor (Wave Biotech LLC). Cultures were fed three times with bolus feeds. 10 L were harvested on day 10, the remainder was harvested on day 11; both harvests underwent depth filtration followed by sterile filtration. The conditioned media was filtered through a 10 inch 0.45/0.2 micron pre filter, followed by a filtration through a 6 inch 0.2 micron filter.

Protein Purification

Approximately 5 L of conditioned media was directly loaded onto a 220 mL MabSelect™ column Protein A column (GE Healthcare). The column was pre-equilibrated in PBS (phosphate-buffered saline: 2.67 mM potassium chloride, 138 mM sodium chloride, 1.47 mM potassium phosphate monobasic, 8.1 mM sodium phosphate dibasic, pH 7.4). The column was washed with the equilibration buffer until the reading at OD280 was approximately zero, and then the protein was eluted with 0.1M acetic acid.

The Mabselect™ Pool was applied to a 300 mL SP-HP column (GE Healthcare) (5×15 cm). The column was pre-equilibrated with 10 mM NaOAC, pH 5. The column was then washed with the equilibration buffer until the reading at OD280 was approximately 0. The column was eluted with 20 column volumes of a gradient buffer from 0-150 mM NaCl in 10 mM NaOAC, pH 5. The SP-HP pool was concentrated, and filtered with a 0.2 uM cellulose acetate (Corning) filter.

The sequences of the proteins used are set forth in the Table below.

| ActRIIB-Fc | ActRIIB sequence | Linker-Hinge | IgG2 Fc |
|---|---|---|---|
| svActRIIB-IgG₂Fc (E28W, S44T) (SEQ ID NO: 10) | ETRWCIYYNANWEL ERTNQTGLERCEGE QDKRLHCYASWRNS SGTIELVKKGCWLD DFNCYDRQECVATE ENPQVYFCCCEGNF CNERFTHLPEAGGP EVTYEPPPTAPT (SEQ ID NO: 6) | GGGGSVE CPPCP (SEQ ID NO: 27) | APPVAGPSVFLFPPK PKDTLMISRTPEVTC VVVDVSHEDPEVQFN WYVDGVEVHNAKTKP REEQFNSTFRVVSVL TVVHQDWLNGKEYKC KVSNKGLPAPIEKTI SKTKGQPREPQVYTL PPSREEMTKNQVSLT CLVKGFYPSDIAVEW ESNGQPENNYKTTPP MLDSDGSFFLYSKLT |

-continued

| ActRIIB-Fc | ActRIIB sequence | Linker-Hinge | IgG2 Fc |
|---|---|---|---|
| | | | VDKSRWQQGNVFSCS VMHEALHNHYTQKSL SLSPGK (SEQ ID NO: 22) |
| ActRIIB-IgG₂Fc (E28W) (SEQ ID NO: 21) | ETRWCIYYNANWEL ERTNQSGLERCEGE QDKRLHCYASWRNS SGTIELVKKGCWLD DFNCYDRQECVATE ENPQVYFCCCEGNF CNERFTHLPEAGGP EVTYEPPPTAPT (SEQ ID NO: 19) | GGGGSVE CPPCP (SEQ ID NO: 27) | APPVAGPSVFLPPPK PKDTLMISRTPEVTC VVVDVSHEDPEVQFN WYVDGVEVHNAKTKP REEQFNSTFRVVSVL TVVHQDWLNGKEYKC KVSNKGLPAPIEKTI SKTKGQPREPQVYTL PPSREEMTKNQVSLT CLVKGFYPSDIAVEW ESNGQPENNYKTTPP MLDSDGSFFLYSKLT VDKSRWQQGNVFSCS VMHEALHNHYTQKSL SLSPGK (SEQ ID NO: 22) |

Example 2

Characterization of Polypeptides

Samples of the svActRIIB-Fc (E28W, S44T) (SEQ ID NO: 10) purified through the MabSelect™ step, and ActRIIB-Fc (E28W) (SEQ ID NO: 21) polypeptides purified through the SP-HP column step, as described above, were diluted with PBS, pH 7.4 to 0.2 mg/ml. The glycosylation profile of the polypeptides were then determined using SEC as described below.

Size Exclusion Chromatography (SEC).

Experiments were performed on an Agilent 1100 HPLC system with two columns (TOSOHAAS G3000swxl, 7.8× 300 mm) in tandem. 2×PBS was used as the mobile phase at 0.5 ml/minute.

FIG. 1 shows a comparison between ActRIIB-Fc (E28W) and svActRIIB-Fc (E28W, S44T) on an SEC column using the protocols described above. svActRIIB-Fc (E28W, S44T) shows a single peak compared with ActRIIB-Fc (E28W), which shows three peaks. These correspond to the degree of N-linked glycosylation at the N42 position of the Fc dimers of both proteins. The single peak of the svActRIIB-Fc (E28W, S44T) polypeptide corresponds to fully glycosylated N-linked asparagines at position N42 of the dimer. The three peaks of ActRIIB-Fc (E28W) corresponds to (from left to right), fully glycosylated asparagines at N42, partially glycosylated asparagines at N42, and non-glycosylated asparagines at N42. Therefore, this demonstrates that the svActRIIB-Fc (E28W, S44T) molecule is fully glycosylated compared to ActRIIB-Fc (E28W), which is heterogeneous with respect to this glycosylation site, and thus more difficult to purify. In addition, preliminary studies indicate that the svActRIIB-Fc (E28W, S44T) molecule has addition improved manufacturability properties as set forth below. Additional studies also demonstrated that the least glycosylated peak of the ActRIIB-Fc (E28W) has lower physical and thermal stability than partially and fully glycosylated molecules.

Determination of $K_D$ and $IC_{50}$ values of the receptor polypeptides for activin A, myostatin, and GDF-11 were obtained as described below.

KinEx A™ Equilibrium Assays

Solution-based equilibrium-binding assays using KinExA™ technology (Sapidyne Instruments, Inc.) were used to determine the dissociation equilibrium ($K_D$) of ligand binding to ActRIIB-Fc polypeptides. UltraLink Biosupport beads (Pierce) was pre-coated with about 100 μg/ml each of myostatin, GDF-11, and activin A overnight, and then blocked with BSA. 1 pM and 3 pM of ActRIIB-Fc (E28W) (SEQ ID NO: 21) and svActRIIB-Fc (E28W, S44T) (SEQ ID NO: 10) samples were incubated with various concentrations (0.7 fM to 160 pM) of myostatin, activin A, and GDF-11 respectively in sample buffer at room temperature for 8 hours before being run through the ligand-coated beads. The amount of the bead-bound soluble receptor was quantified by fluorescent (Cy5) labeled goat anti-human-Fc antibody at 1 mg/ml in superblock. The binding signal is proportional to the concentration of free soluble receptor at equilibrium with a given myostatin, activin A, or GDF-11 concentration. $K_D$ was obtained from the nonlinear regression of the competition curves using a dual-curve one-site homogeneous binding model provided in the KinEx ATM software (Sapidyne Instruments, Inc.). The $K_D$ values obtained for each are given in the table below.

| | Myostatin | GDF-11 | Activin A |
|---|---|---|---|
| ActRIIB-Fc (E28W) | 0.1 pM | 0.1 pM | 0.2 pM |
| svActRIIB-Fc (E28W, S44T) | 0.1 pM | 0.1 pM | 0.1 pM |

C2C12 Cell Based Activity Assay

The ability of ActRIIB-Fc (E28W) (SEQ ID NO: 21) and svActRIIB-Fc (E28W, S44T) (SEQ ID NO: 10) to inhibit the binding of activin A, GDF-11, or myostatin to the wild type activin JIB receptor-Fc was tested using a cell based activity assay as described below.

A myostatin/activin/GDF-11-responsive reporter cell line was generated by transfection of C2C12 myoblast cells (ATCC No: CRL-1772) with a pMARE-luc construct. The pMARE-luc construct is made by cloning twelve repeats of the CAGA sequence, representing the myostatin/activin response elements (Dennler et al. EMBO 17: 3091-3100 (1998)) into a pLuc-MCS reporter vector (Stratagene cat #219087) upstream of the TATA box. The C2C12 cells naturally express activin receptor IIB on their cell surface. When myostatin/activinA/GDF-11 binds the cell receptors, the Smad pathway is activated, and phosphorylated Smad binds to the response element (Macias-Silva et al. Cell 87:1215 (1996)), resulting in the expression of the luciferase gene. Luciferase activity was then measured using a commercial luciferase reporter assay kit (cat # E4550, Promega, Madison, Wis.) according to manufacturer's protocol. A stable line of C2C12 cells that has been transfected with pMARE-luc (C2C12/pMARE) was used to measure activity according to the following procedure. Reporter cells were plated into 96 well cultures. Screening using dilutions of the ActRIIB-IgG2 Fc fusions constructed as described above was performed with the concentration fixed at 4 nM activin A, myostatin, and GDF-11. Each of these ligands was pre-incubated with the receptors at several concentrations. Activity was measured by determining the luciferase activity in the treated cultures. The $IC_{50}$ values were determined for each polypeptide. These are shown in the Table below. These values are given in Table below.

|  | Myostatin | GDF-11 | Activin A |
|---|---|---|---|
| ActRIIB-Fc (E28W) | 0.95 nM | 2.4 nM | 3.2 nM |
| svActRIIB-Fc (E28W, S44T) | 1.07 nM | 2.4 nM | 3.6 nM |

Thus the cell based activities are approximately the same for ActRIIB-Fc (E28W) and svActRIIB-Fc (E28W, S44T).

Stability at Low pH

Stability of a protein at low pH is a useful parameter in considering the manufacturability of the protein, since the viral inactivation step of a commercial production process typically is carried out at low pH, such as between about pH 3.0 to 4.0.

To assess the short term protein stability effects at low pH experienced during the viral inactivation step of commercial protein purification the following test was performed. Each protein was diluted to 10 mg/ml of 100 mM sodium acetate, pH 3.5. This was stored at 25° C. and analyzed at time 0, at 2 hours and at 24 hours using SEC analysis. SEC analysis was performed as described above, and percentage of high molecular weight aggregates was determined.

|  | % HMW aggregate | | |
|---|---|---|---|
|  | T = 0 | T = 2 hours | T = 4 hours |
| ActRIIB-Fc (E28W) | 1.53 | 1.36 | 13.74 |
| svActRIIB-Fc (E28W, S44T) | 1.66 | 2.17 | 8.93 |

Thus the percentage of high molecular weight aggregates produced at pH 3.5 is substantially less for svActRIIB-Fc (E28W, S44T) than ActRIIB-Fc (E28W) at 4 hours.

Additional studies showed that svActRIIB-Fc (E28W, S44T) showed better reversibility than ActRIIB-Fc (E28W) from exposure to pH 3.0, 3.5 and 5.0, and that svActRIIB-Fc (E28, S44T) was more homogeneous that ActRIIB-Fc (E28W) at all pHs.

Thus, the svActRIIB-Fc (E28W, S44T) polypeptides are demonstrated to have improved manufacturability characteristics, in particular, improved stability at low pH, and greater homogeneity at all pHs compared with ActRIIB-Fc (E28W) while retaining the ability to inhibit activin A, myostatin, and GDF-11 activity.

Example 3

Figure 2:
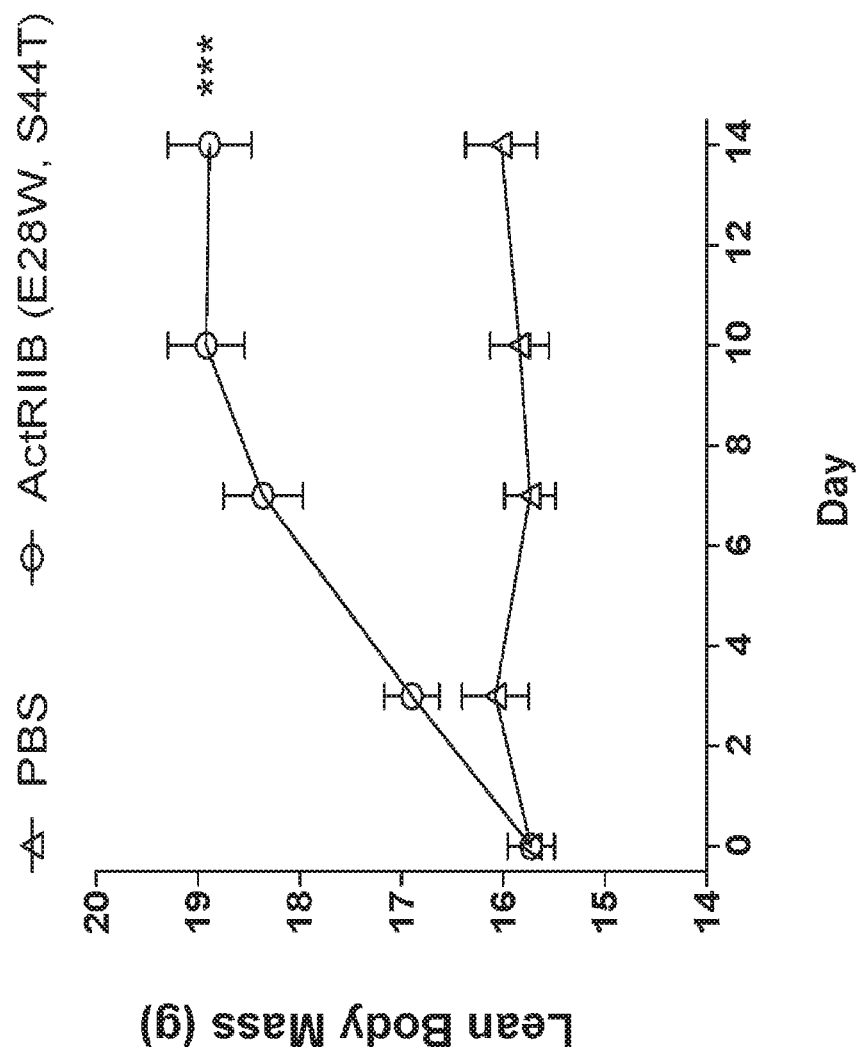
FIG. 2 shows the increase in body mass over a 14 day period in 10 C57Bl/6 mice administered a single dose of 10 mg/kg svActRIIB-Fc (E28W, S44T) compared with 10 mice administered 10 mg/kg of PBS.

Determination of In Vivo Efficacy 11-week-old female C57Bl/6 mice were purchased from Charles River Laboratories. The mice (ten mice per group) were administered a single dose (10 mg/kg) of svActRIIB-Fc (E28W, S44T) (SEQ ID NO: 10) or vehicle (PBS). Lean body mass was determined by NMR (PIXImus, GE LUNAR Corporation) at 3, 7, 10 and 14 days after dose administration for the ten animals in each group. The results for each set of mice are shown in FIG. 2. It can be seen that a single dose of svActRIIB-Fc (E28W, S44T) significantly increased lean body mass in the animals. (P<0.001, based on repeated measurement ANOVA. n=10 animals per group).

Figure 3:
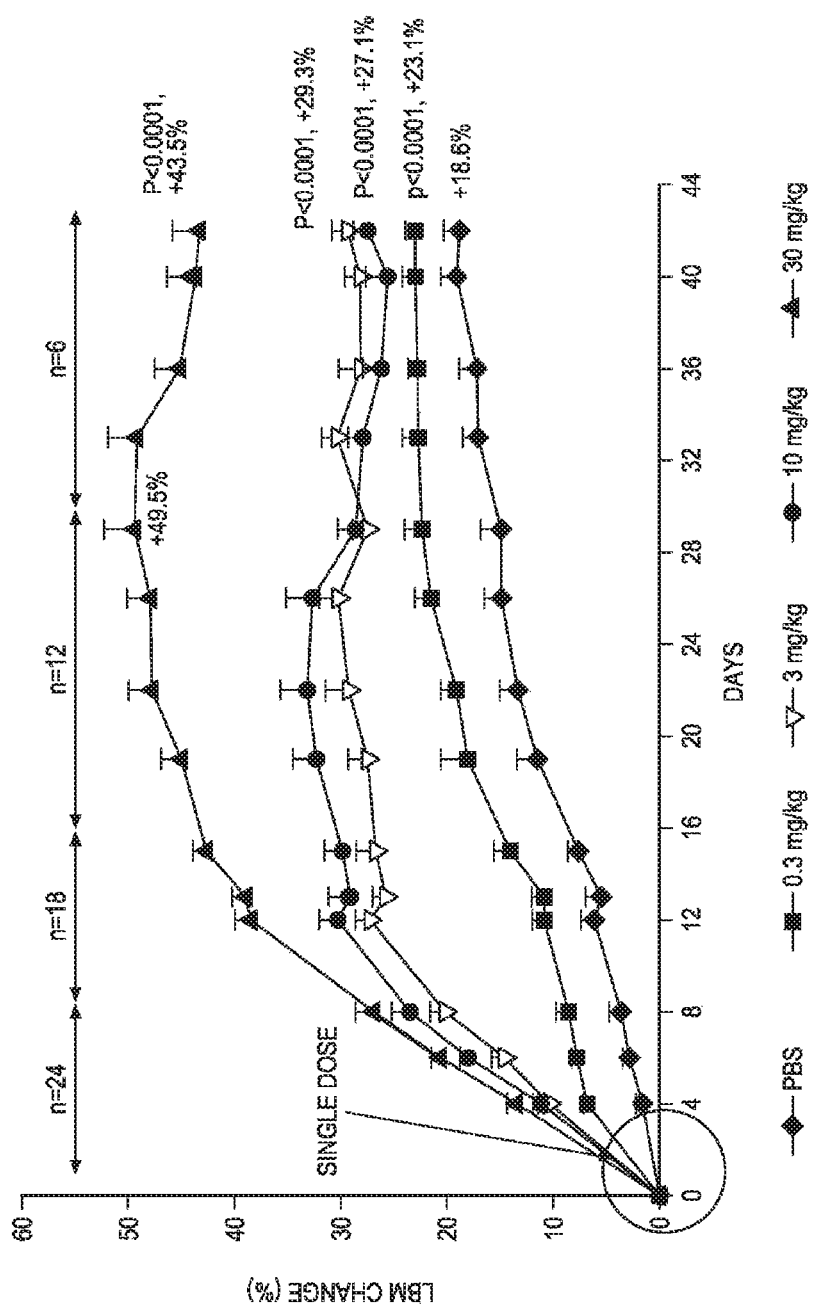
FIG. 3 shows the dose-related change in lean body mass over time for C57Bl/6 receiving a single dose of 0.3 mg/kg, 3 mg/kg, 10 mg/kg, and 30 mg/kg of svActRIIB-Fc (E28W, S44T).

A study to determine dose-response efficacy was carried out as follows. Escalating single doses of 0, 0.3, 3, 10, and 30 mg/kg of svActRIIB-Fc (E28W, S44T) (SEQ ID NO: 10) in PBS was administered subcutaneously to female 10-12 week old C57Bl/6 mice (Charles River Laboratories). Six animals were initially in each dosage group including the PBS control group. Lean body mass was determined by NMR (PIXImus, GE LUNAR Corporation) every two to four days for the forty-two days of the study. At the end of each week, one animal from each group was sacrificed to obtain additional data (six in total each week from all six groups), and the lean body mass determined for the remaining animals in subsequent weeks. The results are set out in FIG. 3. It can be seen that the svActRIIB-Fc (E28W, S44T) polypeptide at all doses significantly increased muscle mass in the animals, in a dose-dependent manner.

In further studies, head to head comparisons between ActRIIB-Fc (E28W) (SEQ ID NO: 21) and svActRIIB-Fc (E28W, S44T) (SEQ ID NO: 10) were performed on female C57Bl/6 mice (Charles River Laboratories, 10 animals per group) to measure the increase in lean muscle mass and body weight changes after a single dose of 10 mg/kg of each soluble receptor compared with a control group (administered PBS). Lean body mass was determined by NMR (PIXImus, GE LUNAR Corporation), and body weight change was determined by weighing the animals periodically for 37 days. The results at the end of this comparative study was that ActRIIB-Fc (E28W) (SEQ ID NO: 21) showed an increase of 24% in lean muscle mass and 25% in increase of body weight compared with an increase of 25% in lean muscle mass and 20% increase in body weight for svActRIIB-Fc (E28W, S44T) (SEQ ID NO: 10), compared with an increase of 5% lean muscle mass and 9% increase body weight for the control group.

Therefore, it can be seen that svActRIIB-Fc (E28W, S44T) retains comparable in vivo efficacy compared with ActRIIB-Fc (E28W) while having improved manufacturability characteristics.

Example 4

Improved Manufacturability with Modified Hinge Linkers

Additional linkers and modified hinge regions were constructed to test for further improvement of protein expression and manufacturability of the stabilized ActRIIB (E28W, S44T) polypeptides. Modified linker/hinge sequences based on modifications of hinge linker #1 were generated using overlap extension PRC mutagenesis methods, according to Mikaelian et al., Methods in Molecular Biology, 57, 193-202 (1996), and well known methodology.

The modified hinge linkers designed to perform well with IgG2 Fc fusions are hinge linker #2-7 set forth below (in comparison to hinge linker #1 sequences).

Hinge Linker #1 Polynucleotide (SEQ ID NO: 26)
ggaggggggaggatctgtcgagtgcccaccgtgccca.

Hinge Linker #1 Polypeptide (SEQ ID NO: 27)
GGGGSVECPPCP

Hinge Linker #2 Polynucleotide (SEQ ID NO: 37)
ggaggggggaggatctgagcgcaaatgttgtgtcgagtgcccaccgtgc Hinge Linker #2 Peptide

```
                                            (SEQ ID NO: 38)
        GGGGSERKCCVECPPC
```

Hinge Linker #3 Polynucleotide

```
                                            (SEQ ID NO: 39)
    ggaggggggaggatctggtggaggtggttcaggtccaccgtgc
```

Hinge Linker #3 Peptide

```
                                            (SEQ ID NO: 40)
        GGGGSGGGGSGPPC
```

Hinge Linker #4 Polynucleotide

```
                                            (SEQ ID NO: 41)
    ggaggggggaggatctggtggaggtggttcaggtccaccggga
```

Hinge Linker #4 Peptide

```
                                            (SEQ ID NO: 42)
        GGGGSGGGGSGPPG
```

Hinge Linker #5 Polynucleotide

```
                                            (SEQ ID NO: 43)
ggaggggggaggatctgagcgcaaatgtccaccttgtgtcgagtgcccacc
gtgc
```

Hinge Linker #5 Peptide

```
                                            (SEQ ID NO: 44)
        GGGGSERKCPPCVECPPC
```

Hinge Linker #6 Peptide

```
                                            (SEQ ID NO: 45)
        GPASGGPASGPPCP
```

Hinge Linker #7 Peptide

```
                                            (SEQ ID NO: 46)
        GPASGGPASGCPPCVECPPCP
```

The following hinge linkers #8 to #10 below were designed to perform well with an IgG1Fc (SEQ ID NO: 23) or the modified IgG1Fc given below (SEQ ID NO: 47 below).

Modified IgG1 Fc

```
                                            (SEQ ID NO: 47)
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHE
ALHNHYTQKSLSLSPGK
```

Hinge Linker #8 Peptide

```
                                            (SEQ ID NO: 48)
        GGGGSVDKTHTCPPCP
```

Hinge Linker #9 Peptide

```
                                            (SEQ ID NO: 49)
        GGGGSVDKTHTGPPCP
```

Hinge Linker #10 Peptide

```
                                            (SEQ ID NO: 50)
        GGGGSGGGGSVDKTHTGPPCP
```

Testing of modified hinge linker sequences with svActRIIB-Fc (28W, S44T) was performed as follows. Polynucleotides encoding svActRIIB (E28W, S44T) (SEQ ID NO: 5), polynucleotides encoding the modified hinge linkers shown above, and polynucleotides encoding IgG2 Fc (SEQ ID NO: 22) or polynucleotides encoding IgG1 Fc (SEQ ID NO: 23) or modified IgG1 Fc (SEQ ID NO: 47) were subcloned into vectors as described in Example 1 and expressed using the transient 293-6E expression system as described in Example 1, except for the following changes: F17 media (Invitrogen) supplemented with 1.1 mg/ml Pluronic, 6 mM L-glutamine and 25 µg/ml geneticin (Invitrogen) was used in place of Freestyle 293 medium as described in Durocher et al., Nucleic Acids Research 30, No. 3, e9 (2002)). The cultures were grown for seven days at 37° C. after transfection. Aliquots were centrifuged to remove cells, and the supernatant was mixed with loading buffer before being heated and loaded onto a 4-20% tris-glycine gel for analysis by Western Blot. After the protein was transferred to a nitrocellulose membrane, samples were probed with a hydrogen peroxidase conjugated anti-human Fc antibody (Pierce #31423) at a dilution of 1:1000.

Protein purification was performed using the following procedure. Approximately 0.25 L of the conditioned media containing the svActRIIB-Fc variants were concentrated using a 5 ft$^2$ 10 K membrane tangential flow filter. The concentrated material was applied to a 5 mL Protein A High Performance Column™ (GE Heathcare) which had been equilibrated with PBS (Dulbecco's with no magnesium chloride or calcium chloride). After washing the column with the equilibration buffer until the absorbance at 280 nm (OD$_{280}$) was less than 0.1, the bound protein was eluted with 0.1 M glycine-HCl, pH 2.7, and immediately neutralized with 1 M Tris-HCl, pH 8.5.

The portion of aggregate in percent and the portion of half molecule in percent were determined by the following method. Denaturing size exclusion chromatography experiments were performed by injecting a 50 µl aliquot of each sample onto an HPLC system with two size exclusion columns (TOSOHAAS G3000swxl) in tandem. The mobile phase contains 5 M GuHCl in phosphate buffered saline (PBS). All samples were diluted to 1 mg/mL in PBS with 7 M GuHCl. The portion of aggregate in percent is determined from the total peak areas of the peaks eluted before the main peak, whereas the portion of half-molecule in percent is determined from the total peak areas of the peaks eluted after the main peak. The half-molecule are believed to represent inactive half-molecules.

Aggregate and half-molecule distribution of svActRIIB-Fc (E28W, S44T) with the various hinge linkers are set forth in the following table.

| Hinge linker sequence | % aggregate | % half molecule |
|---|---|---|
| GGGGSVECPPC (SEQ ID NO: 27) | 0.63 | 15.12 |
| GGGGSERKCCVECPPC (SEQ ID NO: 38) | 15.01 | 7.19 |
| GGGGSGGGGSGPPC (SEQ ID NO: 40) | 0.56 | 3.83 |
| GGGGSGGGGSGPPG (SEQ ID NO: 42) | 0.00 | 99.03 |
| GGGGSERKCPPCVECPPC (SEQ ID NO: 44) | 1.09 | 3.81 |

Thus certain linkers may improve manufacturability of the stabilized ActRIIB-Fc (E28W, S44T) according to these preliminary tests by reducing the percentage of inactive half-molecules produced.

The table below identifies the sequences as listed in the sequence listing.

| SEQ ID NO | Description |
|---|---|
| 1 | ActRIIB extracellular domain, polynucleotide |
| 2 | ActRIIB extracellular domain, polypeptide |
| 3 | svActRIIB (E28W, S44T) polynucleotide with signal sequence |
| 4 | svActRIIB (E28W, S44T) polypeptide with signal sequence |
| 5 | svActRIIB (E28W, S44T) polynucleotide without signal sequence |
| 6 | svActRIIB (E28W, S44T) polypeptide without signal sequence |
| 7 | svActRIIB-Fc (E28W, S44T) polynucleotide with signal sequence |
| 8 | svActRIIB-Fc (E28W, S44T) polypeptide with signal sequence |
| 9 | svActRIIB-Fc (E28W, S44T) polynucleotide without signal sequence |
| 10 | svActRIIB-Fc (E28W, S44T) polypeptide without signal sequence |
| 11 | svActRIIB (E28Y, S44T) polynucleotide with signal sequence |
| 12 | svActRIIB (E28Y, S44T) polypeptide with signal sequence |
| 13 | svActRIIB (E28Y, S44T) polynucleotide without signal sequence |
| 14 | svActRIIB (E28Y, S44T) polypeptide without signal sequence |
| 15 | svActRIIB-Fc (E28Y, S44T) polynucleotide with signal sequence |
| 16 | svActRIIB-Fc (E28Y, S44T) polypeptide with signal sequence |
| 17 | svActRIIB-Fc (E28Y, S44T) polynucleotide without signal sequence |
| 18 | svActRIIB-Fc (E28Y, S44T) polypeptide without signal sequence |
| 19 | ActRIIB (E28W) polypeptide, without signal sequence |
| 20 | ActRIIB-Fc (E28W) polynucleotide, without signal sequence |
| 21 | ActRIIB-Fc (E28W) polypeptide, without signal sequence |
| 22 | IgG2Fc polypeptide sequence |
| 23 | IgG1Fc polypeptide sequence |
| 24 | IgG4 Fc polypeptide sequence |
| 25 | Linker amino acid sequence |
| 26 | Hinge linker #1 polynucleotide sequence |
| 27 | Hinge linker #1 peptide sequence |
| 28 | Hinge region IgG2 |
| 29 | Hinge region IgG1 |
| 30 | Hinge region IgG4 |
| 31 | Alternative signal sequence, polypeptide |
| 32 | Signal sequence, polypeptide |
| 33 | Wild type ActRIIB accession NP_001097 |
| 34 | Activin polypeptide sequence |
| 35 | Myostatin polypeptide sequence |
| 36 | GDF-11 polypeptide sequence |
| 37 | Hinge linker sequence #2 polynucleotide |
| 38 | Hinge linker sequence #2 peptide |
| 39 | Hinge linker sequence #3 polynucleotide |
| 40 | Hinge linker sequence #3 peptide |
| 41 | Hinge linker sequence #4 polynucleotide |
| 42 | Hinge linker sequence #4 peptide |
| 43 | Hinge linker sequence #5 polynucleotide |
| 44 | Hinge linker sequence #5 peptide |
| 45 | Hinge linker sequence #6 peptide |
| 46 | Hinge linker sequence #7 peptide |
| 47 | Modified IgG1 Fc polypeptide sequence |
| 48 | Hinge linker sequence #8 peptide |
| 49 | Hinge linker sequence #9 peptide |
| 50 | Hinge linker sequence #10 peptide |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated nucleic acid molecule comprising a polynucleotide encoding the polypeptide comprising
   (a) a polypeptide consisting of the sequence set forth in SEQ ID NO: 2, except for a single amino acid substitution at position 28, and a single amino acid substitution at position 44, wherein the substitution at position 28 is selected from the group consisting of W and Y, and the substitution at position 44 is T;

(b) a polypeptide consisting of the sequence set forth in amino acids 19 through 134 of SEQ ID NO: 2, except for a single amino acid substitution at position 28, and a single amino acid substitution at position 44, wherein the substitution at position 28 is selected from the group consisting of W and Y, and the substitution at position 44 is T;

(c) a polypeptide consisting of the sequence set forth in amino acids 23 through 134 of SEQ ID NO: 2, except for a single amino acid substitution at position 28, and a single amino acid substitution at position 44, wherein the substitution at position 28 is selected from the group consisting of W and Y, and the substitution at position 44 is T;

(d) a polypeptide consisting of the sequence set forth in amino acids 25 through 134 of SEQ ID NO: 2, except for a single amino acid substitution at position 28, and a single amino acid substitution at position 44, wherein the substitution at position 28 is selected from the group consisting of W and Y, and the substitution at position 44 is T;

(e) a polypeptide having at least 80% sequence identity to any one of (a) through (d), except for a single amino acid substitution at position 28, and a single amino acid substitution at position 44, wherein the substitution at position 28 is selected from the group consisting of W and Y, and the substitution at position 44 is T, wherein the polypeptide is capable of binding myostatin, activin A, or GDF-11.

2. An isolated nucleic acid molecule comprising a polynucleotide selected from the group consisting of:

polynucleotide encoding a polypeptide consisting of the sequence set forth in the group consisting of (a) SEQ ID NO: 6;

(b) a polynucleotide encoding a polypeptide having at least 90% sequence identity to (a), wherein the polypeptide has a W or a Y at position 28 and a T at position 44; and wherein the polypeptide is capable of binding myostatin, activin A, or GDF-11; and (c) a polynucleotide encoding a polypeptide having at least 95% sequence identity to (a), wherein the polypeptide has a W or a Y at position 28 and a T at position 44, and wherein the polypeptide is capable of binding myostatin, activin A, or GDF-11.

3. The nucleic acid molecule of claim 2, wherein the polynucleotide further comprises polynucleotides encoding at least one heterologous protein.

4. The nucleic acid molecule of claim 2, wherein the polynucleotide is operably linked to a transcriptional or translational regulatory sequence.

5. A recombinant vector comprising the nucleic acid molecule of claim 2.

6. A host cell comprising the recombinant vector of claim 5.

7. The host cell of claim 6, wherein the host cell is a mammalian cell.

8. A method of producing a svActRIIB protein comprising culturing the host cell of claim 6 under conditions promoting the expression of the protein, and recovering the protein.

* * * * *